United States Patent
Seo et al.

(10) Patent No.: US 12,410,180 B2
(45) Date of Patent: Sep. 9, 2025

(54) LIGHT-EMITTING DEVICE, LIGHT-EMITTING APPARATUS, ELECTRONIC DEVICE, AND LIGHTING DEVICE

(71) Applicant: Semiconductor Energy Laboratory Co., Ltd., Kanagawa-ken (JP)

(72) Inventors: Satoshi Seo, Kanagawa (JP); Toshiki Sasaki, Kanagawa (JP); Shogo Uesaka, Kanagawa (JP); Shiho Nomura, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 1047 days.

(21) Appl. No.: 17/264,909

(22) PCT Filed: Jul. 25, 2019

(86) PCT No.: PCT/IB2019/056350
§ 371 (c)(1),
(2) Date: Feb. 1, 2021

(87) PCT Pub. No.: WO2020/026088
PCT Pub. Date: Jun. 2, 2020

(65) Prior Publication Data
US 2021/0313520 A1    Oct. 7, 2021

(30) Foreign Application Priority Data
Aug. 3, 2018   (JP) .................... 2018-147134

(51) Int. Cl.
    *C07D 491/048*     (2006.01)
    *C07D 519/00*       (2006.01)
    (Continued)

(52) U.S. Cl.
    CPC ....... *C07D 491/048* (2013.01); *C07D 519/00* (2013.01); *H10K 85/657* (2023.02);
    (Continued)

(58) Field of Classification Search
    CPC ............. H10K 85/657; H10K 85/6572; H10K 85/6574; H10K 85/6576; H10K 50/11;
    (Continued)

(56) References Cited

U.S. PATENT DOCUMENTS

9,553,274 B2    1/2017   Xia et al.
10,680,190 B2   6/2020   Kim et al.
(Continued)

FOREIGN PATENT DOCUMENTS

CN      104292241 A    1/2015
CN      109863614 A    6/2019
(Continued)

OTHER PUBLICATIONS

Lee, J. Y. (2014). Mixed-host-emitting layer for high-efficiency organic light-emitting diodes. Journal of Information Display, 15(3), 139-144. (Year: 2014).*
(Continued)

*Primary Examiner* — Dawn L Garrett
(74) *Attorney, Agent, or Firm* — Husch Blackwell LLP

(57) ABSTRACT

Provided is a light-emitting device that can have sufficient device characteristics even with a smaller number of stacked layers in an EL layer and a thicker light-emitting layer than a conventional one by using, as an organic compound used for the EL layer of the light-emitting device, a material that can increase not only a property of carrier transport to the light-emitting layer but also a property of carrier injection from an electrode.

18 Claims, 12 Drawing Sheets

(51) Int. Cl.
  *H10K 50/11* (2023.01)
  *H10K 50/16* (2023.01)
  *H10K 59/80* (2023.01)
  *H10K 85/60* (2023.01)
  *H10K 101/00* (2023.01)
  *H10K 101/10* (2023.01)
  *H10K 102/00* (2023.01)

(52) U.S. Cl.
  CPC ..... *H10K 85/6572* (2023.02); *H10K 85/6574* (2023.02); *H10K 85/6576* (2023.02); *H10K 50/11* (2023.02); *H10K 50/166* (2023.02); *H10K 59/87* (2023.02); *H10K 2101/10* (2023.02); *H10K 2101/90* (2023.02); *H10K 2102/351* (2023.02)

(58) Field of Classification Search
  CPC ............ H10K 50/166; H10K 2101/10; H10K 2101/90; H10K 2102/351; H10K 85/631; H10K 50/19; H10K 59/00; H10K 85/615; H10K 50/15; H10K 50/84; H10K 77/111; H10K 85/622; C07D 491/048; C07D 19/00; Y02E 10/549; C09K 11/06; C09K 2211/1441
  See application file for complete search history.

(56) References Cited

U.S. PATENT DOCUMENTS

| | | | |
|---|---|---|---|
| 11,530,224 B2 | 12/2022 | Parham et al. | |
| 2004/0124766 A1* | 7/2004 | Nakagawa | H10K 85/656 |
| | | | 313/506 |
| 2007/0159083 A1 | 7/2007 | Matsuura et al. | |
| 2010/0084647 A1* | 4/2010 | Kondakova | H10K 85/30 |
| | | | 257/E51.026 |
| 2015/0021556 A1 | 1/2015 | Xia et al. | |
| 2015/0041795 A1 | 2/2015 | Suzuki et al. | |
| 2017/0141331 A1* | 5/2017 | Kim | H10K 85/324 |
| 2020/0020865 A1 | 1/2020 | Otsu et al. | |
| 2020/0152887 A1 | 5/2020 | Yamaguchi et al. | |

FOREIGN PATENT DOCUMENTS

| | | |
|---|---|---|
| CN | 110073510 A | 7/2019 |
| EP | 2 826 781 A1 | 1/2015 |
| EP | 3 534 424 A1 | 9/2019 |
| JP | 2010-182699 A | 8/2010 |
| JP | 2015-021007 A | 2/2015 |
| JP | 2018-110223 A | 7/2018 |
| JP | 2019-532951 | 11/2019 |
| KR | 2015-0009462 A | 1/2015 |
| KR | 2016-0017530 A | 2/2016 |
| KR | 2019-0052088 A | 5/2019 |
| TW | 201831650 | 9/2018 |
| WO | WO 2018/060307 A1 | 4/2018 |
| WO | WO 2018/079459 A1 | 5/2018 |
| WO | WO 2018/122664 A1 | 7/2018 |

OTHER PUBLICATIONS

International Search Report (Application No. PCT/IB2019/056350) Dated Oct. 21, 2019.

Written Opinion (Application No. PCT/IB2019/056350) Dated Oct. 21, 2019.

* cited by examiner

LIGHT-EMITTING DEVICE, LIGHT-EMITTING APPARATUS, ELECTRONIC DEVICE, AND LIGHTING DEVICE

This application is a 371 of international application PCT/IB2019/056350 filed on Jul. 25, 2019 which is incorporated herein by reference.

TECHNICAL FIELD

One embodiment of the present invention relates to a light-emitting device, a light-emitting apparatus, an electronic device, and a lighting device. However, embodiments of the present invention are not limited thereto. That is, one embodiment of the present invention relates to an object, a method, a manufacturing method, or a driving method. Alternatively, one embodiment of the present invention relates to a process, a machine, manufacture, or a composition of matter.

BACKGROUND ART

A light-emitting device including an EL layer between a pair of electrodes (also referred to as an organic EL device) has characteristics such as thinness, light weight, high-speed response to input signals, and low power consumption; thus, a display including such a light-emitting device has attracted attention as a next-generation flat panel display.

In a light-emitting device, voltage application between a pair of electrodes causes, in an EL layer, recombination of electrons and holes injected from the electrodes, which brings a light-emitting substance (organic compound) contained in the EL layer into an excited state, and the light-emitting substance emits light when returning to the ground state from the excited state. The excited state can be a singlet excited state (S*) and a triplet excited state (T*). Light emission from a singlet excited state is referred to as fluorescence, and light emission from a triplet excited state is referred to as phosphorescence. The statistical generation ratio thereof in the light-emitting device is considered to be S*: T*=1:3. Since the emission spectrum obtained from a light-emitting substance depends on the light-emitting substance, the use of different types of organic compounds as light-emitting substances makes it possible to obtain light-emitting devices which exhibit various emission colors.

In order to improve device characteristics of such a light-emitting device, improvement of a device structure, development of a material, and the like have been actively carried out (see Patent Document 1, for example).

REFERENCE

Patent Document

[Patent Document 1]Japanese Published Patent Application No. 2010-182699

SUMMARY OF THE INVENTION

Problems to be Solved by the Invention

In order to improve device characteristics of a light-emitting device, it is desirable that carriers be efficiently recombined at a desired position in a light-emitting layer of an EL layer.

This needs an improvement in the property of injecting and transporting carriers from both electrodes. In addition, in order to increase the reliability of the device, it is necessary to increase carriers existing in the light-emitting layer and to increase the tolerance of the device to damage caused by driving. Thus, in one embodiment of the present invention, a novel light-emitting device whose device characteristics can be improved without relying on stacking layers alone is provided. Furthermore, a novel light-emitting device whose reliability can be improved is provided.

Note that the descriptions of these objects do not preclude the existence of other objects. One embodiment of the present invention does not have to achieve all these objects. Other objects will be apparent from the descriptions of the specification, the drawings, the claims, and the like, and other objects can be derived from the descriptions of the specification, the drawings, the claims, and the like.

Means for Solving the Problems

One embodiment of the present invention is a light-emitting device that can have sufficient device characteristics even with a smaller number of stacked layers in an EL layer and a thicker light-emitting layer than a conventional one by using, as an organic compound used for the EL layer of the light-emitting device, a material that can increase not only a property of carrier transport to the light-emitting layer but also a property of carrier injection from an electrode.

One embodiment of the present invention is a light-emitting device including an EL layer between an anode and a cathode, in which the EL layer includes a first layer and a second layer; the first layer is in contact with the second layer and positioned between the anode and the second layer; the second layer includes a light-emitting substance, a first organic compound, and a second organic compound; the first organic compound has a structure in which an aromatic ring is fused to a furan ring of a furodiazine skeleton; and the first layer includes the second organic compound.

In the light-emitting device having the above structure, the EL layer includes the first layer, the second layer, and a third layer. The third layer is in contact with the second layer and positioned between the cathode and the second layer. The third layer includes a third organic compound, and the third organic compound is different from the first organic compound.

In the above structure, the light-emitting device includes a fifth layer in contact with the third layer, and the fifth layer includes a compound containing an alkali metal.

In the above structure, the EL layer includes the first layer, the second layer, and a fourth layer. The fourth layer is in contact with the cathode, and the fourth layer includes the first organic compound and a compound containing an alkali metal.

Another embodiment of the present invention is a light-emitting device including an EL layer between an anode and a cathode, in which the EL layer includes a second layer and a fourth layer; the fourth layer is in contact with the cathode; the second layer contains a light-emitting substance; and the fourth layer includes a first organic compound having a structure in which an aromatic ring is fused to a furan ring of a furodiazine skeleton and a compound containing an alkali metal.

In the above structure, the fourth layer is in contact with the second layer.

In any one of the above structures, the first organic compound has a structure in which an aromatic ring is fused to a furan ring of a furopyrazine skeleton or a furopyrimidine skeleton.

Any one of the above structures, the first organic compound is represented by any one of General Formula (G1) below, General Formula (G2) below, and General Formula (G3) below.

[Chemical Formula 1]

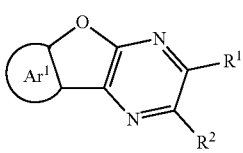

(G1)

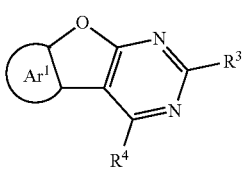

(G2)

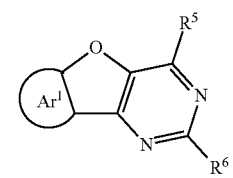

(G3)

(In the formulae, $Ar^1$ represents a substituted or unsubstituted aromatic ring.

Furthermore, each of $R^1$ to $R^6$ independently represents hydrogen or a group having 1 to 100 carbon atoms in total, and at least one of $R^1$ and $R^2$, at least one of $R^3$ and $R^4$, and at least one of $R^5$ and $R^6$ each have a hole-transport skeleton.

Any one of the above structures, the first organic compound is represented by any one of General Formula (G1) below, General Formula (G2) below, and General Formula (G3) below.

[Chemical Formula 2]

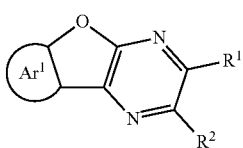

(G1)

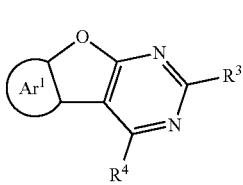

(G2)

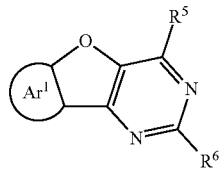

(G3)

(In the formulae, $Ar^1$ represents any one of substituted or unsubstituted benzene, substituted or unsubstituted naphthalene, substituted or unsubstituted phenanthrene, and substituted or unsubstituted chrysene. Furthermore, each of $R^1$ to $R^6$ independently represents hydrogen or a group having 1 to 100 carbon atoms in total, and at least one of $R^1$ and $R^2$, at least one of $R^3$ and $R^4$, and at least one of $R^5$ and $R^6$ each have a hole-transport skeleton.

In the above two structures, $Ar^1$ in General Formula (G1), General Formula (G2), or General Formula (G3) is one of General Formula (t1) to General Formula (t4) below.

[Chemical Formula 3]

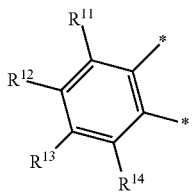

(t1)

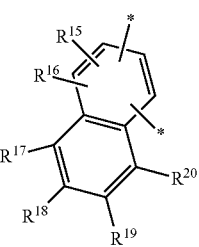

(t2)

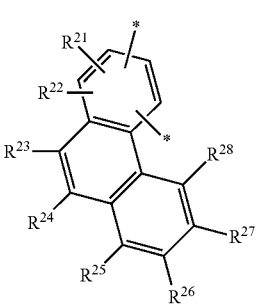

(t3)

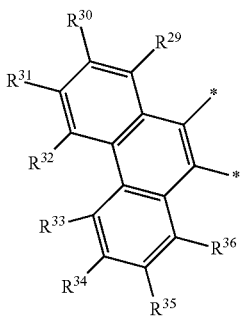

(In the formulae, each of $R^{11}$ to $R^{36}$ independently represents any one of hydrogen, a substituted or unsubstituted alkyl group having 1 to 6 carbon atoms, a substituted or unsubstituted monocyclic saturated hydrocarbon group having 3 to 7 carbon atoms, a substituted or unsubstituted aromatic hydrocarbon group having 6 to 30 carbon atoms, and a substituted or unsubstituted heteroaromatic hydrocarbon group having 3 to 12 carbon atoms. Furthermore, * represents a portion bonded to a furan ring of a furopyrazine skeleton or a furopyrimidine skeleton in General Formula (G1) to General Formula (G3).)

In the above plurality of structures, each of $R^1$ to $R^6$, the group having 1 to 100 carbon atoms in total in General Formula (G1) to General Formula (G3), represents one of or a combination of an alkyl group having 1 to 6 carbon atoms, a substituted or unsubstituted monocyclic saturated hydrocarbon group having 5 to 7 carbon atoms, a substituted or unsubstituted polycyclic saturated hydrocarbon group having 7 to 10 carbon atoms, a substituted or unsubstituted aromatic hydrocarbon group having 6 to 13 carbon atoms, and a substituted or unsubstituted heteroaromatic hydrocarbon group having 3 to 12 carbon atoms.

In the above plurality of structures, each of $R^1$ to $R^6$, the group having 1 to 100 carbon atoms in total in General Formula (G1) to General Formula (G3), has any one of a pyrrole ring structure, a furan ring structure, and a thiophene ring structure through a substituted or unsubstituted phenylene group or a substituted or unsubstituted biphenylene group.

In the above plurality of structures, each of $R^1$ to $R^6$, the group having 1 to 100 carbon atoms in total in General Formula (G1) to General Formula (G3), has a structure represented by any one of General Formulae (Ht-1) to (Ht-26) below through a substituted or unsubstituted phenylene group or a substituted or unsubstituted biphenylene group.

[Chemical Formula 4]

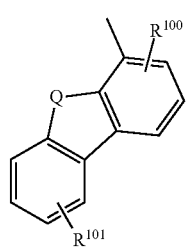
(Ht-1)

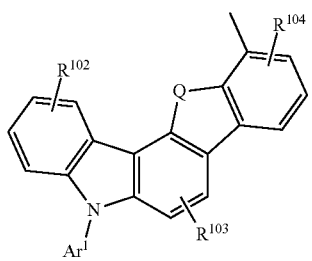
(Ht-2)

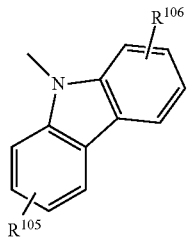
(Ht-3)

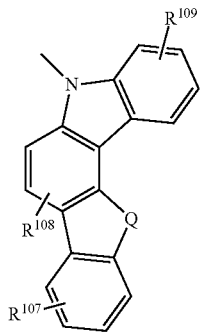
(Ht-4)

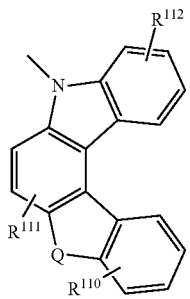
(Ht-5)

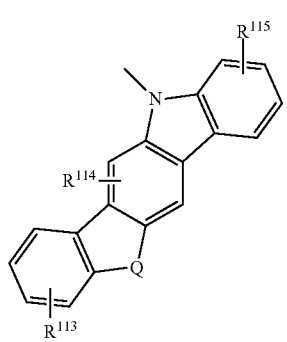
(Ht-6)

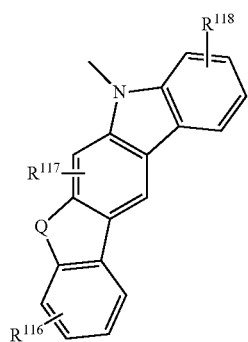
(Ht-7)
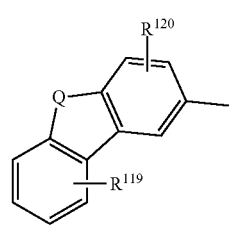
(Ht-8)
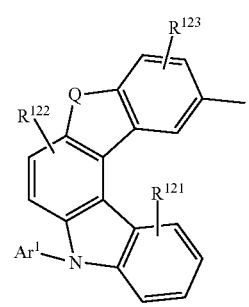
(Ht-9)
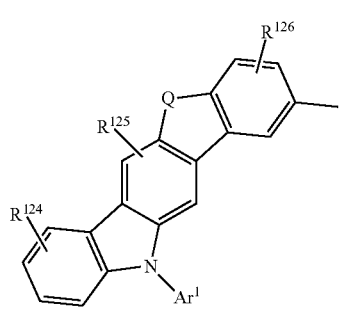
(Ht-10)
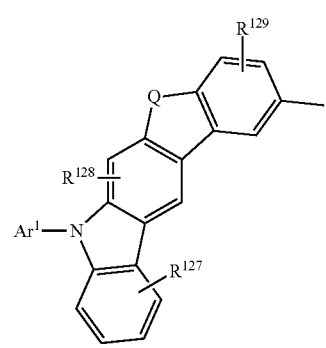
(Ht-11)
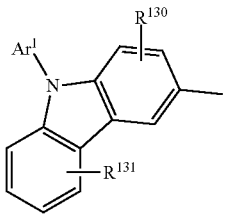
(Ht-12)
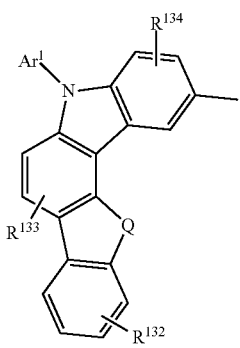
(Ht-13)
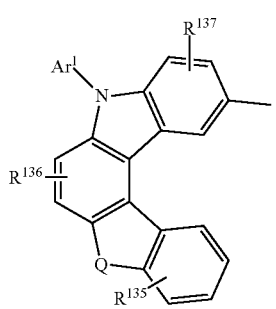
(Ht-14)
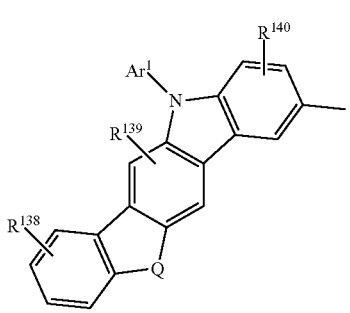
(Ht-15)
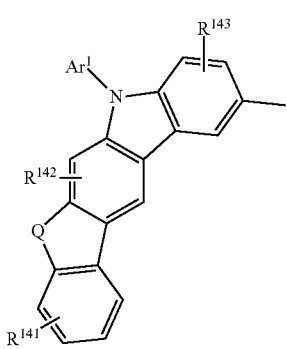
(Ht-16)

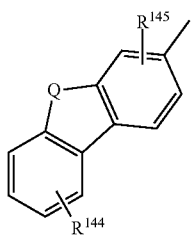 (Ht-17)

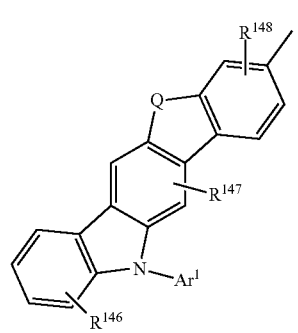 (Ht-18)

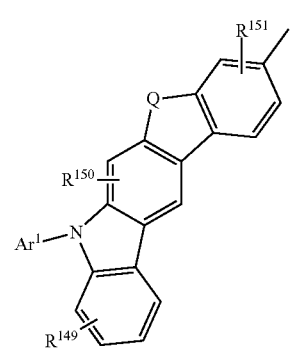 (Ht-19)

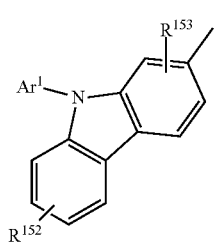 (Ht-20)

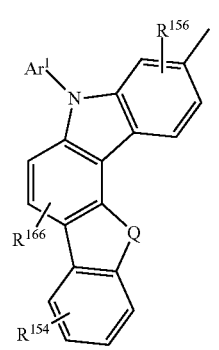 (Ht-21)

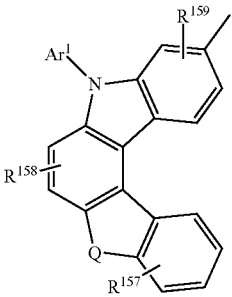 (Ht-22)

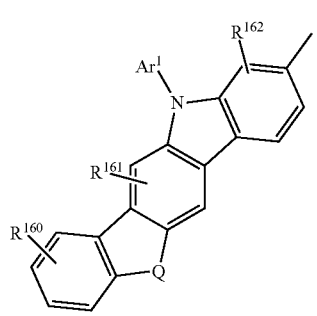 (Ht-23)

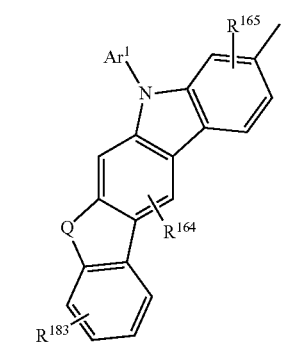 (Ht-24)

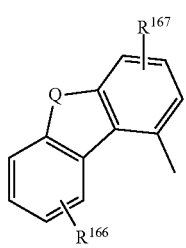 (Ht-25)

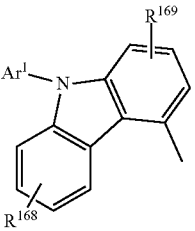 (Ht-26)

(In the formulae, Q represents oxygen or sulfur. Each of $R^{100}$ to $R^{169}$ represents 1 to 4 substituents and independently represents any one of hydrogen, an alkyl group having 1 to 6 carbon atoms, and a substituted or unsubstituted aromatic hydrocarbon group having 6 to 13 carbon atoms. In addition, $Ar^1$ represents a substituted or unsubstituted aromatic hydrocarbon group having 6 to 13 carbon atoms.)

The present invention also includes a light-emitting device having any of the above structures, in which the light-emitting substance is a phosphorescent material. Furthermore, the present invention also includes a light-emitting device including such a light-emitting substance and the second organic compound that is a carbazole derivative, preferably a bicarbazole derivative.

Note that one embodiment of the present invention includes, in its category, in addition to a light-emitting apparatus including the above-described light-emitting device, an electronic device including a light-emitting device or a light-emitting apparatus (specifically, an electronic device including a light-emitting device or a light-emitting apparatus and a connection terminal or an operation key) and a lighting device including a light-emitting device or a light-emitting apparatus (specifically, a lighting device including a light-emitting device or a light-emitting apparatus and a housing). Accordingly, a light-emitting apparatus in this specification refers to an image display device or a light source (including a lighting apparatus). In addition, a light-emitting apparatus includes a module in which a light-emitting apparatus is connected to a connector such as an FPC (Flexible Printed Circuit) or a TCP (Tape Carrier Package), a module in which a printed wiring board is provided on the tip of a TCP, or a module in which an IC (integrated circuit) is directly mounted on a light-emitting device by a COG (Chip On Glass) method.

Effect of the Invention

According to one embodiment of the present invention, a novel light-emitting device whose device characteristics can be improved can be provided. According to another embodiment of the present invention, a novel light-emitting device whose device characteristics can be improved without relying on stacking layers alone can be provided.

Note that the descriptions of the effects do not preclude the existence of other effects. One embodiment of the present invention does not need to have all these effects. Other effects will be apparent from the descriptions of the specification, the drawings, the claims, and the like, and other effects can be derived from the descriptions of the specification, the drawings, the claims, and the like. In addition, a novel light-emitting device whose reliability can be improved can be provided.

MODE FOR CARRYING OUT THE INVENTION

Figure 1A:
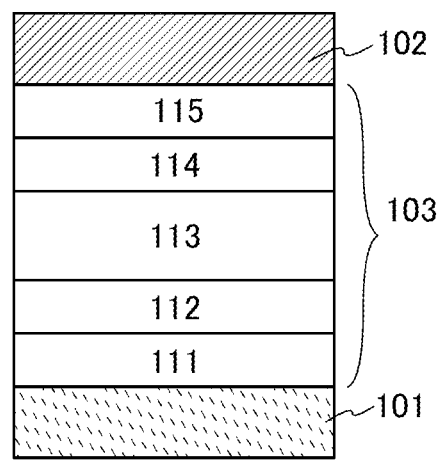
FIGS. 1A and 1B are diagrams each illustrating a structure of a light-emitting device.

Embodiments of the present invention are described in detail below with reference to drawings. Note that the present invention is not limited to the following description, and the modes and details of the present invention can be modified in various ways without departing from the spirit and scope of the present invention. Thus, the present invention should not be construed as being limited to the descriptions in the following embodiments.

Note that the position, size, range, or the like of each structure illustrated in the drawings and the like do not represent the actual position, size, range, or the like in some cases for easy understanding. Therefore, the disclosed invention is not necessarily limited to the position, size, range, or the like disclosed in drawings and the like.

Furthermore, when describing the structures of the invention with reference to the drawings in this specification and the like, the reference numerals denoting the same components are commonly used in different drawings.

Embodiment 1

In this embodiment, a light-emitting device of one embodiment of the present invention is described with reference to FIG. 1.

<<Structure of Light-Emitting Device>>

FIG. 1 illustrates examples of a light-emitting device including, between a pair of electrodes, an EL layer having a light-emitting layer. Specifically, the light-emitting device has a structure in which an EL layer 103 is sandwiched between a first electrode 101 and a second electrode 102. Note that the EL layer 103 has a structure in which, for example, a hole-injection layer 111, a hole-transport layer 112, a light-emitting layer 113, an electron-transport layer 114, and an electron-injection layer 115 are sequentially stacked as functional layers, in the case where the first electrode 101 serves as an anode. Embodiments of the present invention also include light-emitting devices having other structures: for example, a light-emitting device that can be driven at a low voltage by having a structure (a tandem structure) in which a plurality of EL layers, between which a charge-generation layer is sandwiched, are provided between a pair of electrodes; and a light-emitting device that has improved optical characteristics by having a micro-optical resonator (microcavity) structure between a pair of electrodes. Note that the charge generation layer has a function of injecting electrons into one of the adjacent EL layers and injecting holes into the other of the EL layers when a voltage is applied to the first electrode 101 and the second electrode 102.

Note that at least one of the first electrode 101 and the second electrode 102 of the above light-emitting device is an electrode having a light-transmitting property (e.g., a transparent electrode or a semi-transmissive and semi-reflective electrode). In the case where the electrode having a light-transmitting property is a transparent electrode, the visible light transmittance of the transparent electrode is 40% or higher. In the case where the electrode having a light-transmitting property is a semi-transmissive and semi-reflective electrode, the visible light reflectance of the semi-transmissive and semi-reflective electrode is higher than or equal to 20% and lower than or equal to 80%, preferably higher than or equal to 40% and lower than or equal to 70%. The resistivity of these electrodes is preferably $1\times10^{-2}$ Ωcm or lower.

Furthermore, when one of the first electrode 101 and the second electrode 102 is an electrode having reflectivity (reflective electrode) in the above light-emitting device of one embodiment of the present invention, the visible light reflectance of the reflective electrode is higher than or equal to 40% and lower than or equal to 100%, preferably higher than or equal to 70% and lower than or equal to 100%. The resistivity of this electrode is preferably $1\times10^{-2}$ Ωcm or lower.

<First Electrode and Second Electrode>

As materials for forming the first electrode 101 and the second electrode 102, any of the following materials can be used in an appropriate combination as long as the functions of the electrodes described above can be fulfilled. For example, a metal, an alloy, an electrically conductive compound, a mixture of these, and the like can be used as appropriate. Specifically, an In—Sn oxide (also referred to as ITO), an In—Si—Sn oxide (also referred to as ITSO), an In—Zn oxide, or an In—W—Zn oxide can be given. In addition, it is also possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use an element belonging to Group 1 or Group 2 in the periodic table, which is not listed above as an example (for example, lithium (Li), cesium (Cs), calcium (Ca), or strontium (Sr)), a rare earth metal such as europium (Eu) or ytterbium (Yb), an alloy containing an appropriate combination of any of these elements, graphene, or the like.

For fabrication of these electrodes, a sputtering method or a vacuum evaporation method can be used.

<Hole-Injection Layer>

The hole-injection layer 111 is a layer injecting holes from the first electrode 101 that is an anode to the EL layer 103, and is a layer containing an organic acceptor material or a material with a high hole-injection property.

The organic acceptor material is a material that allows holes to be generated in another organic compound whose HOMO level value is close to the LUMO level value of the organic acceptor material when charge separation is caused between the organic acceptor material and the organic compound. Thus, as the organic acceptor material, a compound having an electron-withdrawing group (a halogen group or a cyano group), such as a quinodimethane derivative, a chloranil derivative, and a hexaazatriphenylene derivative, can be used. For example, 7,7,8,8-tetracyano-2,3,5,6-tetrafluoroquinodimethane (abbreviation: F4-TCNQ), 3,6-difluoro-2,5,7,7,8,8-hexacyanoquinodimethane, chloranil, 2,3,6,7,10,11-hexacyano-1,4,5,8,9,12-hexaazatriphenylene (abbreviation: HAT-CN), or 1,3,4,5,7,8-hexafluorotetracyano-naphthoquinodimethane (abbreviation: F6-TCNNQ) can be used. Among organic acceptor materials, HAT-CN, which has a high acceptor property and stable film quality against heat, is particularly favorable. Besides, a [3]radialene derivative has a very high electron-accepting property and thus is preferable; specifically, α,α',α''-1,2,3-cyclopropanetriylidenetris[4-cyano-2,3,5,6-tetrafluorobenzeneacetonitrile], α,α',α''-1,2,3-cyclopropanetriylidenetris[2,6-dichloro-3,5-difluoro-4-(trifluoromethyl)benzeneac etonitrile], α,α',α''-1,2,3-cyclopropanetriylidenetris[2,3,4,5,6-pentafluorobenzeneacetonitrile], or the like can be used.

Examples of the material with a high hole-injection property include transition metal oxides such as molybdenum oxide, vanadium oxide, ruthenium oxide, tungsten oxide, and manganese oxide. Alternatively, it is possible to use a phthalocyanine-based compound such as phthalocyanine (abbreviation: H$_2$Pc) or copper phthalocyanine (abbreviation: CuPc), or the like.

In addition to the above materials, it is also possible to use an aromatic amine compound, which is a low molecular compound, such as 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N-(3-methylphenyl)-N-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), or 3-[N-(1-naphthyl)-N-(9-phenylcarbazol-3-yl)amino]-9-phenylcarbazole (abbreviation: PCzPCN1).

It is also possible to use a high molecular compound (an oligomer, a dendrimer, a polymer, or the like) such as poly(N-vinylcarbazole) (abbreviation: PVK), poly(4-vinyltriphenylamine) (abbreviation: PVTPA), poly[N-(4-{N-[4-(4-diphenylamino)phenyl]phenyl-N-phenylamino}phenyl)methacrylamide](abbreviation: PTPDMA), or poly[N,N-bis(4-butylphenyl)-N,N-bis(phenyl)benzidine](abbreviation: Poly-TPD). Alternatively, it is also possible to use a high molecular compound to which acid is added, such as poly(3,4-ethylenedioxythiophene)/poly(styrenesulfonic acid) (abbreviation: PEDOT/PSS) or polyaniline/poly(styrenesulfonic acid) (abbreviation: PAni/PSS).

Alternatively, as the material having a high hole-injection property, a composite material containing a hole-transport material and an acceptor material (electron-accepting material) can be used. In this case, the acceptor material extracts electrons from a hole-transport material, so that holes are generated in the hole-injection layer 111 and the holes are injected into the light-emitting layer 113 through the hole-transport layer 112. Note that the hole-injection layer 111 may be formed to have a single-layer structure of a composite material containing a hole-transport material and an acceptor material (electron-accepting material), or a stacked-layer structure in which a layer containing a hole-transport material and a layer containing an acceptor material (electron-accepting material) are stacked.

As the hole-transport material, a substance having a hole mobility of greater than or equal to $1\times10^{-6}$ cm$^2$/Vs is preferable. Note that other substances can be used as long as they have a property of transporting more holes than electrons.

As the hole-transport material, materials having a high hole-transport property, such as a π-electron rich heteroaromatic compound (e.g., a carbazole derivative and a furan derivative) and an aromatic amine (a compound having an aromatic amine skeleton), are preferable.

Examples of the above carbazole derivative (a compound having a carbazole skeleton) include a bicarbazole derivative (e.g., a 3,3'-bicarbazole derivative) and an aromatic amine having a carbazolyl group.

Note that specific examples of the bicarbazole derivative (e.g., a 3,3'-bicarbazole derivative) include 3,3'-bis(9-phenyl-9H-carbazole) (abbreviation: PCCP), 9,9'-bis(1,1'-biphenyl-4-yl)-3,3'-bi-9H-carbazole, 9,9'-bis(1,1'-biphenyl-3-yl)-3,3'-bi-9H-carbazole, 9-(1,1'-biphenyl-3-yl)-9'-(1,1'-biphenyl-4-yl)-9H,9'H-3,3'-bicarbazole (abbreviation: mBPCCBP), 9-(2-naphthyl)-9'-phenyl-9H,9'H-3,3'-bicarbazole (abbreviation: pNCCP).

Specific examples of the aromatic amine having the above carbazolyl group include 4-phenyl-4'-(9-phenyl-9H-carbazol-3-yl)triphenylamine (abbreviation: PCBA1BP), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-ami ne (abbreviation: PCBBiF), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNB), 4-phenyldiphenyl-(9-phenyl-9H-carbazol-3-yl)amine (abbreviation: PCA1BP), N,N-bis(9-phenylcarbazol-3-yl)-N,N-diphenylbenzene-1,3-diamine (abbreviation: PCA2B), N,N,N'-triphenyl-N,N,N'-tris(9-phenylcarbazol-3-yl)benzene-1,3,5-triamine (abbreviation: PCA3B), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 2-[N-(9-phenylcarbazol-3-yl)-N-phenylamino]spiro-9,9'-bifluorene (abbreviation: PCASF), N-[4-(9H-carbazol-9-yl)phenyl]-N-(4-phenyl)phenylaniline (abbreviation: YGA1BP), N,N-bis[4-(carbazol-9-yl)phenyl]-N,N-diphenyl-9,9-dimethylfluorene-2,7-diamine (abbreviation: YGA2F), and 4,4',4"-tris(carbazol-9-yl)triphenylamine (abbreviation: TCTA).

In addition to the above, other examples of the carbazole derivative include 3-[4-(9-phenanthryl)-phenyl]-9-phenyl-9H-carbazole (abbreviation: PCPPn), 3-[4-(1-naphthyl)-phenyl]-9-phenyl-9H-carbazole (abbreviation: PCPN), 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA).

Specific examples of the above furan derivative (a compound having a furan skeleton) include compounds having a thiophene skeleton, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV), and compounds having a furan skeleton, such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II).

Specific examples of the above aromatic amine include 4,4'-bis[N-(1-naphthyl)-N-phenylamino]biphenyl (abbreviation: NPB or α-NPD), N,N-bis(3-methylphenyl)-N,N-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N-phenyl-N-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 2,7-bis[N-(4-diphenylaminophenyl)-N-phenylamino]-spiro-9,9'-bifluorene (abbreviation: DPA2SF), 4,4',4"-tris[N-(1-naphthyl)-N-phenylamino]triphenylamine (abbreviation: 1'-TNATA), 4,4',4"-tris(N,N-diphenylamino)triphenylamine (abbreviation: TDATA), 4,4',4"-tris[N-(3-methylphenyl)-N-phenylamino]triphenylamine (abbreviation: m-MTDATA), N,N'-di(p-tolyl)-N,N-diphenyl-p-phenylenediamine (abbreviation: DTDPPA), 4,4'-bis[N-(4-diphenylaminophenyl)-N-phenylamino]biphenyl (abbreviation: DPAB), N,N-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B).

As the hole-transport material, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N-phenylamino}phenyl)methacrylamide](abbreviation: PTPDMA), or poly[N,N-bis(4-butylphenyl)-N,N-bis(phenyl)benzidine](abbreviation: Poly-TPD) can also be used.

Note that the hole-transport material is not limited to the above, and one of or a combination of various known materials may be used as the hole-transport material.

As the acceptor material used for the hole-injection layer 111, an oxide of a metal belonging to any of Group 4 to Group 8 of the periodic table can be used. As specific examples, molybdenum oxide, vanadium oxide, niobium oxide, tantalum oxide, chromium oxide, tungsten oxide, manganese oxide, and rhenium oxide can be given. Among these, molybdenum oxide is particularly preferable since it is stable in the air, has a low hygroscopic property, and is easy to handle. It is also possible to use any of the above-described organic acceptor materials.

Note that the hole-injection layer 111 can be formed by any of various known deposition methods, and can be formed by a vacuum evaporation method, for example.

<Hole-Transport Layer>

The hole-transport layer 112 is a layer transporting holes, which are injected from the first electrode 101 through the hole-injection layer 111, to the light-emitting layer 113. Note that the hole-transport layer 112 is a layer containing a hole-transport material. Thus, for the hole-transport layer 112, a hole-transport material that can be used for the hole-injection layer 111 can be used.

Note that in the light-emitting device of one embodiment of the present invention, the same organic compound as that for the hole-transport layer 112 is preferably used for the light-emitting layer 113. This is because the use of the same organic compounds for the hole-transport layer 112 and the light-emitting layer 113 allows efficient hole transport from the hole-transport layer 112 to the light-emitting layer 113.

<Light-Emitting Layer>

The light-emitting layer 113 is a layer containing a light-emitting substance. There is no particular limitation on the light-emitting substance that can be used for the light-emitting layer 113, and it is possible to use a light-emitting substance that converts singlet excitation energy into light in the visible light range or a light-emitting substance that converts triplet excitation energy into light in the visible light range. In addition, a substance that exhibits emission color of blue, purple, bluish purple, green, yellowish green, yellow, orange, red, or the like can be appropriately used.

In the light-emitting device of one embodiment of the present invention, the light-emitting layer 113 includes a light-emitting substance (guest material) and one or more kinds of organic compounds (e.g., host material). Note that as the organic compound (e.g., host material) used here, it is preferable to use a substance whose energy gap is larger than the energy gap of the light-emitting substance (guest material). Examples of one or more kinds of organic compounds (e.g., host material) include organic compounds such as a hole-transport material that can be used for the hole-transport layer 112 described above and an electron-transport material that can be used for the electron-transport layer 114 described later.

In the case where a phosphorescent material is used as the light-emitting substance (guest material) in the light-emitting layer 113, an organic compound such as a carbazole derivative (e.g., a bicarbazole derivative or an aromatic amine having a carbazolyl group) can be given as a material that is favorably combined with the light-emitting substance, among the above hole-transport materials. Furthermore, among the above electron-transport materials, an organic compound having a structure in which an aromatic ring is fused to a furan ring of a furodiazine skeleton can be given as a material that is favorably combined with the light-emitting substance, for example.

As another structure, the light-emitting layer 113 may have a structure including a plurality of light-emitting layers containing different light-emitting substances to exhibit different emission colors (for example, white light emission obtained by a combination of complementary emission colors). Alternatively, a structure may be employed in which one light-emitting layer includes a plurality of different light-emitting substances.

Examples of the light-emitting substance are given below.

As an example of the light-emitting substance that converts singlet excitation energy into light emission, a substance that emits fluorescence (fluorescent material) can be given; examples include a pyrene derivative, an anthracene derivative, a triphenylene derivative, a fluorene derivative, a carbazole derivative, a dibenzothiophene derivative, a dibenzofuran derivative, a dibenzoquinoxaline derivative, a quinoxaline derivative, a pyridine derivative, a pyrimidine derivative, a phenanthrene derivative, and a naphthalene derivative. A pyrene derivative is particularly preferable because it has a high emission quantum yield. Specific examples of pyrene derivatives include N,N-bis(3-methylphenyl)-N,N-bis[3-(9-phenyl-9H-fluoren-9-yl)phenyl]pyrene-1,6-diamine (abbreviation: 1,6mMemFLPAPrn), N,N-diphenyl-N,N-bis[4-(9-phenyl-9H-fluoren-9-yl)phenyl]pyrene-1,6-diamine (abbreviation: 1,6FLPAPrn), N,A-bis(dibenzofuran-2-yl)-N,N-diphenylpyrene-1,6-diamine (abbreviation: 1,6FrAPrn), N,N-bis(dibenzothiophen-2-yl)-N,N-diphenylpyrene-1,6-diamine (abbreviation: 1,6ThAPrn), N,N-(pyrene-1,6-diyl)bis[(N-phenylbenzo[b]naphtho[1,2-d]furan)-6-amine](abbreviation: 1,6BnfAPrn), N,N-(pyrene-1,6-diyl)bis[(N-phenylbenzo[b]naphtho[1,2-d]furan)-8-amine](abbreviation: 1,6BnfAPrn-02), and N,N-(pyrene-1,6-diyl)bis[(6,N-diphenylbenzo[b]naphtho[1,2-d]furan)-8-amine](abbreviation: 1,6BnfAPrn-03).

In addition, it is possible to use 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N-bis[4-(9H-carbazol-9-yl)phenyl]-N,N-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), 4-(10-phenyl-9-anthryl)-4'-(9-phenyl-9H-carbazol-3-yl)triphenylamine (abbreviation: PCBAPA), 4-[4-(10-phenyl-9-anthryl)phenyl]-4'-(9-phenyl-9H-carbazol-3-yl)triphenylamine (abbreviation: PCBAPBA), perylene, 2,5,8,11-tetra-tert-butylperylene (abbreviation: TBP), N,N'-(2-tert-butylanthracene-9,10-diyldi-4,1-phenylene)bis[N,N,N-triphenyl-1,4-phenylenedia mine](abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N,N-triphenyl-1,4-phenylenediamine (abbreviation: 2DPAPPA), or the like.

Examples of the light-emitting substance that converts triplet excitation energy into light emission include a substance that emits phosphorescence (phosphorescent material) and a thermally activated delayed fluorescence (TADF) material that exhibits thermally activated delayed fluorescence.

Examples of a phosphorescent material include an organometallic complex, a metal complex (platinum complex), and a rare earth metal complex. These substances exhibit different emission colors (emission peaks), and thus are used through appropriate selection as needed.

As examples of a phosphorescent material which exhibits blue or green and whose emission spectrum has a peak wavelength at greater than or equal to 450 nm and less than or equal to 570 nm, the following substances can be given.

For example, organometallic complexes having a 4H-triazole skeleton, such as tris{2-[5-(2-methylphenyl)-4-(2,6-dimethylphenyl)-4H-1,2,4-triazol-3-yl-N$^2$]phenyl-κC}iridiu m(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), tris[4-(3-biphenyl)-5-isopropyl-3-phenyl-4H-1,2,4-triazolato]iridium(III) (abbreviation: [Ir(iPrptz-3b)$_3$]), and tris[3-(5-biphenyl)-5-isopropyl-4-phenyl-4H-1,2,4-triazolato]iridium(III) (abbreviation: [Ir(iPr5btz)$_3$]); organometallic complexes having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1, 2,4-triazolato)iridium(III) (abbreviation: [Ir(Prptz1-Me)$_3$]); organometallic complexes having an imidazole skeleton, such as fac-tris[1-(2,6-diisopropylphenyl)-2-phenyl-1H-imidazole]iridium(III) (abbreviation: [Ir(iPrpmi)$_3$]) and tris [3-(2,6-dimethylphenyl)-7-methylimidazo[1,2-f] phenanthridinato]iridium(III) (abbreviation: [Ir(dmpimpt-Me)$_3$]); organometallic complexes in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$] iridium(III) picolinate (abbreviation: FIrpic), bis{2-[3',5'-bis (trifluoromethyl)phenyl]pyridinato-N,C$^{2'}$}iridium(III) picolinate (abbreviation: [Ir(CF$_3$ppy)$_2$(pic)]), and bis[2-(4', 6'-difluorophenyl)pyridinato-N,C$^{2'}$]iridium(III) acetylacetonate (abbreviation: FIr(acac)); and the like can be given.

As a phosphorescent material that exhibits green or yellow and whose emission spectrum has a peak wavelength at greater than or equal to 495 nm and less than or equal to 590 nm, the following substances can be given.

For example, organometallic iridium complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(t-Buppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato) iridium(III) (abbreviation: [Ir(tBuppm)$_2$(acac)]), (acetylacetonato)bis[6-(2-norbornyl)-4-phenylpyrimidinato]iridium (III) (abbreviation: [Ir(nbppm)$_2$(acac)]), (acetylacetonato) bis[5-methyl-6-(2-methylphenyl)-4-phenylpyrimidinato] iridium(III) (abbreviation: [Ir(mpmppm)$_2$(acac)]), (acetylacetonato)bis{4,6-dimethyl-2-[6-(2,6-dimethylphenyl)-4-pyrimidinyl-kN$^3$]phenyl-κC}iridium(III) (abbreviation: [Ir(dmppm-dmp)$_2$(acac)]), and (acetylacetonato)bis(4, 6-diphenylpyrimidinato)iridium(III) (abbreviation: [Ir (dppm)$_2$(acac)]); organometallic iridium complexes having a pyrazine skeleton, such as (acetylacetonato)bis(3,5-dimethyl-2-phenylpyrazinato)iridium(III) (abbreviation: [Ir (mppr-Me)$_2$(acac)]) and (acetylacetonato)bis(5-isopropyl-3-methyl-2-phenylpyrazinato)iridium(III) (abbreviation: [Ir (mppr-iPr)$_2$(acac)]); organometallic iridium complexes having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), bis(2-phenylquinolinato-N,C$^{2'}$)iridium(III) acetylacetonate (abbreviation: [Ir(pq)$_2$(acac)]), bis[2-(2-pyridinyl-κN)phenyl-κC][2-(4-phenyl-2-pyridinyl-κN)phenyl-κC]iridium(III) (abbreviation: [Ir(ppy)$_2$(4dppy)]), and bis[2-(2-pyridinyl-κN)phenyl-κC][2-(4-methyl-5-phenyl-2-pyridinyl-κN)phenyl-κC]; organometallic complexes such as bis(2,4-diphenyl-1,3-oxazolato-N,C$^{2'}$)iridium(III) acetylacetonate (abbreviation: [Ir(dpo)$_2$(acac)]), bis{2-[4'-(perfluorophenyl)phenyl]pyridinato-N,C$^{2'}$}iridium(III) acetylacetonate (abbreviation: [Ir(p-PF-ph)$_2$(acac)]), and bis(2-phenylbenzothiazolato-N,C$^{2'}$)iridium(III) acetylacetonate (abbreviation: [Ir(bt)$_2$(acac)]); and rare earth metal complexes such as tris(acetylacetonato)(monophenanthroline) terbium(III) (abbreviation: [Tb(acac)$_3$(Phen)]) can be given.

As a phosphorescent material that exhibits yellow or red and whose emission spectrum has a peak wavelength at greater than or equal to 570 nm and less than or equal to 750 nm, the following substances can be given.

For example, organometallic complexes having a pyrimidine skeleton, such as (diisobutyrylmethanato)bis[4,6-bis(3-methylphenyl)pyrimidinato]iridium(III) (abbreviation: [Ir (5mdppm)$_2$(dibm)]), bis[4,6-bis(3-methylphenyl)pyrimidinato](dipivaloylmethanato)iridium(III) (abbreviation: [Ir (5mdppm)$_2$(dpm)]), and (dipivaloylmethanato)bis[4,6-di (naphthalen-1-yl)pyrimidinato]iridium(III) (abbreviation: [Ir(dlnpm)$_2$(dpm)]); organometallic complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium (III) (abbreviation: [Ir(tppr)$_2$(dpm)]), bis{4,6-dimethyl-2-[3-(3,5-dimethylphenyl)-5-phenyl-2-pyrazinyl-N]phenyl-κC}(2,6-dimethyl-3,5-heptanedionato-κ$^2$O,O')iridium(III) (abbreviation: [Ir(dmdppr-P)$_2$(dibm)]), bis{4,6-dimethyl-2-[5-(4-cyano-2,6-dimethylphenyl)-3-(3,5-dimethylphenyl)-2-pyrazinyl-κN]phenyl-κC}(2,2,6,6-tetramethyl-3,5-heptanedionato-κ$^2$O,O')iridium(III) (abbreviation: [Ir(dmdppr-dmCP)$_2$(dpm)]), (acetylacetonato)bis[2-methyl-3-phenylquinoxalinato-N,C$^{2'}$]iridium(III) (abbreviation: [Ir(mpq)$_2$ (acac)]), (acetylacetonato)bis(2,3-diphenylquinoxalinato-N, C$^{2'}$)iridium(III) (abbreviation: [Ir(dpq)$_2$(acac)]), and (acetylacetonato)bis[2,3-bis(4-fluorophenyl)quinoxalinato] iridium(III) (abbreviation: [Ir(Fdpq)$_2$(acac)]); organometallic complexes having a pyridine skeleton, such as tris(1-phenylisoquinolinato-N,C$^{2'}$)iridium(III) (abbreviation: [Ir (piq)$_3$]), bis(1-phenylisoquinolinato-N,C$^{2'}$)iridium(III) acetylacetonate (abbreviation: [Ir(piq)$_2$(acac)]), and bis[4,6-dimethyl-2-(2-quinolinyl-κN)phenyl-κC](2,4-pentanedionato-κ$^2$O,O')iridium(III) (abbreviation: [Ir(dmpqn)$_2$(acac)]); platinum complexes such as 2,3,7,8,12,13,17,18-octaethyl-21H,23H-porphyrinplatinum(II) (abbreviation: [PtOEP]); and rare earth metal complexes such as tris(1,3-diphenyl-1, 3-propanedionato)(monophenanthroline)europium(III) (abbreviation: [Eu(DBM)$_3$(Phen)]) and tris[1-(2-thenoyl)-3,3, 3-trifluoroacetonato](monophenanthroline)europium(III) (abbreviation: [Eu(TTA)$_3$(Phen)]) can be given.

Shown below are specific examples of the organic compound having a structure in which an aromatic ring is fused to a furan ring of a furodiazine skeleton, which is an electron-transport material shown above as a material that can be used for the light-emitting layer 113. Note that any of these electron-transport materials can also be used for the electron-transport layer 114 described later.

[Chemical Formula 5]
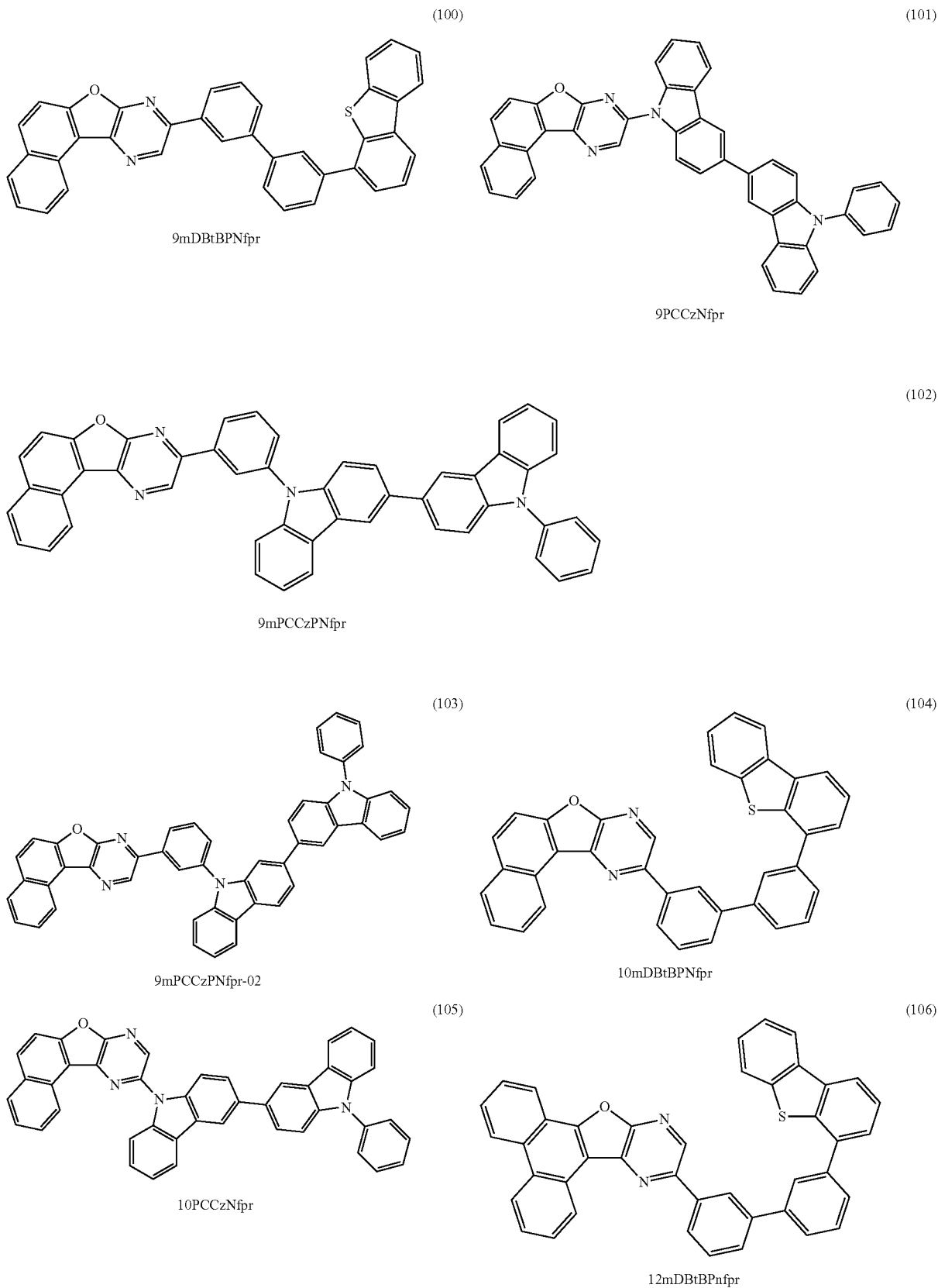

-continued
(107)
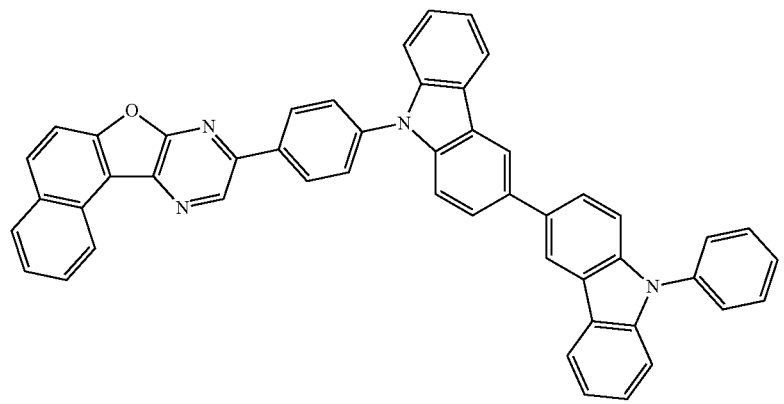
9pPCCzPNfpr
(108)
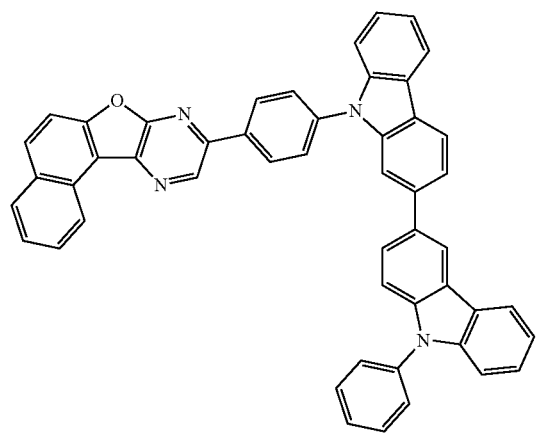
(109)
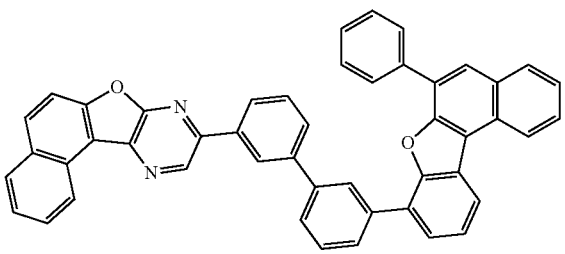
9mBnfBPNfpr
(110)
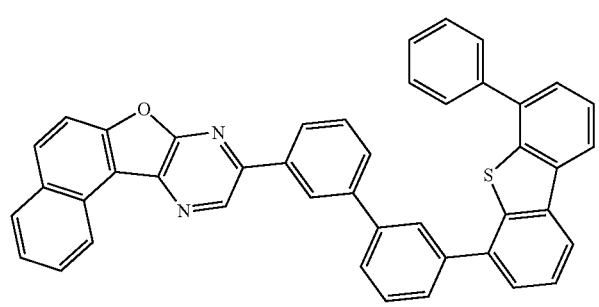
9mDBtBPNfpr-02

[Chemical Formula 6]
(111)
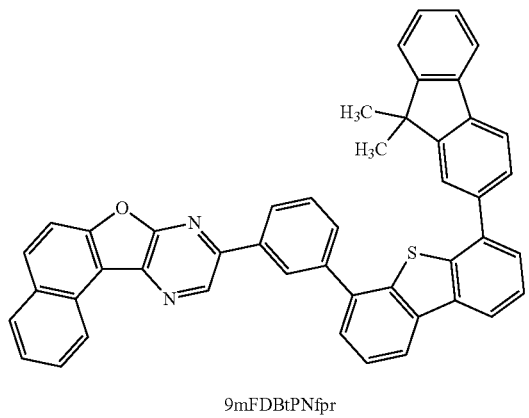
9mFDBtPNfpr
(112)
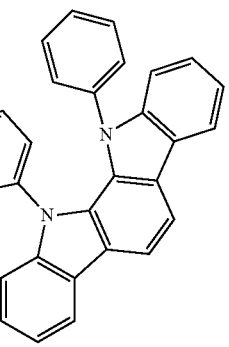
9mIcz(II)PNfpr
(113)
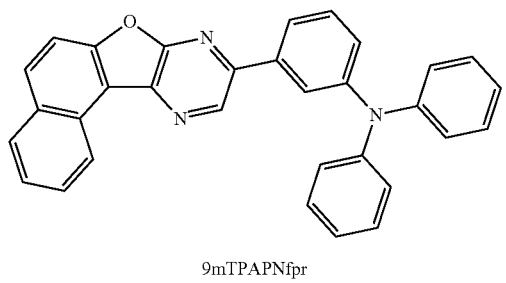
9mTPAPNfpr
(114)
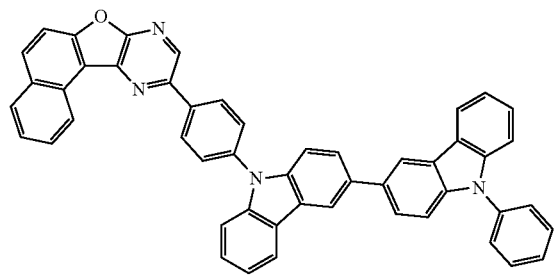
10mPCCzPNfpr
(115)
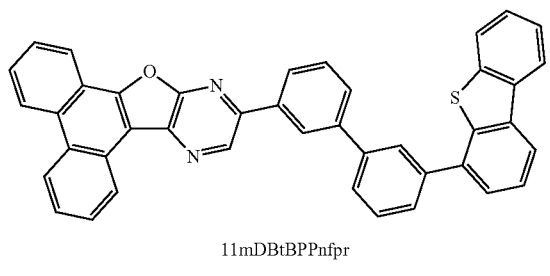
11mDBtBPPnfpr
(116)
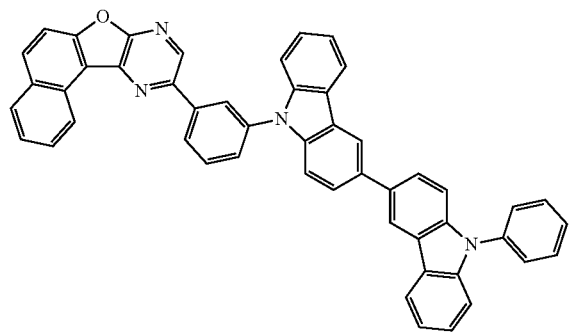
10pPCCzPNfpr -continued
(117)
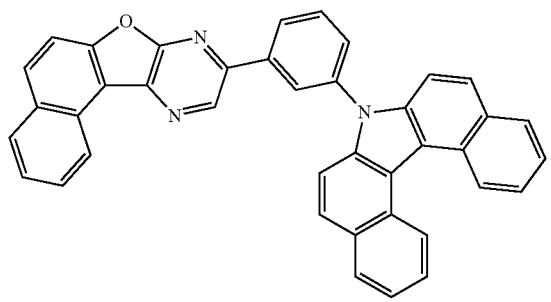
9mcgDBCzPNfpr
(118)
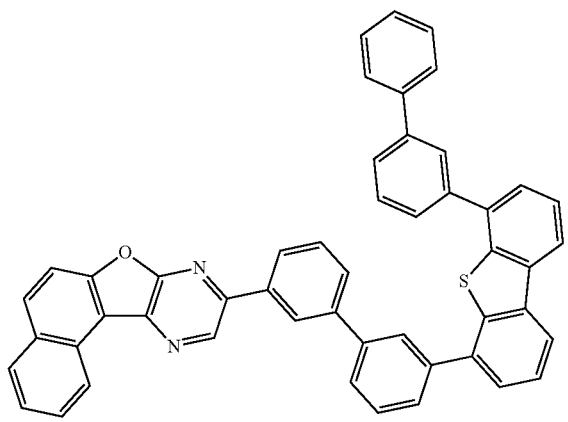
9mDBtBPNfpr-03
(119)
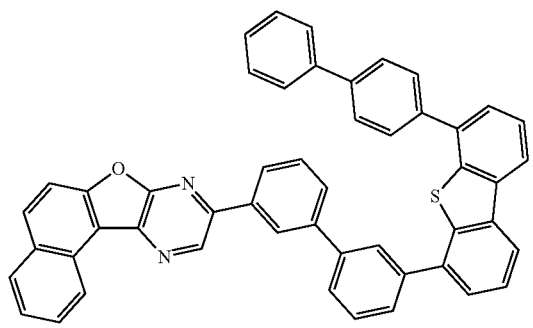
9mDBtBPNfpr-04
(120)
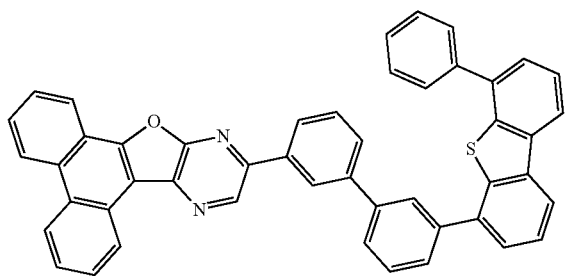
11mDBtBPPnfpr
[Chemical Formula 7]
(200)
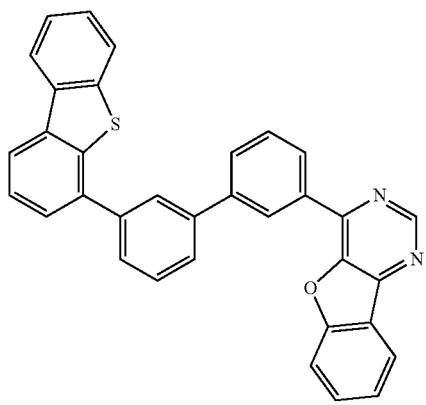
4mDBtBPBfpm-II
(201)
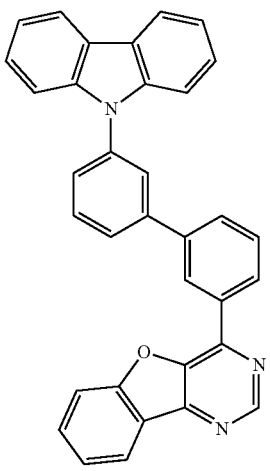
4mCzBPBfpm -continued
(202)
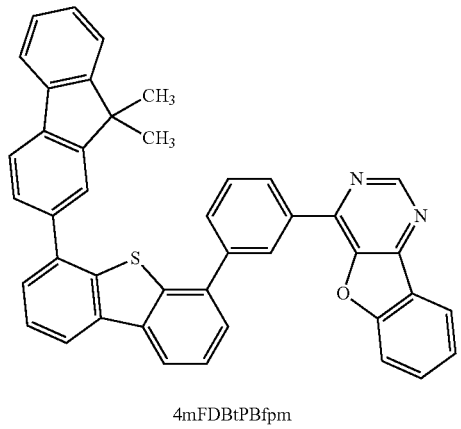
4mFDBtPBfpm
(203)
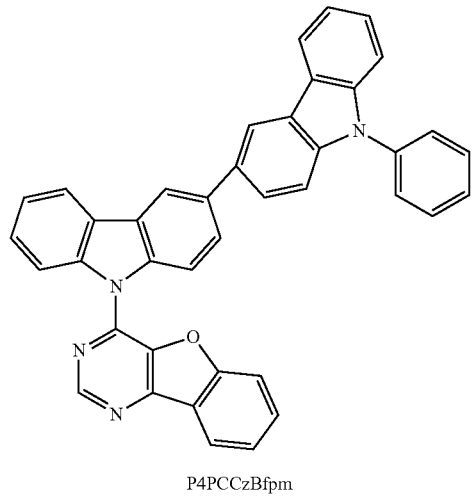
P4PCCzBfpm
(204)
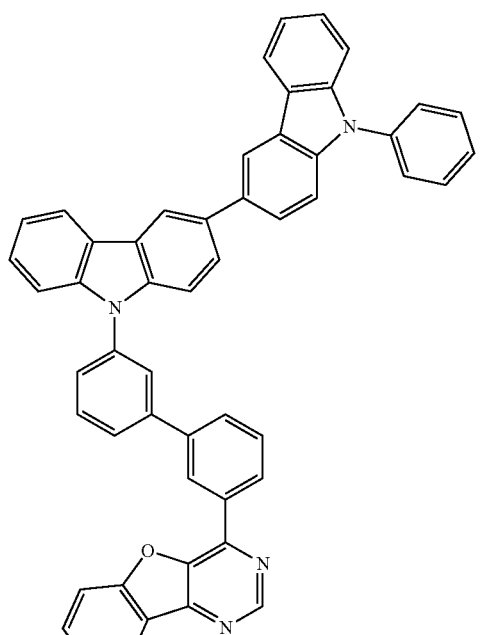
4PCCzPBfpm
(205)
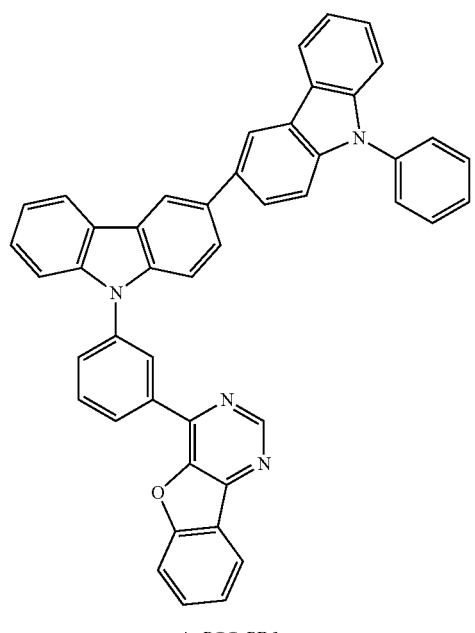
4mPCCzPBfpm (206)
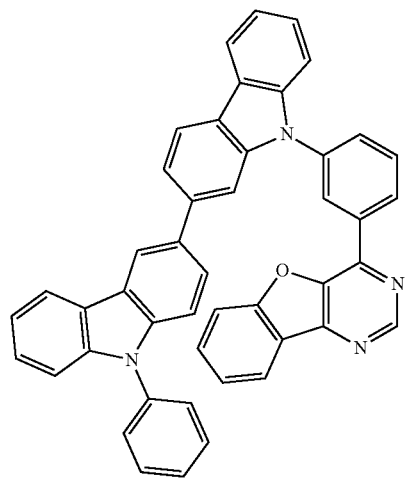
4mPCCzPBfpm-02
(207)
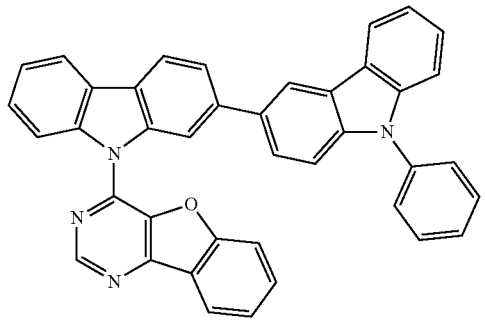
4PCCzBfpm-02
(208)
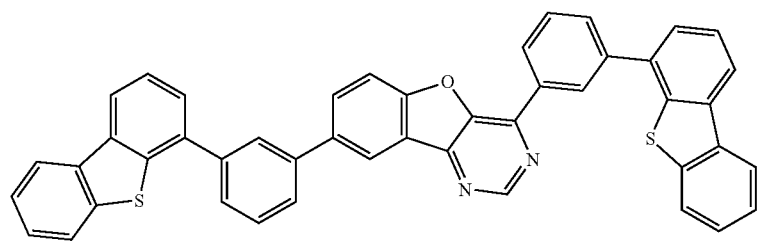
4,8mDBtP2Bfpm
(209)
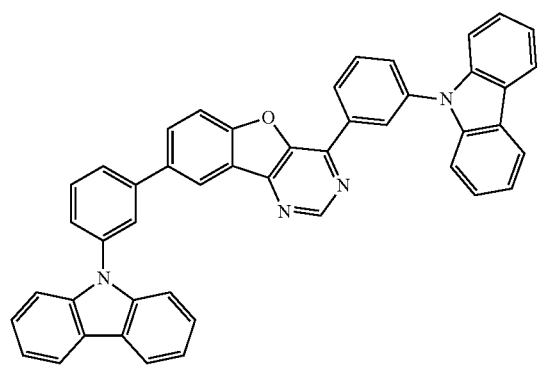
4,8mCzP2Bfpm
(210)
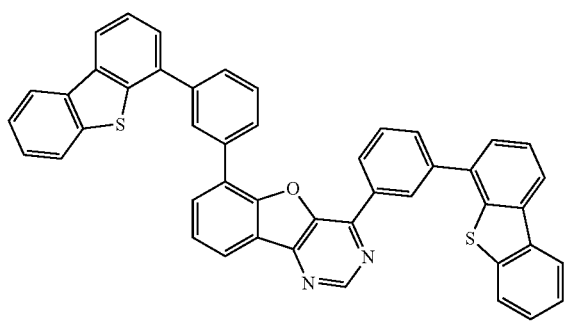
4,6mDBtP2Bfpm

[Chemical Formula 8]
(211)
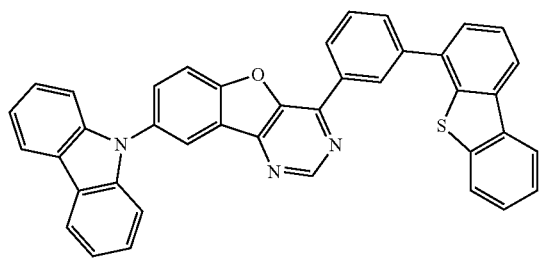
8Cz-4mDBtPBfpm
(212)
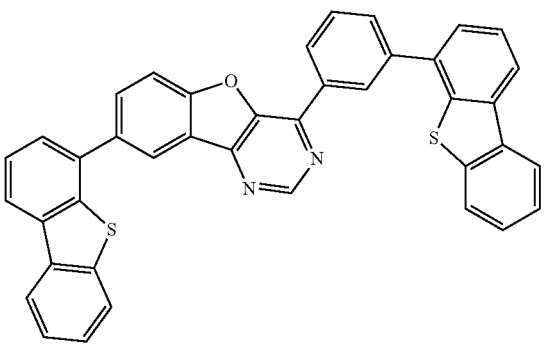
8DBt-4mDBtPBfpm
(213)
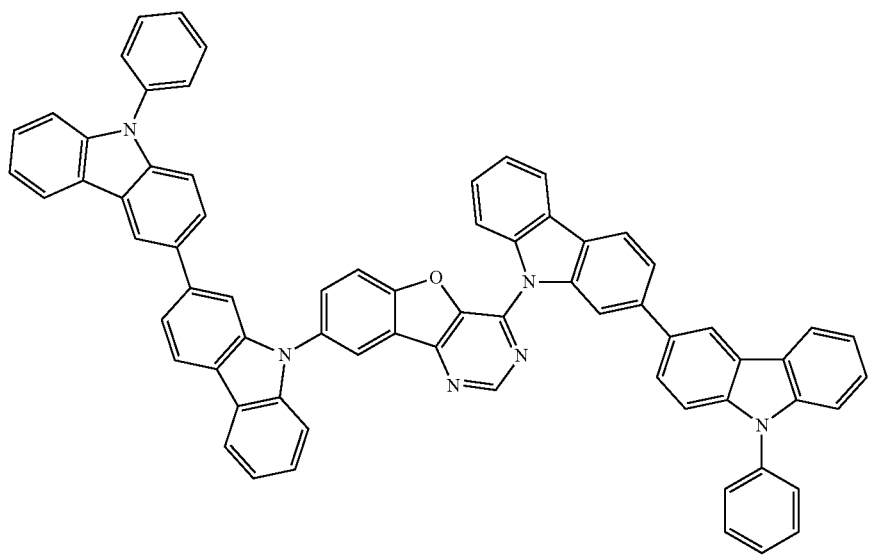
4,8PCCz2Bfpm-02
(214)
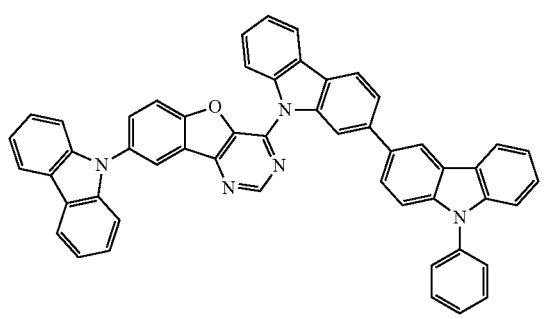
8Cz-4PCCz2Bfpm-02
(215)
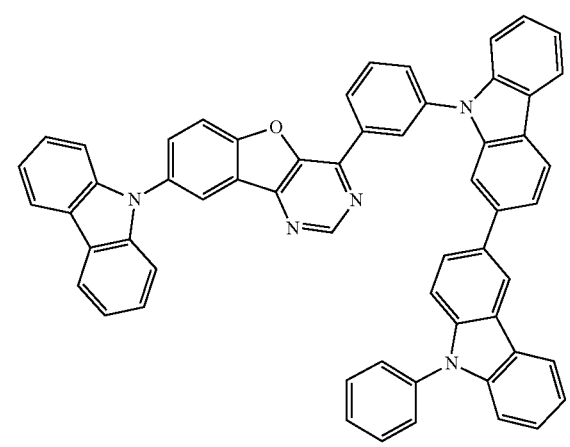
8Cz-4PCCz2Bfpm-02

-continued
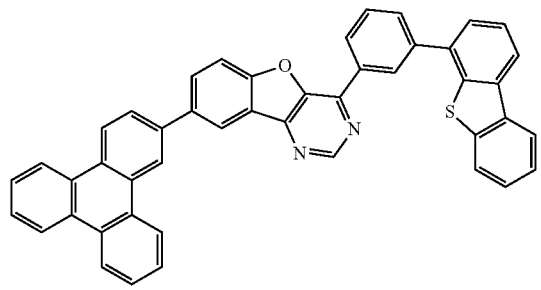
8Tp-4mDBtPBfpm (216)
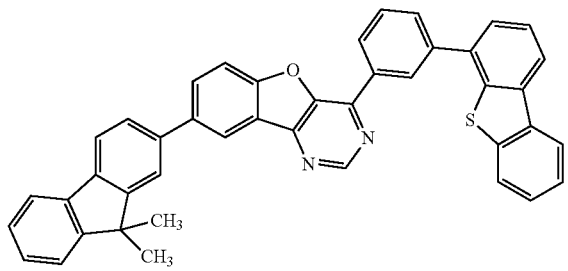
8FL-4mDBtPBfpm (217)
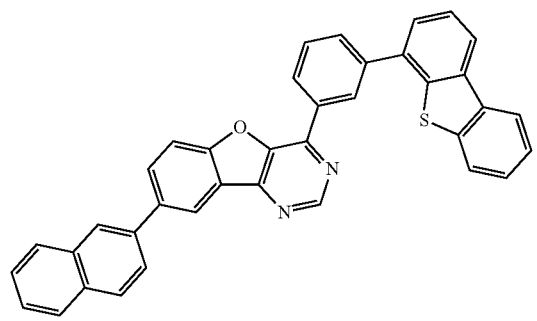
8βN-4mDBtPMfpm (218)
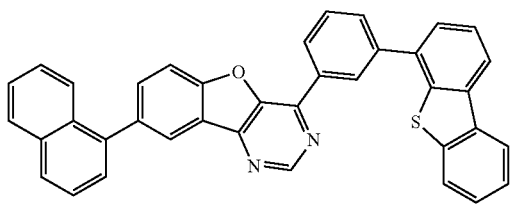
8aN-4mDBtPFfpm (219)
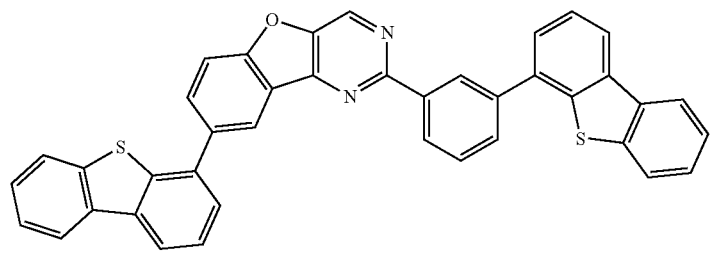
8DBt-2mDBtPBfpm (220)
[Chemical Formula 9]
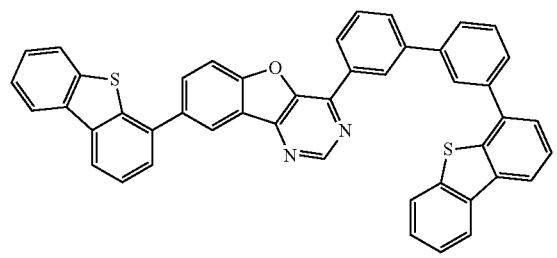
8DBt-4mDBtBPBfpm (221)
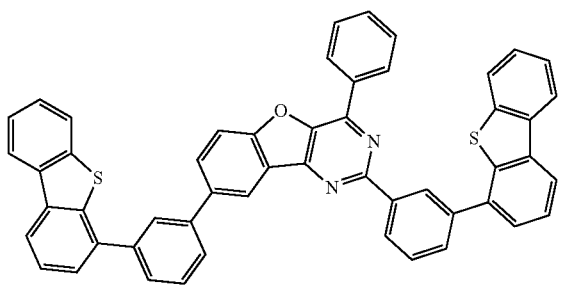
4Ph-2,8mDBtP2Bfpm (222)

-continued
(223)
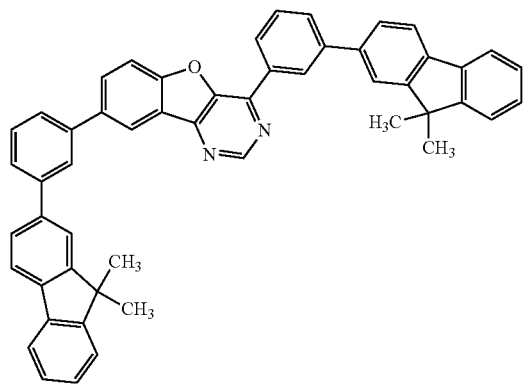
4,8mFP2Bfpm
(224)
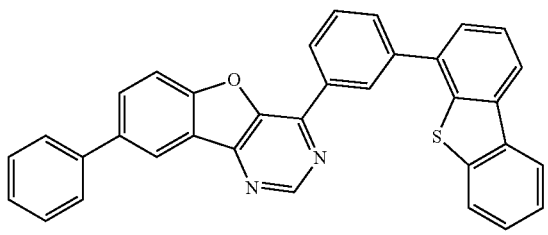
8Ph-4mDBtPBfpm
(225)
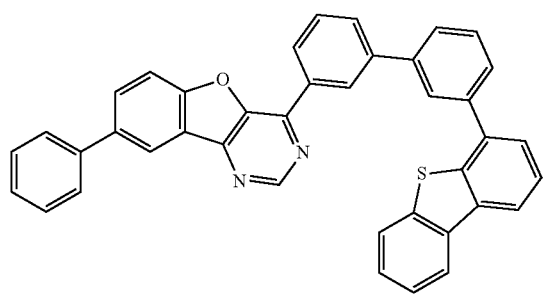
8Ph-4mDBtBPBfpm
(226)
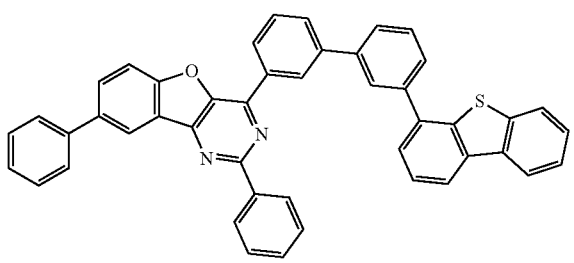
2,8Ph-4mDBtBPBfpm
(227)
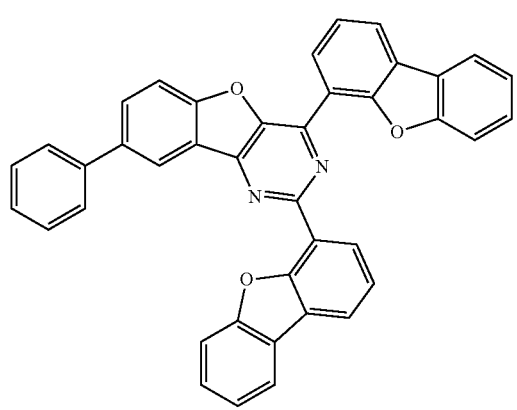
8Ph-2,4DBf2Bfpm
(228)
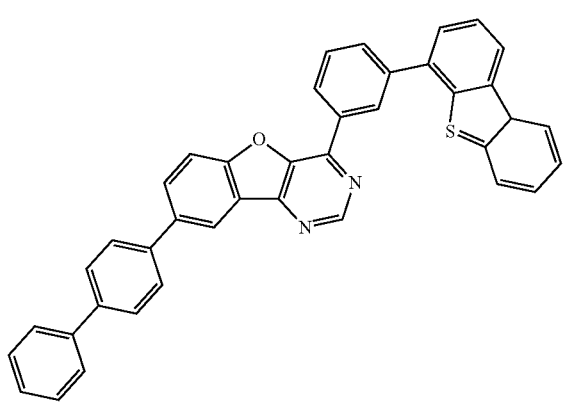
8BP-4mDBtPBfpm -continued

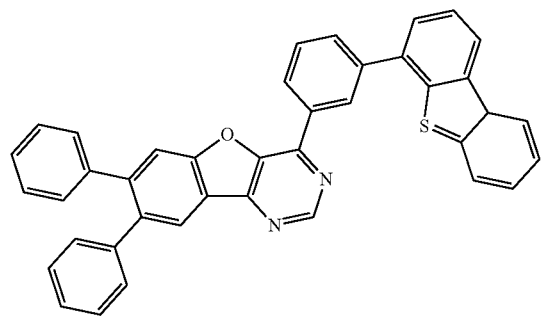

8mBP-4mDBtPBfpm (229)

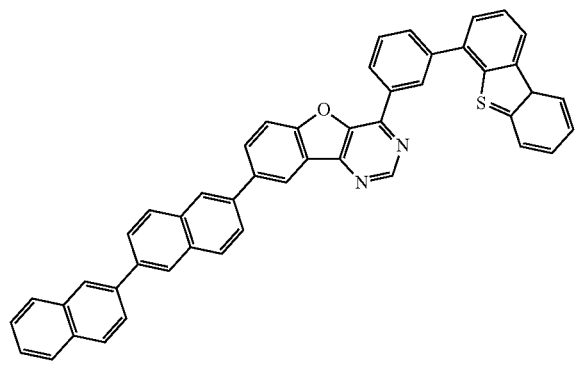

8(βN2)-4mDBtPBfpm (230)

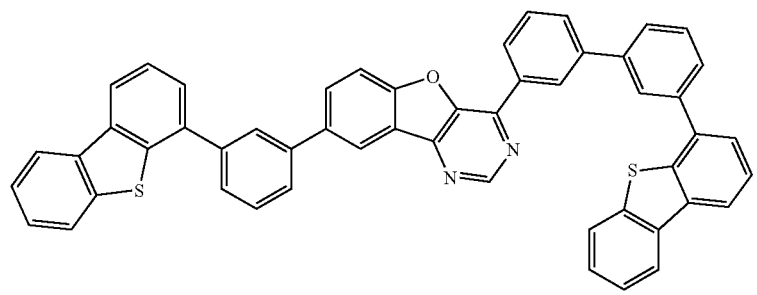

8mDBtP-4mDBtBPBfpm (231)

In addition to the above organic compounds, other examples of the organic compound that can be used for the light-emitting layer 113 are given below (some of them overlap with the above) in terms of favorable combination with a light-emitting substance (a fluorescent material or a phosphorescent material).

In the case where the light-emitting substance is a fluorescent material, examples of the organic compound that is favorably combined with the fluorescent material include condensed polycyclic aromatic compounds, such as an anthracene derivative, a tetracene derivative, a phenanthrene derivative, a pyrene derivative, a chrysene derivative, and a dibenzo[g,p]chrysene derivative.

Specific examples of the organic compound (the host material) that is favorably combined with the fluorescent material include 9-phenyl-3-[4-(10-phenyl-9-anthryl)phenyl]-9H-carbazole (abbreviation: PCzPA), 3,6-diphenyl-9-[4-(10-phenyl-9-anthryl)phenyl]-9H-carbazole (abbreviation: DPCzPA), 3-[4-(1-naphthyl)-phenyl]-9-phenyl-9H-carbazole (abbreviation: PCPN), 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), YGAPA, PCAPA, N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), 6,12-dimethoxy-5,11-diphenylchrysene, N,N,N,N,N',N',N'',N''-octaphenyldibenzo[g,p]chrysene-2,7,10,15-tetraamine (abbreviation: DBC1), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)-biphenyl-4'-yl}-anthracene (abbreviation: FLPPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 1,3,5-tri(1-pyrenyl)benzene (abbreviation: TPB3), 5,12-diphenyltetracene, and 5,12-bis(biphenyl-2-yl)tetracene.

In the case where the light-emitting substance is a phosphorescent material, an organic compound having triplet excitation energy (energy difference between a ground state and a triplet excited state) higher than that of the light-emitting substance is preferably selected as the organic compound that is favorably combined with the phosphorescent material. Note that in the case where a plurality of organic compounds (e.g., a first host material and a second host material (or an assist material)) are used in combination with a light-emitting substance in order to form an exciplex, the plurality of organic compounds are preferably mixed with a phosphorescent material.

Such a structure makes it possible to efficiently obtain light emission utilizing ExTET (Exciplex-Triplet Energy Transfer), which is energy transfer from an exciplex to a light-emitting substance. Note that a combination of the plurality of organic compounds that easily forms an exciplex is preferably employed, and it is particularly preferable to combine a compound that easily accepts holes (hole-transport material) and a compound that easily accepts electrons (electron-transport material).

In the case where the light-emitting substance is a phosphorescent material, examples of the organic compounds (the host material and the assist material) that is favorably combined with the phosphorescent material include an aromatic amine, a carbazole derivative, a dibenzothiophene derivative, a dibenzofuran derivative, a zinc- or aluminum-based metal complex, an oxadiazole derivative, a triazole derivative, a benzimidazole derivative, a quinoxaline derivative, a dibenzoquinoxaline derivative, a pyrimidine derivative, a pyrazine derivative, a triazine derivative, a pyridine derivative, a bipyridine derivative, and a phenanthroline derivative.

Specific examples include triazole derivatives such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 3-(4-biphenylyl)-4-phenyl-5-(4-tert-butylphenyl)-1,2,4-triazole (abbreviation: TAZ), and 3-(4-tert-butylphenyl)-4-(4-ethylphenyl)-5-(4-biphenylyl)-1,2,4-triazole (abbreviation: p-EtTAZ); and quinoxaline derivatives or dibenzoquinoxaline derivatives, such as 2,2',2"-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), 4,4'-bis(5-methylbenzoxazol-2-yl)stilbene (abbreviation: BzOs), bathophenanthroline (abbreviation: Bphen), bathocuproine (abbreviation: BCP), 2,9-bis(naphthalen-2-yl)-4,7-diphenyl-1,10-phenanthroline (abbreviation: NBphen), 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II).

Specific examples further include pyrimidine derivatives such as 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), 4,6-bis[3-(9H-carbazol-9-yl)phenyl]pyrimidine (abbreviation: 4,6mCzP2Pm); triazine derivatives such as 2-{4-[3-(N-phenyl-9H-carbazol-3-yl)-9H-carbazol-9-yl]phenyl}-4,6-diphenyl-1,3,5-triazine (abbreviation: PCCzPTzn); triazine derivatives such as 9-[3-(4,6-diphenyl-1,3,5-triazin-2-yl)phenyl]-9'-phenyl-2,3'-bi-9H-carbazole (abbreviation: mPCCzPTzn-02); and pyridine derivatives such as 3,5-bis[3-(9H-carbazol-9-yl)phenyl]pyridine (abbreviation: 35DCzPPy), and 1,3,5-tri[3-(3-pyridyl)phenyl]benzene (abbreviation: TmPyPB).

Furthermore, a high-molecular compound such as poly (2,5-pyridinediyl) (abbreviation: PPy), poly[(9,9-dihexylfluorene-2,7-diyl)-co-(pyridine-3,5-diyl)](abbreviation: PF-Py), or poly[(9,9-dioctylfluorene-2,7-diyl)-co-(2,2'-bipyridine-6,6'-diyl)](abbreviation: PF-BPy) can be used.

In the case where a plurality of organic compounds are used in the light-emitting layer 113, two kinds of compounds that form an exciplex (a first organic compound and a second organic compound) and a light-emitting substance may be mixed and used. In this case, various organic compounds can be used in appropriate combination; to form an exciplex efficiently, it is particularly preferable to combine a compound that easily accepts holes (hole-transport material) and a compound that easily accepts electrons (electron-transport material). Note that, as specific examples of the hole-transport material and the electron-transport material, the materials described in this embodiment can be used. With the structure, high efficiency, low voltage, and a long lifetime can be achieved at the same time.

The TADF material is a material that can up-convert a triplet excited state into a singlet excited state (reverse intersystem crossing) using a little thermal energy and efficiently exhibits light emission (fluorescence) from the singlet excited state. The thermally activated delayed fluorescence is efficiently obtained under the condition where the difference in energy between the triplet excited level and the singlet excited level is greater than or equal to 0 eV and less than or equal to 0.2 eV, preferably greater than or equal to 0 eV and less than or equal to 0.1 eV. Note that delayed fluorescence by the TADF material refers to light emission having a spectrum similar to that of normal fluorescence and an extremely long lifetime. The lifetime is $10^{-6}$ seconds or longer, preferably $10^{-3}$ seconds or longer.

Examples of the TADF material include fullerene, a derivative thereof, an acridine derivative such as proflavine, and eosin. Other examples include a metal-containing porphyrin such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (abbreviation: $SnF_2$(Proto IX)), a mesoporphyrin-tin fluoride complex (abbreviation: $SnF_2$(Meso IX)), a hematoporphyrin-tin fluoride complex (abbreviation: $SnF_2$(Hemato IX)), a coproporphyrin tetramethyl ester-tin fluoride complex (abbreviation: $SnF_2$(Copro III-4Me)), an octaethylporphyrin-tin fluoride complex (abbreviation: $SnF_2$(OEP)), an etioporphyrin-tin fluoride complex (abbreviation: $SnF_2$(Etio I)), and an octaethylporphyrin-platinum chloride complex (abbreviation: $PtCl_2OEP$).

Alternatively, a heterocyclic compound having a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) may be used.

Note that a substance in which a π-electron rich heteroaromatic ring is directly bonded to a π-electron deficient heteroaromatic ring is particularly preferable because both the donor property of the π-electron rich heteroaromatic ring and the acceptor property of the π-electron deficient heteroaromatic ring are improved and the energy difference between the singlet excited state and the triplet excited state becomes small.

Note that the TADF material can also be used in combination with another organic compound. In particular, the TADF material can be combined with the host materials, the hole-transport materials, and the electron-transport materials described above, and the organic compound of one embodiment of the present invention described in Embodiment 1 is preferably used as a host material for the TADF material.

Any of the above materials may be used in combination with a low-molecular material or a high-molecular material.

For the deposition, a known method (a vacuum evaporation method, a coating method, a printing method, or the like) can be used as appropriate.

<Electron-Transport Layer>

The electron-transport layer 114 is a layer transporting electrons, which are injected from the second electrode 102 through the electron-injection layer 115 to be described later, to the light-emitting layer 113. Note that the electron-transport layer 114 is a layer containing an electron-transport material. As the electron-transport material, a substance having an electron mobility of greater than or equal to $1 \times 10^{-6}$ cm$^2$/Vs is preferable. Note that other substances can be used as long as they have a property of transporting more electrons than holes. The electron-transport layers (114, 114a, and 114b) each function even with a single-layer structure, but can improve the device characteristics when having a stacked-layer structure of two or more layers as needed.

As the organic compound that can be used for the electron-transport layer 114, it is possible to use, in addition to the electron-transport materials (the organic compounds having a structure in which an aromatic ring is fused to a furan ring of a furodiazine skeleton) specifically given above as examples that can be used in the light-emitting layer 113, a material having a high electron-transport property (an electron-transport material), such as a metal complex having a quinoline skeleton, a metal complex having a benzoquinoline skeleton, a metal complex having an oxazole skeleton, a metal complex having a thiazole skeleton, an oxadiazole derivative, a triazole derivative, an imidazole derivative, an oxazole derivative, a thiazole derivative, a phenanthroline derivative, a quinoline derivative having a quinoline ligand, a benzoquinoline derivative, a quinoxaline derivative, a dibenzoquinoxaline derivative, a pyridine derivative, a bipyridine derivative, a pyrimidine derivative, or a π-electron deficient heteroaromatic compound such as a nitrogen-containing heteroaromatic compound.

Specific examples of the electron-transport material (other than the organic compound having a structure in which an aromatic ring is fused to a furan ring of a furodiazine skeleton) include metal complexes having a quinoline skeleton or a benzoquinoline skeleton, such as tris(8-quinolinolato)aluminum(III) (abbreviation: Alq$_3$), tris (4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), and bis(8-quinolinolato)zinc(II) (abbreviation: Znq), and metal complexes having an oxazole skeleton or a thiazole skeleton, such as bis[2-(2-benzoxazolyl)phenolato]zinc(II) (abbreviation: ZnPBO), bis[2-(2-benzothiazolyl)phenolato] zinc(II) (abbreviation: ZnBTZ), and bis[2-(2-hydroxyphenyl)benzothiazolato]zinc(II) (abbreviation: Zn(BTZ)$_2$).

Other than the metal complexes, it is possible to use oxadiazole derivatives such as PBD, OXD-7, and CO11, triazole derivatives such as TAZ and p-EtTAZ, imidazole derivatives (including benzimidazole derivatives) such as TPBI and mDBTBIm-II, an oxazole derivative such as BzOs, phenanthroline derivatives such as Bphen, BCP, and NBphen, quinoxaline derivatives and dibenzoquinoxaline derivatives, such as 2mDBTPDBq-II, 2mDBTBPDBq-II, 2mCzBPDBq, 2CzPDBq-III, 7mDBTPDBq-II, and 6mDBTPDBq-II, pyridine derivatives such as 35DCzPPy and TmPyPB, pyrimidine derivatives such as 4,6mPnP2Pm, 4,6mDBTP2Pm-II, and 4,6mCzP2Pm, and triazine derivatives such as PCCzPTzn and mPCCzPTzn-02.

It is also possible to use high-molecular compounds such as PPy, PF-Py, and PF-BPy.

Note that for the electron-transport layer 114 of the light-emitting device of one embodiment of the present invention, it is preferable to use an electron-transport material (an organic compound having a structure in which an aromatic ring is fused to a furan ring of a furodiazine skeleton) in combination with an alkali metal or an alkaline earth metal, a compound thereof, or the like. Such a combination enables the electron-transport layer 114 to function also as an electron-injection layer; thus, a light-emitting device in which the electron-injection layer 115 is not formed between the electron-transport layer 114 and the second electrode 102 can have substantially the same characteristics and reliability as in the case where the electron-injection layer 115 is formed.

Specific examples of the alkali metal or the alkaline earth metal include lithium (Li), cesium (Cs), magnesium (Mg), and calcium (Ca). As the compound of an alkali metal or an alkaline earth metal, it is possible to use an inorganic compound such as lithium oxide or cesium carbonate or an organic compound such as 8-(quinolinolato)lithium (abbreviation: Liq), 2-(2-pyridyl)phenolatolithium (abbreviation: LiPP), 2-(2-pyridyl)-3-pyridinolato lithium (abbreviation: LiPPy), or 4-phenyl-2-(2-pyridyl)phenolatolithium (abbreviation: LiPPP).

In the light-emitting device of another embodiment of the present invention, which uses for the light-emitting layer 113 an organic compound having a structure in which an aromatic ring is fused to a furan ring of a furodiazine skeleton, sufficient characteristics can be obtained even when the electron-transport layer 114 has a single-layer structure.

<Electron-Injection Layer>

The electron-injection layer 115 is a layer for increasing the efficiency of electron injection from the cathode; thus, the electron-injection layer 115 is preferably formed using a material whose LUMO level value has a small difference (0.5 eV or less) from the work function value of a cathode material. Thus, the electron-injection layer 115 can be formed using an alkali metal, an alkaline earth metal, or a compound thereof, such as lithium, cesium, lithium fluoride (LiF), cesium fluoride (CsF), calcium fluoride (CaF$_2$), 8-(quinolinolato)-lithium (abbreviation: Liq), 2-(2-pyridyl) phenolatolithium (abbreviation: LiPP), 2-(2-pyridyl)-3-pyridinolatolithium (abbreviation: LiPPy), 4-phenyl-2-(2-pyridyl)phenolatolithium (abbreviation: LiPPP), lithium oxide (LiO$_x$), or cesium carbonate. A rare earth metal compound like erbium fluoride (ErF$_3$) can also be used.

Figure 1B:
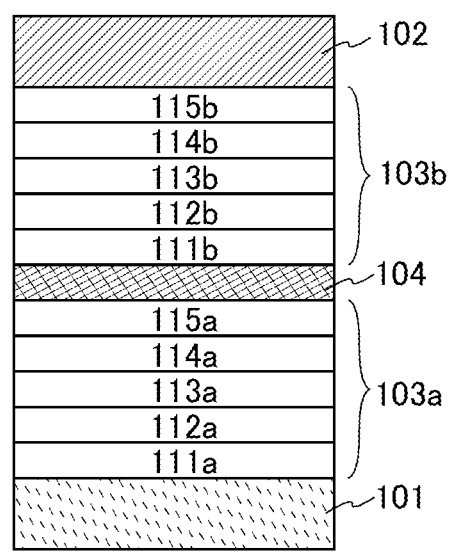

When a charge-generation layer 104 is provided between two EL layers (103a and 103b) as in the light-emitting device illustrated in FIG. 1B, a structure in which a plurality of EL layers are stacked between the pair of electrodes (also referred to as a tandem structure) can be employed. Note that in this embodiment, functions and materials of the hole-injection layer (111), the hole-transport layer (112), the light-emitting layer (113), the electron-transport layer (114), and the electron-injection layer (115) that are illustrated in FIG. 1A are the same as those of hole-injection layer (111a and 1/1b), hole-transport layers (112a and 112b), light-emitting layers (113a and 113b), electron-transport layers (114a and 114b), and electron-injection layers (115a and 115b) that are illustrated in FIG. 1B.

<Charge-Generation Layer>

In the light-emitting device of FIG. 1B, the charge-generation layer 104 has a function of injecting electrons into the EL layer 103a and injecting holes into the EL layer 103b when voltage is applied between the first electrode (anode) 101 and the second electrode (cathode) 102. Note that the charge-generation layer 104 may have either a structure in which an electron acceptor (acceptor) is added to a hole-transport material or a structure in which an electron donor (donor) is added to an electron-transport material. Alternatively, both of these structures may be stacked. Note that forming the charge-generation layer 104 with the use of any of the above materials can suppress an increase in drive voltage in the case where the EL layers are stacked.

In the case where the charge-generation layer 104 has a structure in which an electron acceptor is added to a hole-transport material, any of the materials described in this embodiment can be used as the hole-transport material. As the electron acceptor, 7,7,8,8-tetracyano-2,3,5,6-tetrafluoroquinodimethane (abbreviation: $F_4$-TCNQ), chloranil, and the like can be given. Other examples include oxides of metals belonging to Group 4 to Group 8 of the periodic table. Specific examples are vanadium oxide, niobium oxide, tantalum oxide, chromium oxide, molybdenum oxide, tungsten oxide, manganese oxide, and rhenium oxide.

In the case where the charge-generation layer 104 has a structure in which an electron donor is added to an electron-transport material, any of the materials described in this embodiment can be used as the electron-transport material. As the electron donor, it is possible to use an alkali metal, an alkaline earth metal, a rare earth metal, metals belonging to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. An organic compound such as tetrathianaphthacene may be used as the electron donor.

Although FIG. 1B illustrates the structure in which two EL layers 103 are stacked, a structure may be employed in which three or more EL layers are stacked with a charge generation layer provided between different EL layers.

<Substrate>

The light-emitting device described in this embodiment can be formed over any of a variety of substrates. Note that the type of the substrate is not limited to a certain type. Examples of the substrate include semiconductor substrates (e.g., a single crystal substrate and a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, a laminate film, paper including a fibrous material, and a base material film.

Note that examples of the glass substrate include barium borosilicate glass, aluminoborosilicate glass, and soda lime glass. Examples of the flexible substrate, the laminate film, and the base material film include plastics typified by polyethylene terephthalate (PET), polyethylene naphthalate (PEN), and polyether sulfone (PES); a Synthesis resin such as an acrylic resin; polypropylene; polyester; polyvinyl fluoride; polyvinyl chloride; polyamide; polyimide; an aramid resin; an epoxy resin; an inorganic vapor deposition film; and paper.

For fabrication of the light-emitting device in this embodiment, a vacuum process such as an evaporation method or a solution process such as a spin coating method or an ink-jet method can be used. In the case of using an evaporation method, a physical vapor deposition method (PVD method) such as a sputtering method, an ion plating method, an ion beam evaporation method, a molecular beam evaporation method, or a vacuum evaporation method, a chemical vapor deposition method (CVD method), or the like can be used. Specifically, the functional layers (the hole-injection layers (111, 111a, and 1/1b), the hole-transport layers (112, 112a, and 112b), the light-emitting layers (113, 113a, 113b, and 113c), the electron-transport layers (114, 114a, and 114b), and the electron-injection layers (115, 115a, and 115b)) included in the EL layers and the charge-generation layers (104, 104a, and 104b) of the light-emitting device can be formed by an evaporation method (e.g., a vacuum evaporation method), a coating method (e.g., a dip coating method, a die coating method, a bar coating method, a spin coating method, or a spray coating method), a printing method (e.g., an ink-jet method, a screen printing (stencil) method, an offset printing (planography) method, a flexography (relief printing) method, a gravure printing method, a micro-contact printing method, or a nanoinprinting method), or the like.

Note that materials that can be used for the functional layers (the hole-injection layers (111, 111a, and 1/1b), the hole-transport layers (112, 112a, and 112b), the light-emitting layers (113, 113a, 113b, and 113c), the electron-transport layers (114, 114a, and 114b), and the electron-injection layers (115, 115a, and 115b)) included in the EL layers (103, 103a, and 103b) and the charge-generation layers (104, 104a, and 104b) of the light-emitting device described in this embodiment are not limited to the above materials, and other materials can also be used in combination as long as the functions of the layers are fulfilled. For example, a high molecular compound (e.g., an oligomer, a dendrimer, and a polymer), a middle molecular compound (a compound between a low molecular compound and a high molecular compound with a molecular weight of 400 to 4000), or an inorganic compound (e.g., a quantum dot material) can be used. As the quantum dot material, a colloidal quantum dot material, an alloyed quantum dot material, a core-shell quantum dot material, a core quantum dot material, or the like can be used.

The structure described in this embodiment can be used in an appropriate combination with any of the structures described in the other embodiments.

Embodiment 2

Figure 2A:
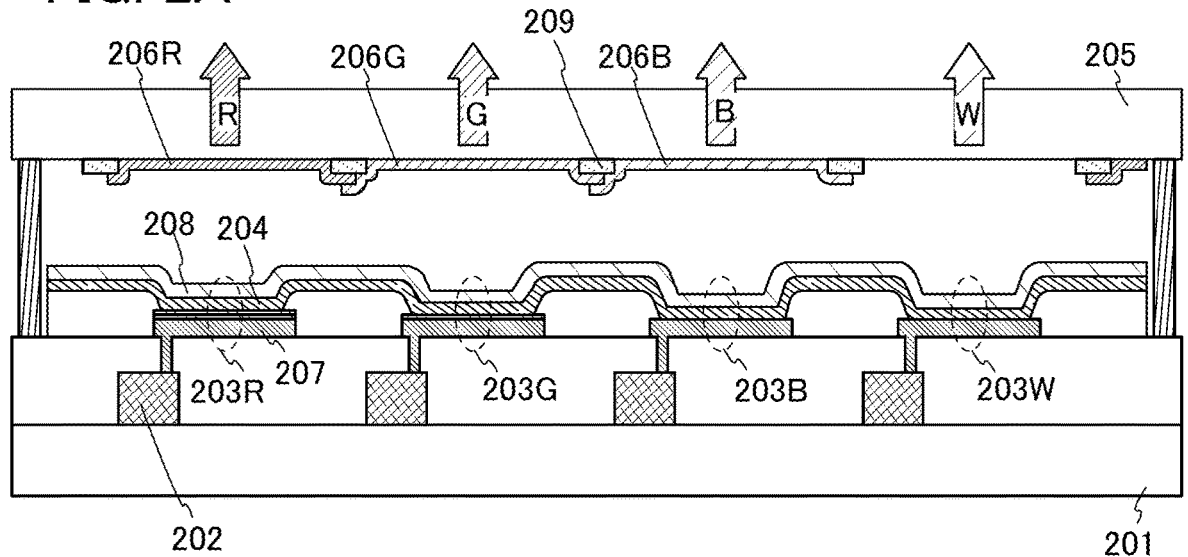
FIGS. 2A-2C are diagrams illustrating light-emitting apparatuses.

In this embodiment, a light-emitting apparatus of one embodiment of the present invention will be described. Note that a light-emitting apparatus illustrated in FIG. 2A is an active-matrix light-emitting apparatus in which transistors (FETs) 202 over a first substrate 201 are electrically connected to light-emitting devices (203R, 203G, 203B, and 203W); the light-emitting devices (203R, 203G, 203B, and 203W) include a common EL layer 204 and each have a microcavity structure in which the optical path length between electrodes of each light-emitting device is adjusted according to the emission color of the light-emitting device. In addition, the light-emitting apparatus is a top-emission light-emitting apparatus in which light is emitted from the EL layer 204 through color filters (206R, 206G, and 206B) formed on a second substrate 205.

In the light-emitting apparatus illustrated in FIG. 2A, a first electrode 207 is formed so as to function as a reflective electrode. A second electrode 208 is formed so as to function as a semi-transmissive and semi-reflective electrode. Note that description in any of the other embodiments can be referred to for electrode materials forming the first electrode 207 and the second electrode 208 and appropriate materials can be used.

Figure 2B:
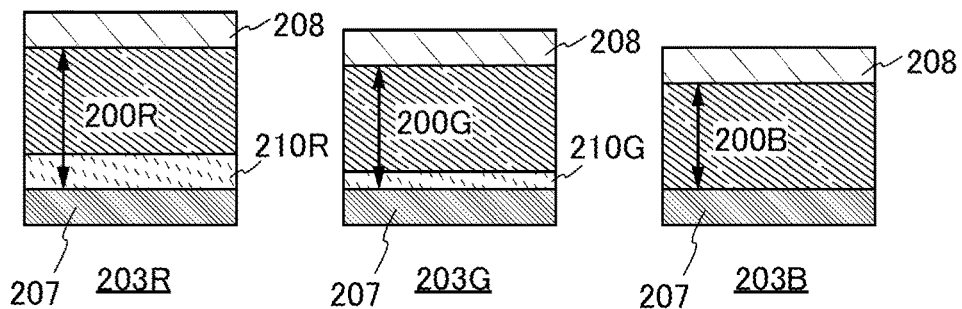

In the case where the light-emitting device 203R is a red-light-emitting device, the light-emitting device 203G is a green-light-emitting device, the light-emitting device 203B is a blue-light-emitting device, and the light-emitting device 203W is a white-light-emitting device in FIG. 2A, for example, a gap between the first electrode 207 and the second electrode 208 in the light-emitting device 203R is adjusted to have an optical path length 200R, a gap between the first electrode 207 and the second electrode 208 in the light-emitting device 203G is adjusted to have an optical path length 200G, and a gap between the first electrode 207 and the second electrode 208 in the light-emitting device 203B is adjusted to have an optical path length 200B as illustrated in FIG. 2B. Note that optical adjustment can be performed in such a manner that a conductive layer 210R is stacked over the first electrode 207 in the light-emitting device 203R and a conductive layer 210G is stacked over the first electrode 207 in the light-emitting device 203G as illustrated in FIG. 2B.

The color filters (206R, 206G, and 206B) are formed on the second substrate 205. Note that the color filters are filters each transmitting visible light in a specific wavelength range and blocking visible light in a specific wavelength range. Thus, as illustrated in FIG. 2A, the color filter 206R that transmits only light in the red wavelength range is provided in a position overlapping with the light-emitting device 203R, whereby red light emission can be obtained from the light-emitting device 203R. The color filter 206G that transmits only light in the green wavelength range is provided in a position overlapping with the light-emitting device 203G, whereby green light emission can be obtained from the light-emitting device 203G. The color filter 206B that transmits only light in the blue wavelength range is provided in a position overlapping with the light-emitting device 203B, whereby blue light emission can be obtained from the light-emitting device 203B. Note that the light-emitting device 203W can emit white light without a color filter. Note that a black layer (black matrix) 209 may be provided at an end portion of one type of color filter. The color filters (206R, 206G, and 206B) and the black layer 209 may be covered with an overcoat layer using a transparent material.

Figure 2C:
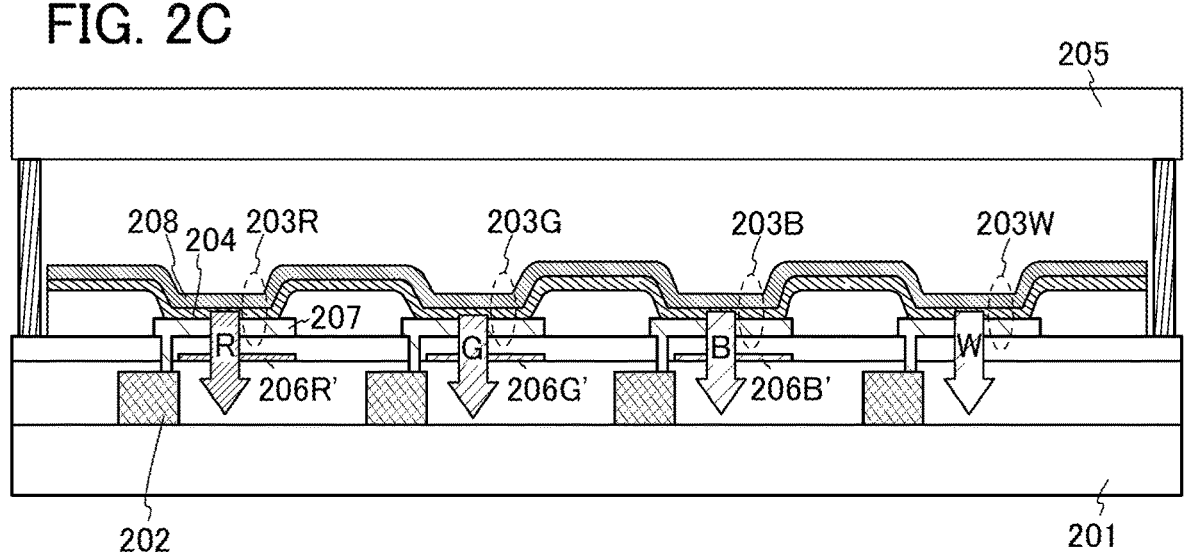

Although the light-emitting device illustrated in FIG. 2A has a structure in which light is extracted from the second substrate 205 side (top emission structure), the light-emitting device may have a structure in which light is extracted from the first substrate 201 side where the FETs 202 are formed (bottom emission structure) as illustrated in FIG. 2C. In the case of a bottom-emission light-emitting device, the first electrode 207 is formed so as to function as a semi-transmissive and semi-reflective electrode and the second electrode 208 is formed so as to function as a reflective electrode. As the first substrate 201, a substrate having at least a light-transmitting property is used. As illustrated in FIG. 2C, color filters (206R', 206G', and 206B') are provided closer to the first substrate 201 than the light-emitting devices (203R, 203G, and 203B) are.

FIG. 2A illustrates the case where the light-emitting devices are the red-light-emitting device, the green-light-emitting device, the blue-light-emitting device, and the white-light-emitting device; however, the light-emitting devices of embodiments of the present invention are not limited to the above structures, and a yellow-light-emitting device or an orange-light-emitting device may be included. Note that description in any of the other embodiments can be referred to for materials that are used for the EL layers (a light-emitting layer, a hole-injection layer, a hole-transport layer, an electron-transport layer, an electron-injection layer, a charge-generation layer, and the like) to fabricate each of the light-emitting devices and appropriate materials can be used. In that case, a color filter needs to be appropriately selected according to the emission color of the light-emitting device.

With the above structure, a light-emitting apparatus including light-emitting devices that exhibit a plurality of emission colors can be obtained.

Note that the structures described in this embodiment can be used in an appropriate combination with any of the structures described in the other embodiments.

Embodiment 3

In this embodiment, a light-emitting apparatus of one embodiment of the present invention will be described.

The use of the device structure of the light-emitting device of one embodiment of the present invention allows fabrication of an active-matrix light-emitting apparatus or a passive-matrix light-emitting apparatus. Note that an active-matrix light-emitting apparatus has a structure including a combination of a light-emitting device and a transistor (FET). Thus, each of a passive-matrix light-emitting apparatus and an active-matrix light-emitting apparatus is included in one embodiment of the present invention. Note that any of the light-emitting devices described in the other embodiments can be used in the light-emitting apparatus described in this embodiment.

In this embodiment, an active-matrix light-emitting apparatus will be described with reference to FIG. 3.

Figure 3A:
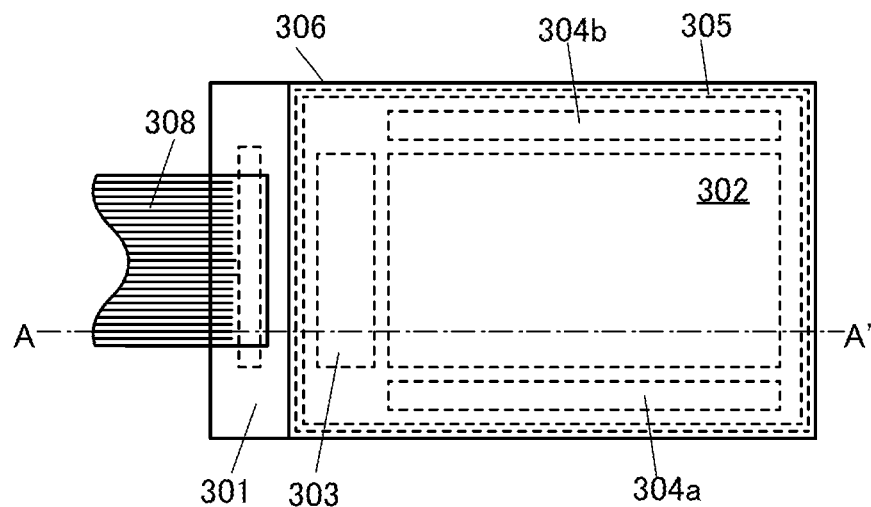
FIGS. 3A and 3B are diagrams illustrating a light-emitting apparatus.
Figure 3B:
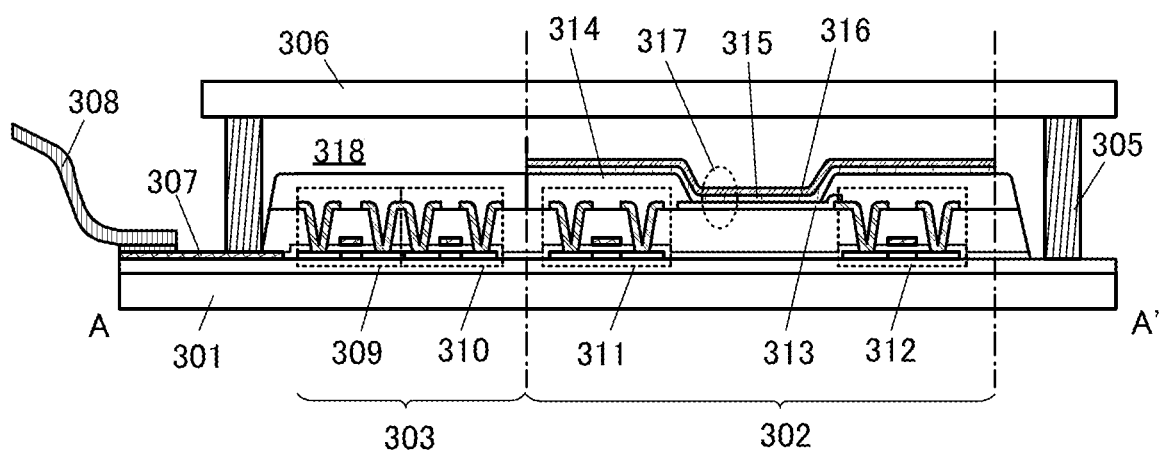

FIG. 3A is a top view illustrating a light-emitting apparatus 21, and FIG. 3B is a cross-sectional view taken along a chain line A-A' in FIG. 3A. The active-matrix light-emitting apparatus includes a pixel portion 302, a driver circuit portion (source line driver circuit) 303, and driver circuit portions (gate line driver circuits) (304a and 304b) that are provided over a first substrate 301. The pixel portion 302 and the driver circuit portions (303, 304a, and 304b) are sealed between the first substrate 301 and a second substrate 306 with a sealant 305.

A lead wiring 307 is provided over the first substrate 301. The lead wiring 307 is electrically connected to an FPC 308 that is an external input terminal. Note that the FPC 308 transmits a signal (e.g., a video signal, a clock signal, a start signal, or a reset signal) or a potential from the outside to the driver circuit portions (303, 304a, and 304b). The FPC 308 may be provided with a printed wiring board (PWB). Note that the light-emitting apparatus provided with an FPC or a PWB is included in the category of a light-emitting apparatus.

Next, FIG. 3B illustrates a cross-sectional structure of the light-emitting apparatus.

The pixel portion 302 is made up of a plurality of pixels each of which includes an FET (switching FET) 311, an FET (current control FET) 312, and a first electrode 313 electrically connected to the FET 312. Note that the number of FETs included in each pixel is not particularly limited and can be set appropriately as needed.

As FETs 309, 310, 311, and 312, for example, a staggered transistor or an inverted staggered transistor can be used without particular limitation. A top-gate transistor, a bottom-gate transistor, or the like may be used.

Note that there is no particular limitation on the crystallinity of a semiconductor that can be used for the FETs 309, 310, 311, and 312, and an amorphous semiconductor or a semiconductor having crystallinity (a microcrystalline semiconductor, a polycrystalline semiconductor, a single crystal semiconductor, or a semiconductor partly including crystal regions) may be used. The use of a semiconductor having crystallinity can suppress deterioration of the transistor characteristics, which is preferable.

For these semiconductors, a Group 14 element, a compound semiconductor, an oxide semiconductor, an organic semiconductor, or the like can be used, for example. Typically, a semiconductor containing silicon, a semiconductor containing gallium arsenide, an oxide semiconductor containing indium, or the like can be used.

The driver circuit portion 303 includes the FET 309 and the FET 310. The FET 309 and the FET 310 may be formed with a circuit including transistors having the same conductivity type (either n-channel transistors or p-channel transistors) or a CMOS circuit including an n-channel transistor and a p-channel transistor. Furthermore, a structure including a driver circuit outside may be employed.

An end portion of the first electrode 313 is covered with an insulator 314. For the insulator 314, an organic compound such as a negative photosensitive resin or a positive photosensitive resin (acrylic resin), or an inorganic compound such as silicon oxide, silicon oxynitride, or silicon nitride can be used. An upper end portion or a lower end portion of the insulator 314 preferably has a curved surface with curvature. In that case, favorable coverage with a film formed over the insulator 314 can be obtained.

An EL layer 315 and a second electrode 316 are stacked over the first electrode 313. The EL layer 315 includes a light-emitting layer, a hole-injection layer, a hole-transport layer, an electron-transport layer, an electron-injection layer, a charge-generation layer, and the like.

The structure and materials described in any of the other embodiments can be used for the structure of a light-emitting device 317 described in this embodiment. Although not illustrated here, the second electrode 316 is electrically connected to the FPC 308 that is an external input terminal.

Although the cross-sectional view illustrated in FIG. 3B illustrates only one light-emitting device 317, a plurality of light-emitting devices are arranged in a matrix in the pixel portion 302. Light-emitting devices from which light of three kinds of colors (R, G, and B) are obtained are selectively formed in the pixel portion 302, whereby a light-emitting apparatus capable of full-color display can be formed. In addition to the light-emitting devices from which light of three kinds of colors (R, G, and B) are obtained, for example, light-emitting devices from which light of white (W), yellow (Y), magenta (M), cyan (C), and the like are obtained may be formed. For example, the light-emitting devices from which light of some of the above colors are obtained are added to the light-emitting devices from which light of three kinds of colors (R, G, and B) are obtained, whereby effects such as an improvement in color purity and a reduction in power consumption can be obtained. Alternatively, a light-emitting apparatus capable of full-color display may be fabricated by a combination with color filters. As the kinds of color filters, red (R), green (G), blue (B), cyan (C), magenta (M), yellow (Y), and the like can be used.

When the second substrate 306 and the first substrate 301 are bonded to each other with the sealant 305, the FETs (309, 310, 311, and 312) and the light-emitting device 317 over the first substrate 301 are provided in a space 318 surrounded by the first substrate 301, the second substrate 306, and the sealant 305. Note that the space 318 may be filled with an inert gas (e.g., nitrogen or argon) or an organic substance (including the sealant 305).

An epoxy resin or glass frit can be used for the sealant 305. It is preferable to use a material that is permeable to as little moisture and oxygen as possible for the sealant 305. As the second substrate 306, a material that can be used as the first substrate 301 can be similarly used. Thus, any of the various substrates described in the other embodiments can be appropriately used. As the substrate, a glass substrate, a quartz substrate, or a plastic substrate made of FRP (Fiber-Reinforced Plastics), PVF (polyvinyl fluoride), polyester, an acrylic resin, or the like can be used. In the case where glass frit is used for the sealant, the first substrate 301 and the second substrate 306 are preferably glass substrates in terms of adhesion.

In the above manner, the active-matrix light-emitting apparatus can be obtained.

In the case where the active-matrix light-emitting apparatus is formed over a flexible substrate, the FETs and the light-emitting device may be directly formed over the flexible substrate; alternatively, the FETs and the light-emitting device may be formed over a substrate provided with a separation layer and then separated at the separation layer by application of heat, force, laser irradiation, or the like to be transferred to a flexible substrate. For the separation layer, a stack including inorganic films such as a tungsten film and a silicon oxide film, or an organic resin film of polyimide or the like can be used, for example. Examples of the flexible substrate include, in addition to a substrate over which a transistor can be formed, a paper substrate, a cellophane substrate, an aramid film substrate, a polyimide film substrate, a cloth substrate (including a natural fiber (e.g., silk, cotton, or hemp), a synthetic fiber (e.g., nylon, polyurethane, or polyester), a regenerated fiber (e.g., acetate, cupro, rayon, or regenerated polyester), or the like), a leather substrate, and a rubber substrate. With the use of any of these substrates, high durability, high heat resistance, a reduction in weight, and a reduction in thickness can be achieved.

The light-emitting device included in the active-matrix light-emitting apparatus may be driven with a structure in which pulsed light (with a frequency of kHz or MHz, for example) emitted from the light-emitting device is used for display. The light-emitting device formed using any of the above organic compounds has excellent frequency characteristics; thus, time for driving the light-emitting device can be shortened, and thus the power consumption can be reduced. Furthermore, a reduction in driving time leads to inhibition of heat generation, so that the degree of deterioration of the light-emitting device can be reduced.

Note that the structures described in this embodiment can be used in an appropriate combination with the structures described in the other embodiments.

Embodiment 4

In this embodiment, examples of a variety of electronic devices and an automobile completed using the light-emitting device of one embodiment of the present invention or a light-emitting apparatus including the light-emitting device of one embodiment of the present invention are described. Note that the light-emitting apparatus can be used mainly in a display portion of the electronic device described in this embodiment.

Figure 4A:
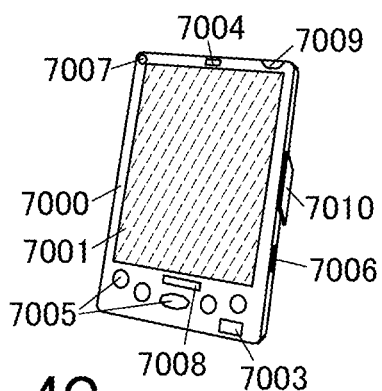
FIGS. 4A-4G are diagrams each illustrating an electronic device.
Figure 4B:
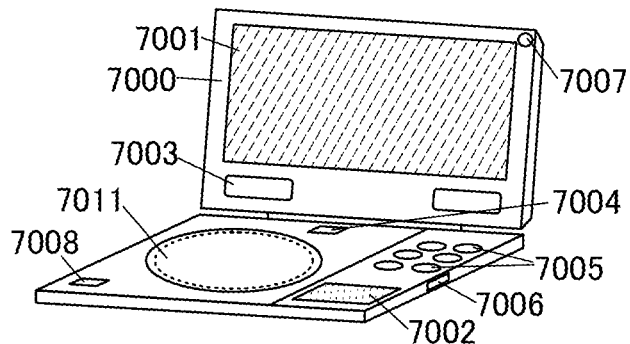
Figure 4C:
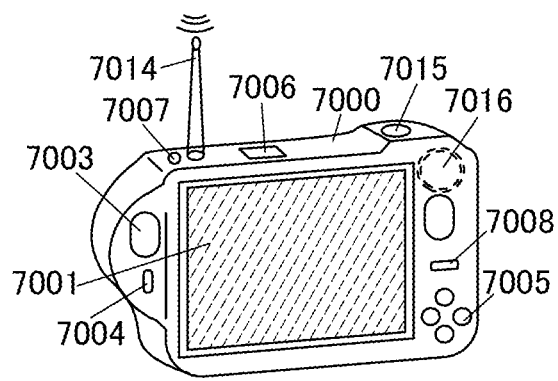

Electronic devices illustrated in FIG. 4A to FIG. 4C can include a housing 7000, a display portion 7001, a speaker 7003, an LED lamp 7004, operation keys 7005 (including a power switch or an operation switch), a connection terminal 7006, a sensor 7007 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), a microphone 7008, and the like.

FIG. 4A is a mobile computer which can include a switch 7009, an infrared port 7010, and the like in addition to the above components.

FIG. 4B is a portable image reproducing device (e.g., a DVD player) which is provided with a recording medium and can include a second display portion 7002, a recording medium reading portion 7011, and the like in addition to the above components.

FIG. 4C is a digital camera with a television reception function, which can include an antenna 7014, a shutter button 7015, an image receiving portion 7016, and the like in addition to the above components.

Figure 4D:
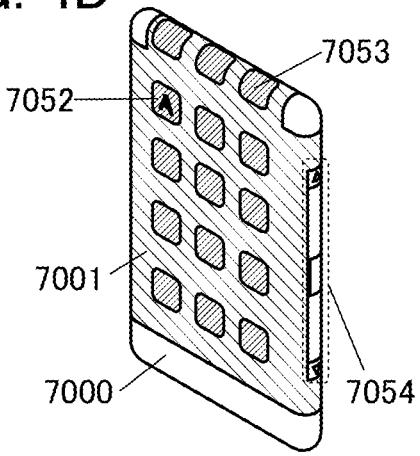

FIG. 4D is a portable information terminal. The portable information terminal has a function of displaying information on three or more surfaces of the display portion 7001. Here, an example in which information 7052, information 7053, and information 7054 are displayed on different surfaces is shown. For example, the user can check the information 7053 displayed in a position that can be observed from above the portable information terminal, with the portable information terminal put in a breast pocket of his/her clothes. The user can see the display without taking out the portable information terminal from the pocket and decide whether to answer the call, for example.

Figure 4E:
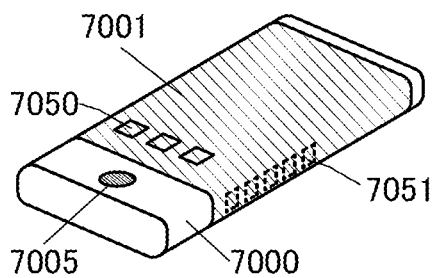

FIG. 4E is a portable information terminal (e.g., a smartphone) and can include the display portion 7001, the operation key 7005, and the like in the housing 7000. Note that a speaker, a connection terminal, a sensor, or the like may be provided in the portable information terminal. The portable information terminal can display characters and image information on its plurality of surfaces. Here, an example is shown in which three icons 7050 are displayed.

Information 7051 indicated by dashed rectangles can be displayed on another surface of the display portion 7001. Examples of the information 7051 include notification of reception of an e-mail, SNS, or an incoming call, the title and sender of an e-mail, SNS, or the like, the date, the time, remaining battery, and the reception strength of an antenna. Alternatively, the icon 7050 or the like may be displayed in the position where the information 7051 is displayed.

Figure 4F:
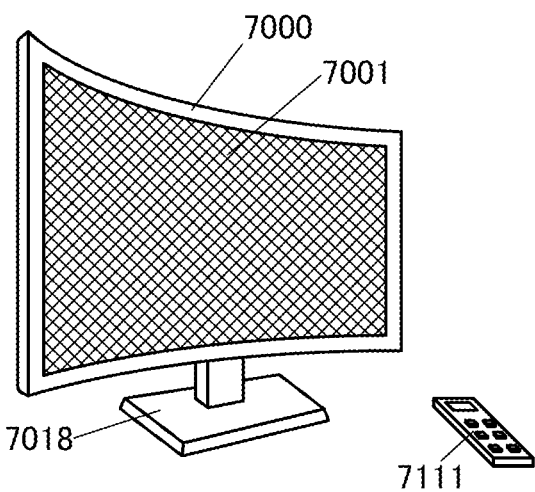

FIG. 4F is a large-size television set (also referred to as TV or a television receiver), which can include the housing 7000, the display portion 7001, and the like. In addition, shown here is a structure where the housing 7000 is supported by a stand 7018. The television set can be operated with a separate remote controller 7111 or the like. Note that the display portion 7001 may include a touch sensor, in which case the television set may be operated by touch on the display portion 7001 with a finger or the like. The remote controller 7111 may include a display portion for displaying data output from the remote controller 7111. With operation keys or a touch panel provided in the remote controller 7111, channels and volume can be operated and images displayed on the display portion 7001 can be operated.

The electronic devices illustrated in FIG. 4A to FIG. 4F can have a variety of functions. For example, they can have a function of displaying a variety of data (e.g., a still image, a moving image, and a text image) on the display portion, a touch panel function, a function of displaying a calendar, date, time, or the like, a function of controlling processing with a variety of software (programs), a wireless communication function, a function of being connected to a variety of computer networks with a wireless communication function, a function of transmitting and receiving a variety of data with a wireless communication function, and a function of reading out a program or data stored in a recording medium and displaying it on the display portion. Furthermore, the electronic device including a plurality of display portions can have a function of displaying image data mainly on one display portion while displaying text data mainly on the other display portion, a function of displaying a three-dimensional image by displaying images on a plurality of display portions with a parallax taken into account, or the like. Furthermore, the electronic device including an image receiving portion can have a function of taking a still image, a function of taking a moving image, a function of automatically or manually correcting a taken image, a function of storing a taken image in a recording medium (external or incorporated in the camera), a function of displaying a taken image on the display portion, or the like. Note that functions that the electronic devices illustrated in FIG. 4A to FIG. 4F can have are not limited to those, and the electronic devices can have a variety of functions.

Figure 4G:
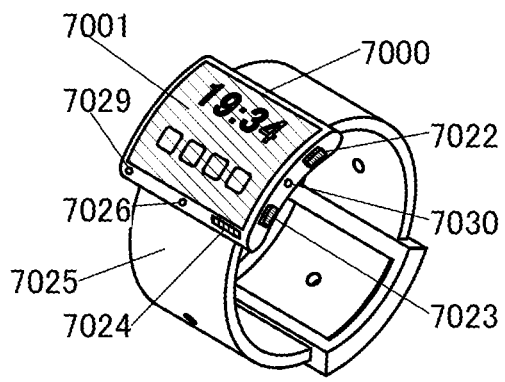

FIG. 4G is a watch-type portable information terminal, which can be used as a smart watch, for example. The watch-type portable information terminal includes the housing 7000, the display portion 7001, operation buttons 7022 and 7023, a connection terminal 7024, a band 7025, a microphone 7026, a sensor 7029, a speaker 7030, and the like. The display surface of the display portion 7001 is curved, and display can be performed along the curved display surface. Furthermore, the portable information terminal enables hands-free calling by mutually communicating with, for example, a headset capable of wireless communication. With the connection terminal 7024, the portable information terminal can perform mutual data transmission with another information terminal and charging. Wireless power feeding can also be employed for the charging operation.

The display portion 7001 mounted in the housing 7000 also serving as a bezel includes a non-rectangular display region. The display portion 7001 can display an icon 7027 indicating time, another icon 7028, and the like. The display portion 7001 may be a touch panel (input/output device) including a touch sensor (input device).

Note that the smart watch illustrated in FIG. 4G can have a variety of functions. For example, the smart watch can have a function of displaying a variety of data (e.g., a still image, a moving image, and a text image) on the display portion, a touch panel function, a function of displaying a calendar, date, time, or the like, a function of controlling processing with a variety of software (programs), a wireless communication function, a function of being connected to a variety of computer networks with a wireless communication function, a function of transmitting and receiving a variety of data with a wireless communication function, and a function of reading out a program or data stored in a recording medium and displaying it on the display portion.

Moreover, a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like can be included inside the housing 7000.

Note that the light-emitting apparatus of one embodiment of the present invention can be used in the display portions of the electronic devices described in this embodiment, enabling the electronic devices to have a long lifetime.

Figure 5A:
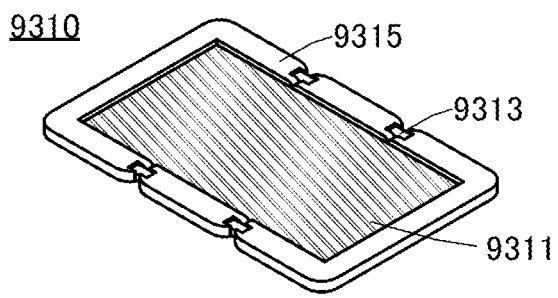
FIGS. 5A-5C are diagrams illustrating an electronic device.
Figure 5B:
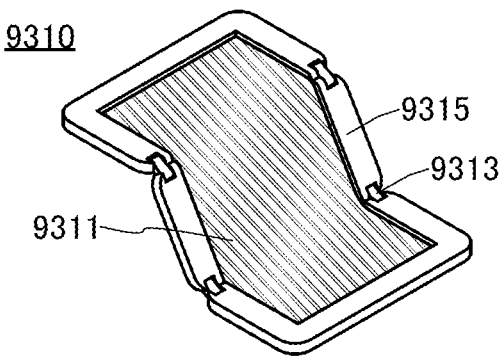
Figure 5C:
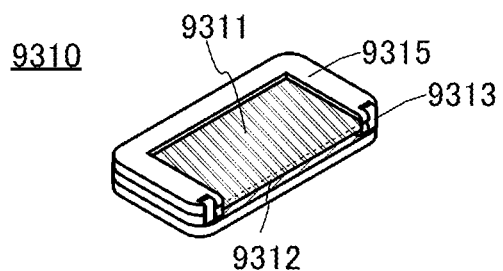

Another electronic device including the light-emitting apparatus is a foldable portable information terminal illustrated in FIGS. 5A to 5C. FIG. 5A illustrates a portable information terminal 9310 which is opened. FIG. 5B illustrates the portable information terminal 9310 in a state in the middle of change from one of an opened state and a folded state to the other. FIG. 5C illustrates the portable information terminal 9310 which is folded. The portable information terminal 9310 is excellent in portability when folded, and is excellent in display browsability when opened because of a seamless large display region.

A display portion 9311 is supported by three housings 9315 joined together by hinges 9313. Note that the display portion 9311 may be a touch panel (input/output device) including a touch sensor (input device). By bending the display portion 9311 at a portion between two housings 9315 with the use of the hinges 9313, the portable information terminal 9310 can be reversibly changed in shape from an opened state to a folded state. The light-emitting apparatus of one embodiment of the present invention can be used for the display portion 9311. In addition, an electronic device having a long lifetime can be achieved. A display region 9312 in the display portion 9311 is a display region that is positioned at a side surface of the portable information terminal 9310 which is folded. On the display region 9312, information icons, file shortcuts of frequently used applications or programs, and the like can be displayed, and confirmation of information and start of an application can be smoothly performed.

Figure 6A:
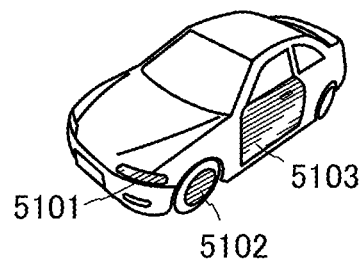
FIGS. 6A and 6B are diagrams illustrating an automobile.
Figure 6B:
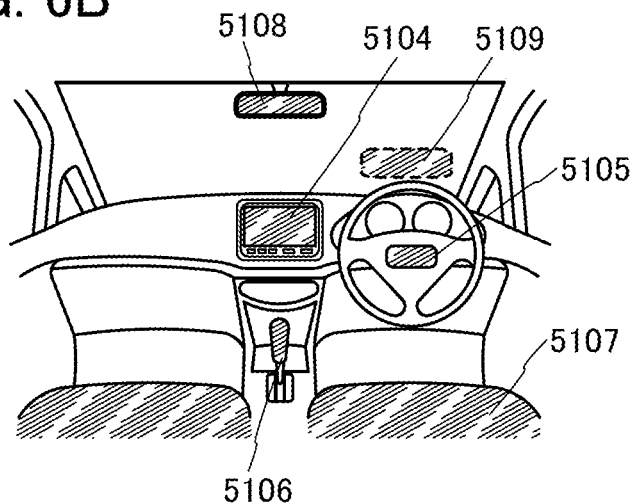

FIGS. 6A and 6B illustrate an automobile including the light-emitting apparatus. In other words, the light-emitting apparatus can be integrated into an automobile. Specifically, the light-emitting apparatus can be applied to lights 5101 (including lights of the rear part of the automobile), a wheel 5102, a part or the whole of a door 5103, or the like on the outer side of the automobile which is illustrated in FIG. 6A. The light-emitting apparatus can also be applied to a display portion 5104, a steering wheel 5105, a shifter 5106, a seat 5107, an inner rearview mirror 5108, a windshield 5109, or the like on the inner side of the automobile which is illustrated in FIG. 6B. The light-emitting apparatus may be used for part of any of the other glass windows.

In the above manner, the electronic devices and automobiles in which the light-emitting apparatus of one embodiment of the present invention is used can be obtained. In that case, an electronic device having a long lifetime can be achieved. In addition, the light-emitting apparatus can be used for electronic devices and automobiles in a variety of fields without being limited to those described in this embodiment.

Note that the structures described in this embodiment can be used in an appropriate combination with any of the structures described in the other embodiments.

Embodiment 5

In this embodiment, the structure of a lighting device fabricated using the light-emitting apparatus of one embodiment of the present invention or the light-emitting device which is part of the light-emitting apparatus will be described with reference to FIG. 7.

Figure 7A:
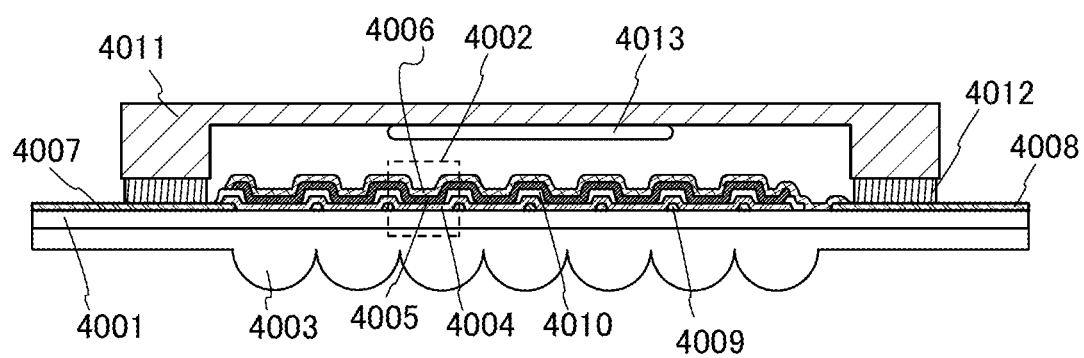
FIGS. 7A and 7B are diagrams each illustrating a lighting device.
Figure 7B:
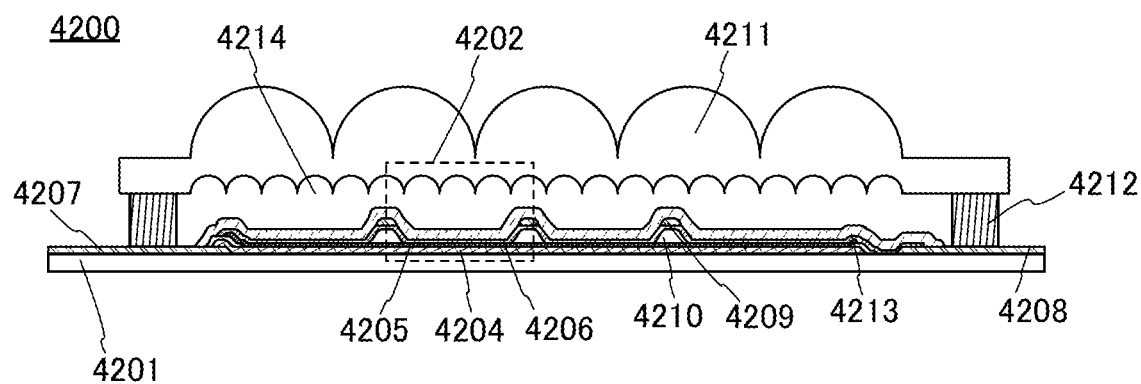

FIGS. 7A and 7B each show an example of a cross-sectional view of a lighting device. FIG. 7A is a bottom-emission lighting device in which light is extracted from the substrate side, and FIG. 7B is a top-emission lighting device in which light is extracted from the sealing substrate side.

A lighting device 4000 illustrated in FIG. 7A includes a light-emitting device 4002 over a substrate 4001. In addition, the lighting device 4000 includes a substrate 4003 with unevenness on the outside of the substrate 4001. The light-emitting device 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other with a sealant 4012. A desiccant 4013 is preferably provided between the sealing substrate 4011 and the light-emitting device 4002. The substrate 4003 has the unevenness illustrated in FIG. 7A, whereby the extraction efficiency of light generated in the light-emitting device 4002 can be increased.

A lighting device 4200 illustrated in FIG. 7B includes a light-emitting device 4202 over a substrate 4201. The light-emitting device 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may also be provided. In addition, an insulating layer 4210 may be provided under the auxiliary wiring 4209.

The substrate 4201 and a sealing substrate 4211 with unevenness are bonded to each other with a sealant 4212. A barrier film 4213 and a planarization film 4214 may be provided between the sealing substrate 4211 and the light-emitting device 4202. The sealing substrate 4211 has the unevenness illustrated in FIG. 7B, whereby the extraction efficiency of light generated in the light-emitting device 4202 can be increased.

Application examples of such lighting devices include a ceiling light for indoor lighting. Examples of the ceiling light include a ceiling direct mount light and a ceiling embedded light. Such a lighting device is fabricated using the light-emitting apparatus in combination with a housing or a cover.

For another example, such lighting devices can be used for a foot light that illuminates a floor so that the safety of one's feet can be improved. For example, the foot light can be effectively used in a bedroom, on a staircase, or on a passage. In that case, the size or shape of the foot light can be changed depending on the area or structure of a room. The foot light can be a stationary lighting device fabricated using the light-emitting apparatus in combination with a support base.

Such lighting devices can also be used for a sheet-like lighting device (sheet-like lighting). The sheet-like lighting, which is attached to a wall when used, is space-saving and thus can be used for a wide variety of uses. Furthermore, the area of the sheet-like lighting can be easily increased. The sheet-like lighting can also be used on a wall or housing having a curved surface.

Besides the above examples, the light-emitting apparatus which is one embodiment of the present invention or the light-emitting device which is a part of the light-emitting apparatus can be used as part of furniture in a room, so that a lighting device which has a function of the furniture can be obtained.

As described above, a variety of lighting devices that include the light-emitting apparatus can be obtained. Note that these lighting devices are also included in embodiments of the present invention.

The structure described in this embodiment can be used in an appropriate combination with any of the structures described in the other embodiments.

Example 1

In this example, three kinds of light-emitting devices having different stacked-layer structures of an EL layer 902, including the light-emitting device of one embodiment of the present invention, are fabricated and the obtained device characteristics are shown. Note that a light-emitting device 1 fabricated in this example has a structure in which an electron-transport layer 914 formed using an electron-transport material and an electron-injection layer 915 formed using an alkali metal compound are stacked between a light-emitting layer 913 and a second electrode 903. A light-emitting device 2 includes, between the light-emitting layer 913 and the second electrode 903, the electron-transport layer 914 formed using an alkali metal and an organic compound having a structure in which an aromatic ring is fused to a furan ring of a furodiazine skeleton, which is used for the light-emitting layer 913. A comparative light-emitting device 3 includes, between the light-emitting layer 913 and the second electrode 903, a three-layer structure: the electron-transport layer 914 having a two-layer structure and an electron-injection layer 915.

Figure 8:
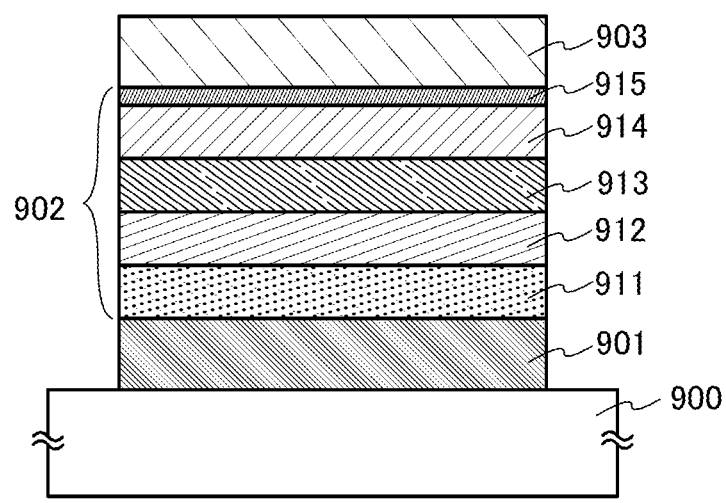
FIG. 8 is a diagram illustrating a light-emitting device.
Figure 9:
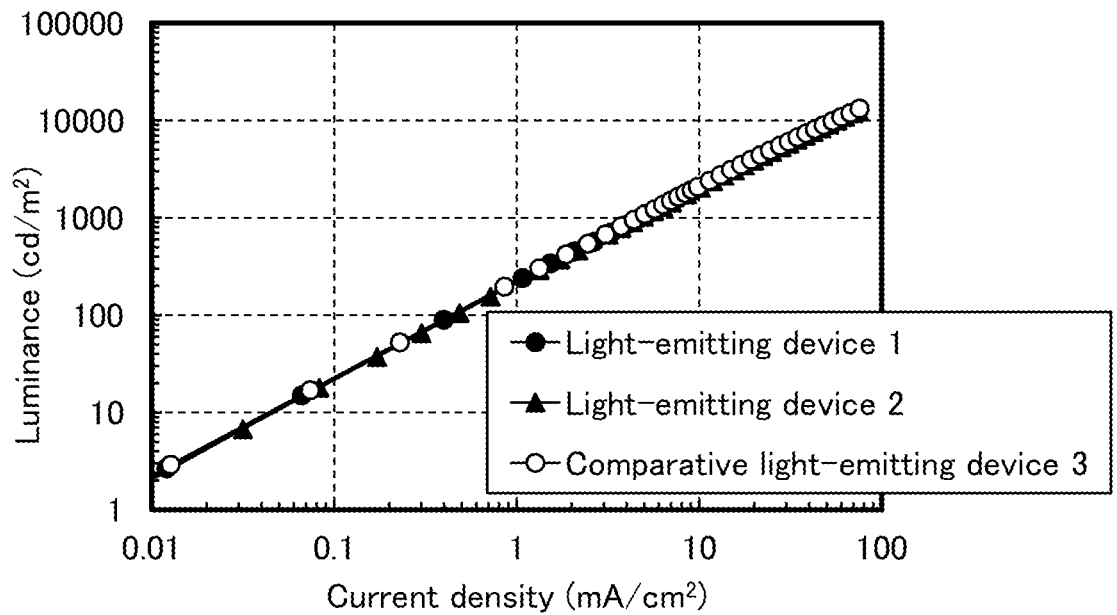
FIG. 9 is a diagram showing luminance-current density characteristics of a light-emitting device 1, a light-emitting device 2, and a comparative light-emitting device 3.
Figure 10:
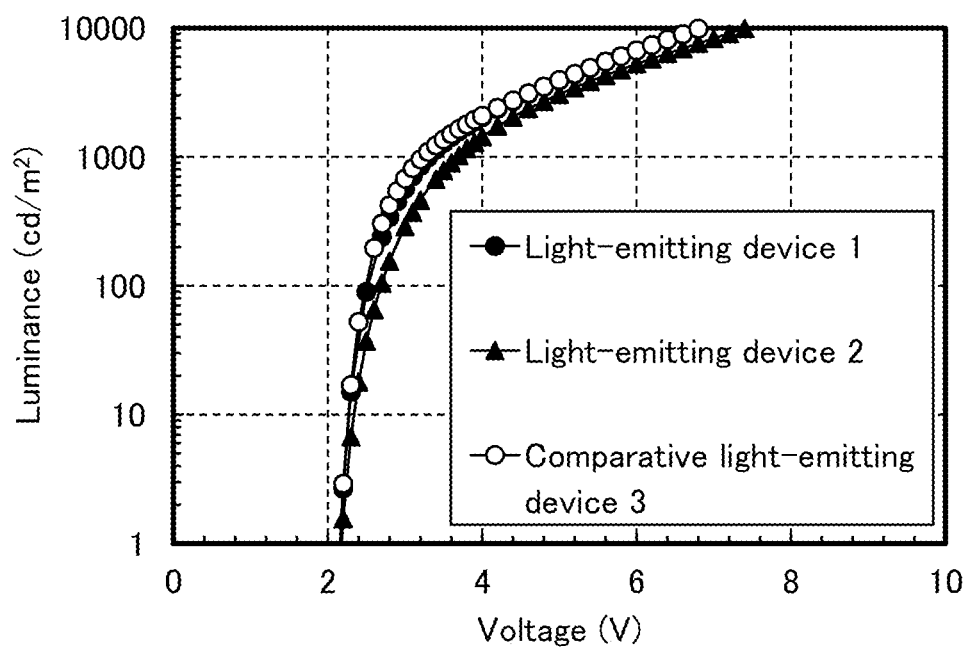
FIG. 10 is a diagram showing luminance-voltage characteristics of the light-emitting device 1, the light-emitting device 2, and the comparative light-emitting device 3.
Figure 11:
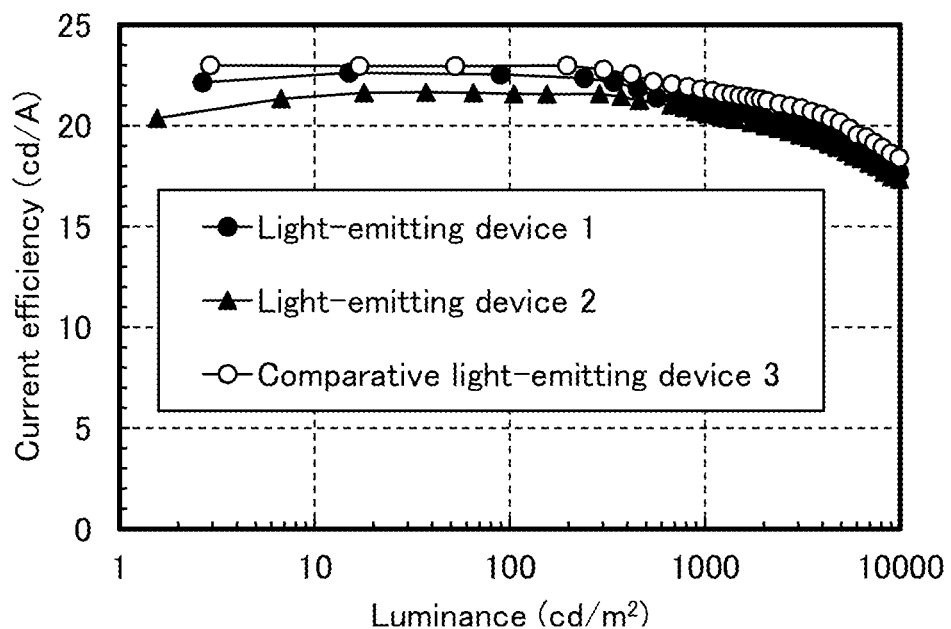
FIG. 11 is a diagram showing current efficiency-luminance characteristics of the light-emitting device 1, the light-emitting device 2, and the comparative light-emitting device 3.
Figure 12:
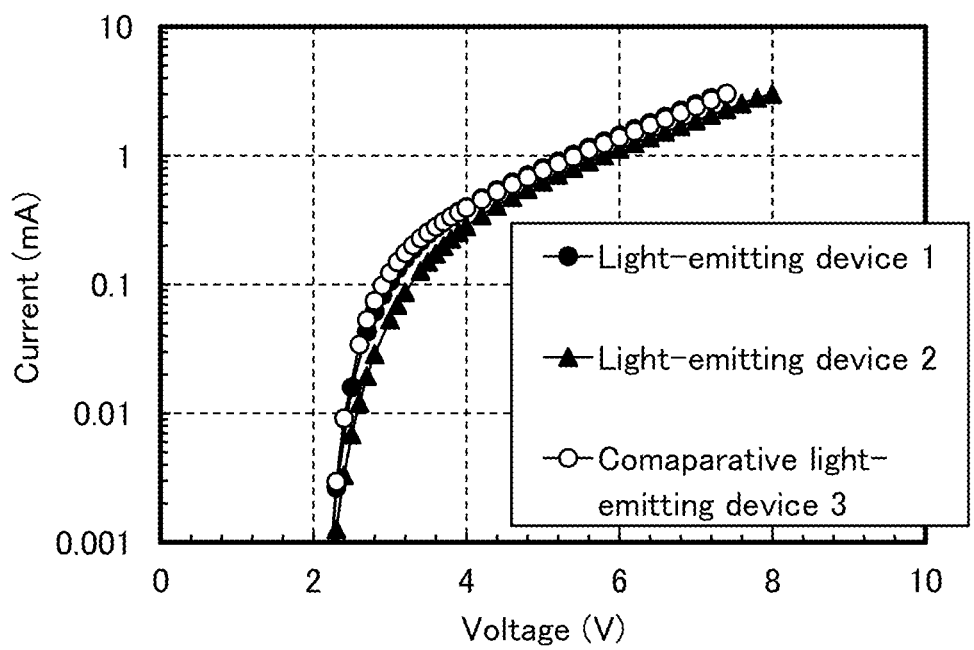
FIG. 12 is a diagram showing current-voltage characteristics of the light-emitting device 1, the light-emitting device 2, and the comparative light-emitting device 3.

Specific device structures and fabrication methods of the above light-emitting devices will be described below. Note that FIG. 8 illustrates a device structure of the light-emitting devices described in this example, and Table 1 shows specific structures. Chemical formulae of materials used in this example are shown below.

[Chemical Formula 10]

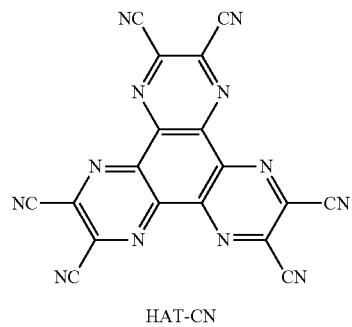

HAT-CN

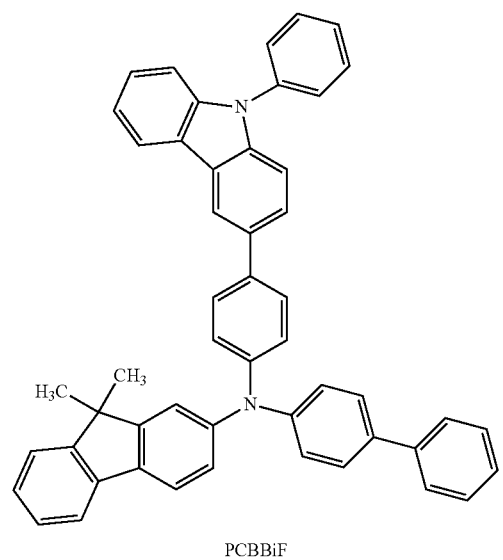

PCBBiF

TABLE 1

| | First electrode 901 | Hole-injection layer 911 | Hole-transport layer 912 | Light-emitting layer 913 | Electron-transport layer 914 | | Electron-injection layer 915 | Second electrode 903 |
|---|---|---|---|---|---|---|---|---|
| Light-emitting device 1 | ITSO (70 nm) | HAT-CN (5 nm) | PCBBiF (70 nm) | * (70 nm) | — | NBphen (15 nm) | LiF (1 nm) | Al (200 nm) |
| Light-emitting device 2 | ITSO (70 nm) | HAT-CN (5 nm) | PCBBiF (70 nm) | ** (80 nm) | 9mDBtBPNfpr:Liq (1:1 5 nm) | | — | Al (200 nm) |
| Comparative light-emitting device 3 | ITSO (70 nm) | HAT-CN (5 nm) | PCBBiF (70 nm) | *** (40 nm) | 9mDBtBPNfpr 30 nm | NBphen (15 nm) | LiF (1 nm) | Al (200 nm) |

* 9mDBtBPNfpr: PCBBiF: [Ir(dmpqn)$_2$(acac)] (0.7:0.3:0.1)
** 9mDBtBPNfpr: PCBBiF: [Ir(dmpqn)$_2$(acac)] (0.8:0.2:0.1)
*** 9mDBtBPNfpr: PCBBiF: [Ir(dmpqn)$_2$(acac)] (0.75:0.25:0.1)

-continued

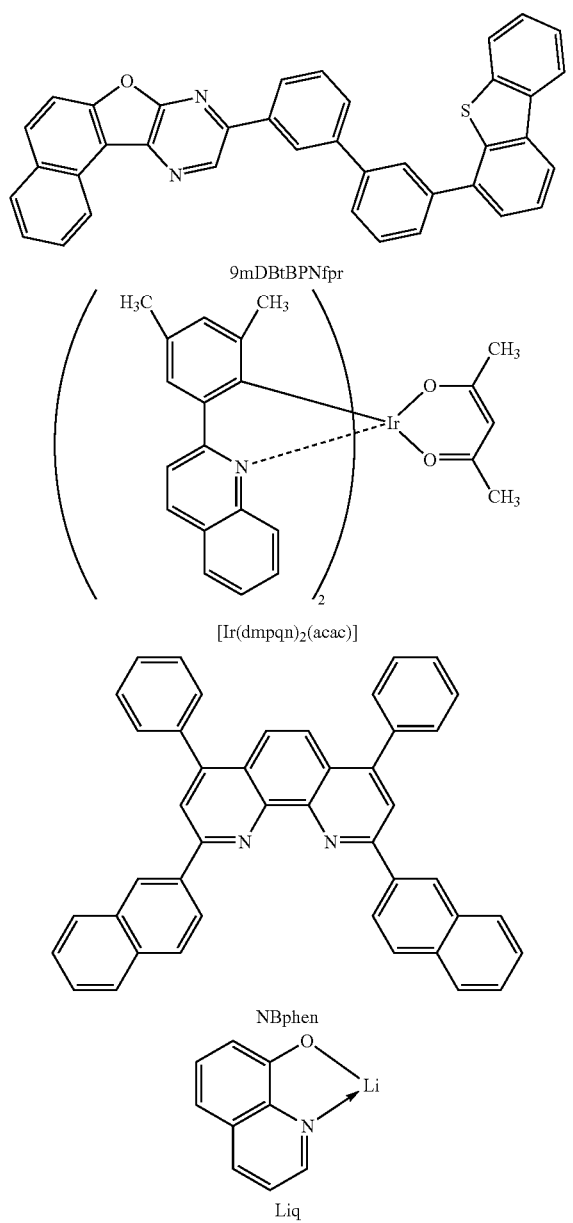

<<Fabrication of Light-Emitting Devices>>
<Fabrication of Light-Emitting Device 1, Light-Emitting Device 2, and Comparative Light-Emitting Device 3>

The light-emitting devices described in this example each have a structure, as illustrated in FIG. 8, in which a hole-injection layer 911, a hole-transport layer 912, the light-emitting layer 913, the electron-transport layer 914, and the electron-injection layer 915 are stacked in this order over a first electrode 901 formed over a substrate 900, and the second electrode 903 is stacked over the electron-injection layer 915.

First, the first electrode 901 was formed over the substrate 900. The electrode area was set to 4 mm² (2 mm×2 mm). A glass substrate was used as the substrate 900. The first electrode 901 was formed by deposition of indium tin oxide containing silicon oxide (ITSO) by a sputtering method to a thickness of 70 nm.

As pretreatment, a surface of the substrate was washed with water, baking was performed at 200° C. for one hour, and then UV ozone treatment was performed for 370 seconds. After that, the substrate was transferred into a vacuum evaporation apparatus in which the pressure was reduced to approximately $10^{-4}$ Pa, vacuum baking at 170° C. for 30 minutes was performed in a heating chamber in the vacuum evaporation apparatus, and then the substrate was cooled down for approximately 30 minutes.

Next, the hole-injection layer 911 was formed over the first electrode 901. The hole-injection layer 911 was formed by evaporation using HAT-CN to a thickness of 5 nm.

Then, the hole-transport layer 912 was formed over the hole-injection layer 911. The hole-transport layer 912 was formed by evaporation using N-(1,1'-biphenyl-4-yl)-N-[4-(9-phenyl-9H-carbazol-3-yl)phenyl]-9,9-dimethyl-9H-fluoren-2-amine (abbreviation: PCBBiF) to a thickness of 70 nm.

Next, the light-emitting layer 913 was formed over the hole-transport layer 912.

In the case of the light-emitting device 1, the light-emitting layer 913 was formed by co-evaporation using bis[4,6-dimethyl-2-(2-quinolinyl-κN)phenyl-κC](2,4-pentanedionato-κ²O,O')iridium(III) (abbreviation: [Ir(dmpqn)₂(acac)]) as a guest material (a phosphorescent material) in addition to 9-[3'-(dibenzothiophen-4-yl)bipheny-3-yl]naphtho[1',2':4,5]furo[2,3-b]pyrazine (abbreviation: 9mDBtBPNfpr) and PCBBiF so that a weight ratio was 9mDBtBPNfpr: PCBBiF: [Ir(dmpqn)₂(acac)]=0.7:0.3:0.1. The thickness was set to 70 nm.

In the case of the light-emitting device 2, co-evaporation was performed using materials similar to those for the light-emitting device 1 so that the weight ratio was 9mDBtBPNfpr: PCBBiF: [Ir(dmpqn)₂(acac)]=0.8:0.2:0.1. The thickness was set to 80 nm.

In the case of the comparative light-emitting device 3, co-evaporation was performed using a material similar to that for the light-emitting device 1 so that the weight ratio was 9mDBtBPNfpr: PCBBiF: [Ir(dmpqn)₂(acac)]=0.75:0.25:0.1. The thickness was set to 40 nm.

Next, the electron-transport layer 914 was formed over the light-emitting layer 913.

In the case of the light-emitting device 1, the electron-transport layer 914 was formed to a thickness of 15 nm by evaporation using 2,9-bis(naphthalen-2-yl)-4,7-diphenyl-1,10-phenanthroline (abbreviation: NBphen) that is an electron-transport material. In the case of the light-emitting device 2, co-evaporation was performed using 8-quinolinolato-lithium (abbreviation: Liq) and 9mDBtBPNfpr that was the same electron-transport material as that used for the light-emitting layer 913 so that the weight ratio was 9mDBtBPNfpr: Liq=1:1. The thickness was set to 5 nm. In the case of the comparative light-emitting device 3, evaporation was performed using 9mDBtBPNfpr that was the same electron-transport material as that used for the light-emitting layer 913 so that the thickness was 30 nm, and then evaporation was performed using NBphen that was an electron-transport material so that the thickness was 15 nm.

Then, the electron-injection layer 915 was formed over the electron-transport layer 914. Note that the electron-injection layer 915 was formed only in the light-emitting device 1 and the comparative light-emitting device 3. The electron-injection layer 915 was formed by evaporation using lithium fluoride (LiF) to a thickness of 1 nm.

After that, the second electrode 903 was formed over the electron-injection layer 915. The second electrode 903 was formed by an evaporation method using aluminum to a thickness of 200 nm. In this example, the second electrode 903 functions as a cathode.

Through the above steps, the light-emitting devices in each of which an EL layer was sandwiched between a pair of electrodes over the substrate 900 were formed. The hole-injection layer 911, the hole-transport layer 912, the light-emitting layer 913, the electron-transport layer 914, and the electron-injection layer 915 described in the above steps are functional layers forming the EL layer in one embodiment of the present invention. Furthermore, in all the evaporation steps in the above fabrication method, an evaporation method by a resistance-heating method was used.

The light-emitting devices fabricated as described above were sealed using another substrate (not illustrated). At the time of the sealing using the another substrate (not illustrated), the another substrate (not illustrated) on which a sealant that solidifies by ultraviolet light was applied was fixed onto the substrate 900 in a glove box containing a nitrogen atmosphere, and the substrates were bonded to each other such that the sealant attached to the periphery of the light-emitting device formed over the substrate 900. At the time of the sealing, the sealant was irradiated with 365-nm ultraviolet light at 6 J/cm$^2$ to be solidified, and the sealant was subjected to heat treatment at 80° C. for one hour to be stabilized.

<<Operation Characteristics of Light-Emitting Devices>>

Operation characteristics of each of the fabricated light-emitting devices were measured. Note that the measurement was carried out at room temperature (an atmosphere maintained at 25° C.). The results are shown in FIG. 9 to FIG. 12.

Figure 14:
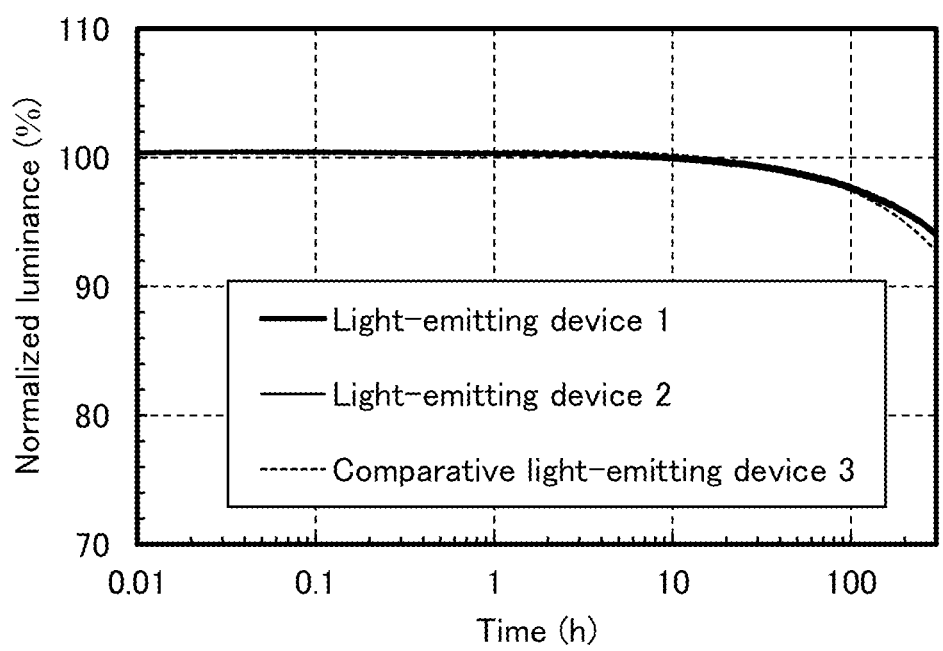
FIG. 14 is a diagram showing reliability of the light-emitting device 1, the light-emitting device 2, and the comparative light-emitting device 3.

Table 2 below shows initial values of main characteristics of the light-emitting devices at around 1000 cd/m$^2$.

reliability tests. In FIG. 14, the vertical axis represents normalized luminance (%) with an initial luminance of 100%, and the horizontal axis represents driving time (h) of the device. As the reliability tests, constant current driving tests where a constant current was supplied at a current density of 75 mA/cm$^2$ were performed.

The results of the reliability tests show that the light-emitting device 1 and the light-emitting device 2 have no significant difference from the comparative light-emitting device 3.

The comparative light-emitting device 3 has a structure with improved reliability by having, between the light-emitting layer 913 and the second electrode 903, a stacked-layer structure of three layers: the electron-transport layer 914 in which a first layer containing 9mDBtBPNfpr used as a host material in the light-emitting layer 913 and a second layer containing NBphen are stacked, and the electron-injection layer 915 formed using LiF; whereas the light-emitting device 1 has a two-layer structure in which the electron-transport layer 914 formed using only NBphen and the electron-injection layer 915 formed using LiF are stacked. The light-emitting device 2 has a single-layer structure between the light-emitting layer 913 and the second electrode 903 with only the electron-transport layer 914 formed using a mixed film of Liq and 9mDBtBPNfpr that is used as the host material in the light-emitting layer 913.

The light-emitting devices fabricated in this example are each characterized in that an electron-transport organic compound having a structure in which an aromatic ring is fused to a furan ring of a furodiazine skeleton is used as a host material in the light-emitting layer 913.

The results described in this example show that, although the light-emitting device 1, the light-emitting device 2, and

TABLE 2

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting device 1 | 3.3 | 0.19 | 4.7 | (0.68, 0.32) | 990 | 21 | 20 | 22 |
| Light-emitting device 2 | 3.7 | 0.20 | 5.0 | (0.68, 0.32) | 1000 | 21 | 17 | 22 |
| Comparative light-emitting device 3 | 3.2 | 0.18 | 4.4 | (0.68, 0.32) | 950 | 22 | 21 | 23 |

The above results show that there is no significant difference in initial characteristics between the light-emitting devices described in this example despite their different device structures (e.g., stacked-layer structures and thicknesses).

Figure 13:
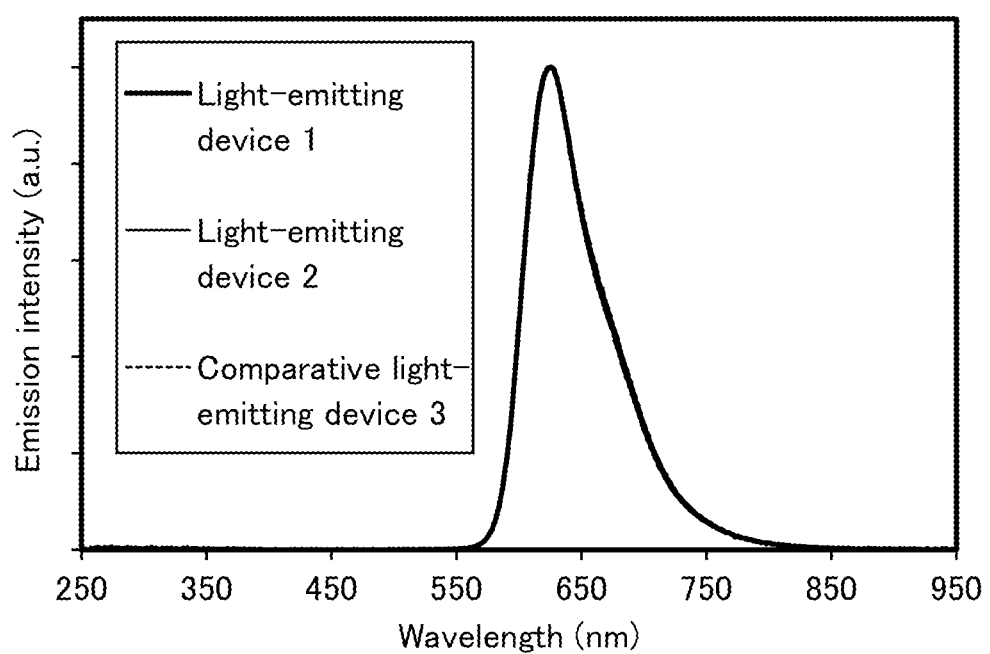
FIG. 13 is a diagram showing emission spectra of the light-emitting device 1, the light-emitting device 2, and the comparative light-emitting device 3.

FIG. 13 shows emission spectra when current at a current density of 2.5 mA/cm$^2$ was applied to the light-emitting device 1, the light-emitting device 2, and the comparative light-emitting device 3. As shown in FIG. 13, the emission spectra of the light-emitting device 1, the light-emitting device 2, and the comparative light-emitting device 3 each have a peak at around 624 nm, indicating that the peak is derived from light emission of [Ir(dmpqn)$_2$(acac)] contained in the light-emitting layer 913.

Next, reliability tests were performed on the light-emitting device 1, the light-emitting device 2, and the comparative light-emitting device 3. FIG. 14 shows the results of the the comparative light-emitting device 3 have different stacked-layer structure, reliability similar to that of the comparative light-emitting device 3 with a larger number of stacked layers can be obtained. Thus, the light-emitting device 1 and the light-emitting device 2 can each be fabricated through simpler process than the comparative light-emitting device 3. Furthermore, thickness adjustment in optical design can be performed with the light-emitting layer 913, so that a light-emitting device that does not easily deteriorate can be provided by increasing the thickness of the light-emitting layer 913.

Reference Synthesis Example 1

A synthesis method of 9-[(3'-dibenzothiophen-4-yl)biphenyl-3-yl]naphtho[1',2':4,5]furo[2,3-b]pyrazine (abbreviation: 9mDBtBPNfpr), which is the organic compound used in this example and represented by Structural Formula (100), is described. The structure of 9mDBtBPNfpr is shown below.

[Chemical Formula 11]

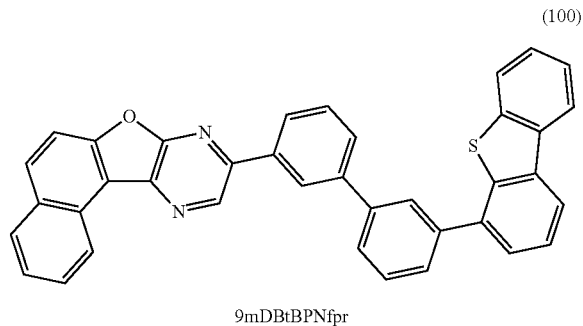

9mDBtBPNfpr

Step 1; Synthesis of 6-chloro-3-(2-methoxynaphthalen-1-yl)pyrazin-2-amine

First, into a three-neck flask equipped with a reflux pipe were put 4.37 g of 3-bromo-6-chloropyrazin-2-amine, 4.23 g of 2-methoxynaphthalene-1-boronic acid, 4.14 g of potassium fluoride, and 75 mL of dehydrated tetrahydrofuran, and the air in the flask was replaced with nitrogen. The mixture in the flask was degassed by being stirred under reduced pressure, 0.57 g of tris(dibenzylideneacetone)dipalladium (0) (abbreviation: Pd$_2$(dba)$_3$) and 4.5 mL of tri-tert-butylphosphine (abbreviation: P(tBu)$_3$) were added thereto, and then stirring was performed at 80° C. for 54 hours for reaction.

After a predetermined time elapsed, the obtained mixture was subjected to suction filtration and the filtrate was concentrated. Then, purification by silica gel column chromatography using a developing solvent of toluene: ethyl acetate=9:1 was performed, whereby a target pyrazine derivative was obtained (yellowish white powder, 2.19 g, in a yield of 36%). The synthesis scheme of Step 1 is shown in Formula (a-1) below.

[Chemical Formula 12]

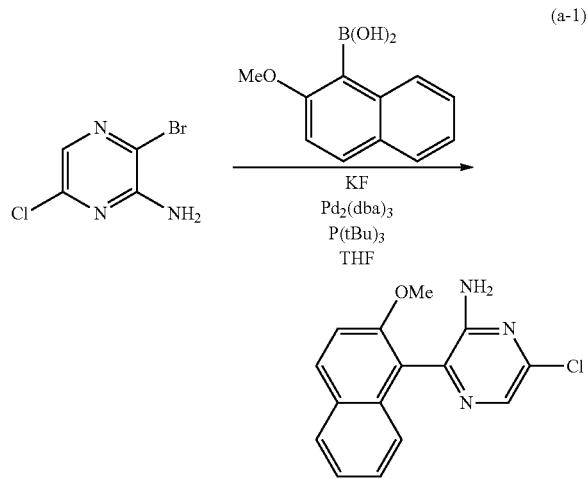

Step 2; Synthesis of 9-chloronaphtho[1',2':4,5]furo [2,3-b]pyrazine

Next, into a three-neck flask were put 2.18 g of 6-chloro-3-(2-methoxynaphthalen-1-yl)pyrazin-2-amine obtained in Step 1, 63 mL of dehydrated tetrahydrofuran, and 84 mL of a glacial acetic acid, and the air in the flask was replaced with nitrogen. After the flask was cooled down to −10° C., 2.8 mL of tert-butyl nitrite was dripped, and stirring was performed at −10° C. for 30 minutes and at 0° C. for 3 hours. After a predetermined time elapsed, 250 mL of water was added to the obtained suspension and suction filtration was performed, whereby a target pyrazine derivative was obtained (yellowish white powder, 1.48 g, in a yield of 77%). The synthesis scheme of Step 2 is shown in (a-2) below.

[Chemical Formula 13]

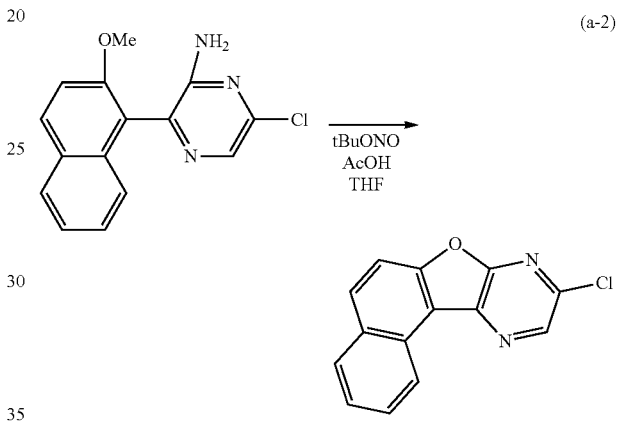

Step 3; Synthesis of 9-[(3'-dibenzothiophene-4-yl) biphenyl-3-yl]naphtho[1',2':4,5]furo[2,3-b]pyrazine (abbreviation: 9mDBtBPNfpr)

Into a three-neck flask were put 1.48 g of 9-chloronaphtho[1',2':4,5]furo[2,3-b]pyrazine obtained in Step 2, 3.41 g of 3'-(4-dibenzothiophene)-1,1'-biphenyl-3-boronic acid, 8.8 mL of a 2M aqueous solution of potassium carbonate, 100 mL of toluene, and 10 mL of ethanol, and the air in the flask was replaced with nitrogen. The mixture in the flask was degassed by being stirred under reduced pressure, 0.84 g of bis(triphenylphosphine)palladium(II) dichloride (abbreviation: Pd(PPh$_3$)$_2$Cl$_2$) was added thereto, and then stirring was performed at 80° C. for 18 hours for reaction.

After a predetermined time elapsed, the obtained suspension was subjected to suction filtration, followed by washing with water and ethanol. The obtained solid was dissolved in toluene, and the mixture was filtered through a filter aid in which Celite, alumina, and Celite were stacked in this order and was recrystallized with a mixed solvent of toluene and hexane, whereby a target substance was obtained (a pale yellow solid, 2.66 g, in a yield of 82%).

By a train sublimation method, 2.64 g of the obtained pale yellow solid was purified by sublimation. The conditions of the purification by sublimation were such that the solid was heated under a pressure of 2.6 Pa at 315° C. while the argon gas flowed at a flow rate of 15 mL/min. After the purification by sublimation, 2.34 g of a target pale yellow solid was obtained in a yield of 89%. The synthesis scheme of Step 3 is shown in (a-3) below.

[Chemical Formula 14]

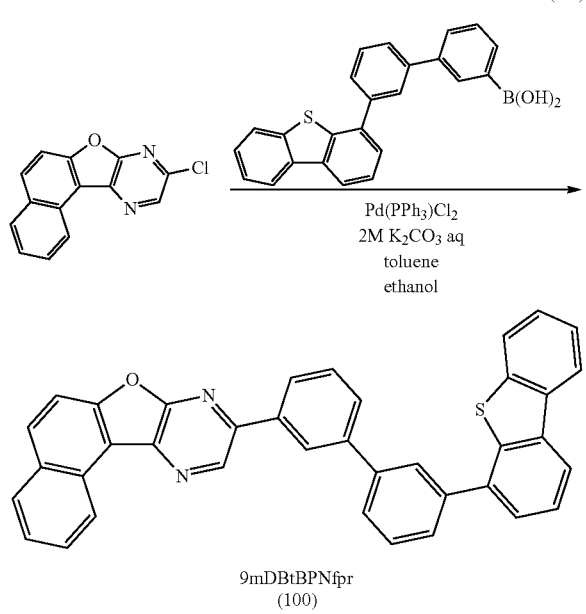

9mDBtBPNfpr
(100)

Results of analysis by nuclear magnetic resonance ($^1$H-NMR) spectroscopy of the pale yellow solid obtained in Step 3 are shown below.

$^1$H-NMR. δ (CD$_2$Cl$_2$): 7.47-7.51 (m, 2H), 7.60-7.69 (m, 5H), 7.79-7.89 (m, 6H), 8.05 (d, 1H), 8.10-8.11 (m, 2H), 8.18-8.23 (m, 3H), 8.53 (s, 1H), 9.16 (d, 1H), 9.32 (s, 1H).

Reference Synthesis Example 2

A synthesis method of 9-(9'-phenyl-3,3'-bi-9H-carbazol-9-yl)naphtho[1',2':4,5]furo[2,3-b]pyrazine (abbreviation: 9PCCzNfpr), which is the organic compound represented by Structural Formula (101) in Embodiment 1, is described. The structure of 9PCCzNfpr is shown below.

[Chemical Formula 15]

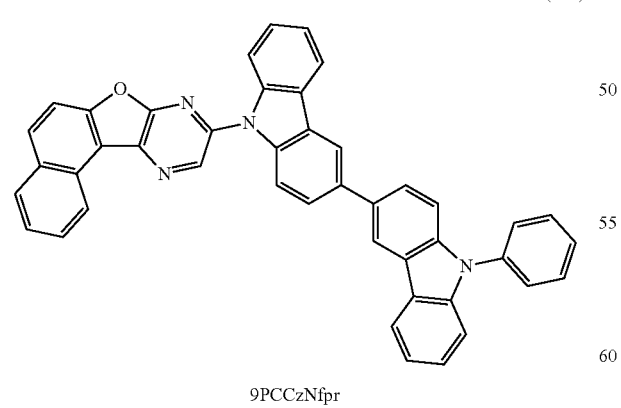

9PCCzNfpr
(101)

Into a three-neck flask were put 0.94 g of 9-chloronaphtho[1',2':4,5]furo[2,3-b]pyrazine whose synthesis method is described in Step 2 in Reference Synthesis Example 1, 1.69 g of 9'-phenyl-3,3'-bi-9H-carbazole, and 37 mL of mesitylene, and the air in the flask was replaced with nitrogen. The mixture in the flask was degassed by being stirred under reduced pressure, 1.23 g of sodium tert-butoxide, 0.021 g of tris(dibenzylideneacetone)dipalladium(0) (abbreviation: Pd$_2$(dba)$_3$), and 0.030 g of 2-dicyclohexylphosphino-2',6'-dimethoxybiphenyl (abbreviation: S-Phos) were added thereto, and then stirring was performed at 120° C. for 8 hours for reaction.

After a predetermined time elapsed, the obtained suspension was subjected to suction filtration, followed by washing with water and ethanol. The obtained solid was dissolved in toluene, and the mixture was filtered through a filter aid in which Celite, alumina, and Celite were stacked in this order and was recrystallized with a mixed solvent of toluene and hexane, whereby a target substance was obtained (a yellow solid, 0.85 g, in a yield of 36%).

By a train sublimation method, 0.84 g of the obtained yellow solid was purified by sublimation. The conditions of the purification by sublimation were such that the solid was heated under a pressure of 2.5 Pa at 350° C. while the argon gas flowed at a flow rate of 10 mL/min. After the purification by sublimation, 0.64 g of a target yellow solid was obtained in a yield of 76%. The synthesis scheme of the above synthesis method is shown in (b-1) below.

[Chemical Formula 16]

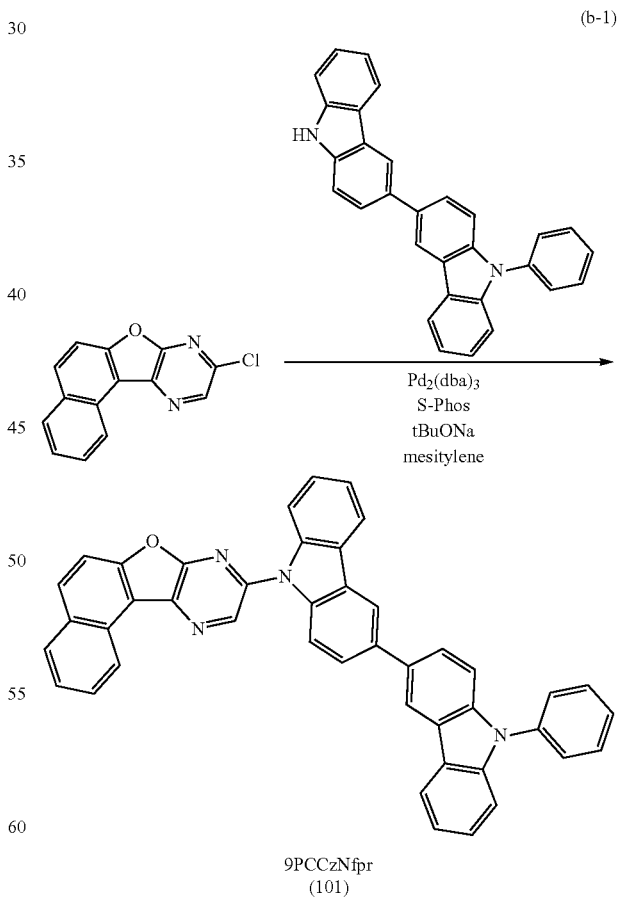

9PCCzNfpr
(101)

Results of analysis by nuclear magnetic resonance ($^1$H-NMR) spectroscopy of the yellow solid obtained by the above synthesis method are shown below.

¹H-NMR. δ (CDCl₃): 7.32-7.35 (m, 1H), 7.42-7.57 (m, 6H), 7.63-7.70 (m, 5H), 7.80-7.90 (m, 4H), 8.09 (d, 2H), 8.14 (d, 2H), 8.27 (d, 2H), 8.49 (d, 2H), 9.20 (d, 1H), 9.27 (s, 1H).

Reference Synthesis Example 3

A synthesis method of 9-[3-(9'-phenyl-3,3'-bi-9H-carbazol-9-yl)phenyl]naphtho[1',2':4,5]furo[2,3-b]pyrazine (abbreviation: 9mPCCzPNfpr), which is the organic compound represented by Structural Formula (102) in Embodiment 1, is described. The structure of 9mPCCzPNfpr is shown below.

[Chemical Formula 17]

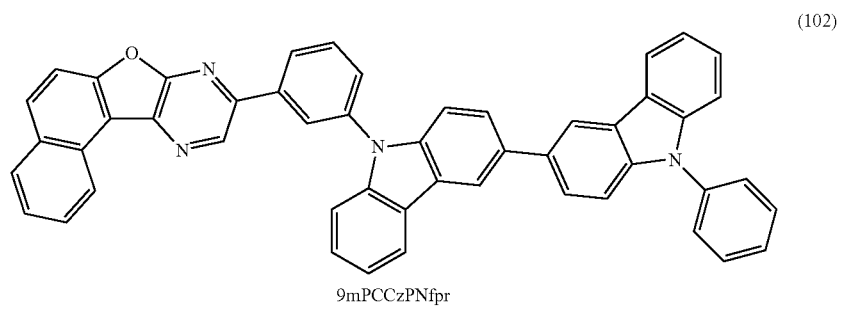

9mPCCzPNfpr
(102)

[Chemical Formula 18]

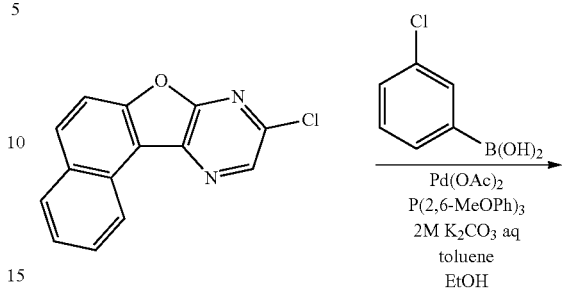

(c-1)

Step 1; Synthesis of 9-(3-chlorophenyl)naphtho[1',2':4,5]furo[2,3-b]pyrazine

Into a three-neck flask were put 2.12 g of 9-chloronaphtho[1',2':4,5]furo[2,3-b]pyrazine whose synthesis method is described in Step 2 in Reference Synthesis Example 1, 1.41 g of 3-chlorophenylboronic acid, 14 mL of a 2M aqueous solution of potassium carbonate, 83 mL of toluene, and 8.3 mL of ethanol, and the air in the flask was replaced with nitrogen. The mixture in the flask was degassed by being stirred under reduced pressure, 0.19 g of palladium(II) acetate (abbreviation: Pd(OAc)₂) and 1.12 g of tris(2,6-dimethoxyphenyl)phosphine (abbreviation: P(2,6-MeOPh)₃) were added thereto, and then stirring was performed at 90° C. for 7.5 hours for reaction.

After a predetermined time elapsed, the obtained mixture was subjected to suction filtration, followed by washing with ethanol. Then, purification by silica gel column chromatography using toluene as a developing solvent was performed, whereby a target pyrazine derivative was obtained (yellowish white powder, 1.97 g, in a yield of 73%). The synthesis scheme of Step 1 is shown in Formula (c-1) below.

-continued

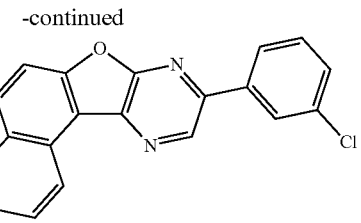

Step 2; Synthesis of 9mPCCzPNfpr

Next, into a three-neck flask were put 1.45 g of 9-(3-chlorophenyl)naphtho[1',2':4,5]furo[2,3-b]pyrazine obtained in Step 1, 1.82 g of 9'-phenyl-3,3'-bi-9H-carbazole, and 22 mL of mesitylene, and the air in the flask was replaced with nitrogen. The mixture in the flask was degassed by being stirred under reduced pressure, 0.85 g of sodium tert-butoxide, 0.025 g of tris(dibenzylideneacetone)dipalladium(0) (abbreviation: Pd₂(dba)₃), and 0.036 g of 2-dicyclohexylphosphino-2',6'-dimethoxybiphenyl (abbreviation: S-Phos) were added thereto, and then stirring was performed at 150° C. for 7 hours for reaction.

After a predetermined time elapsed, the obtained suspension was subjected to suction filtration, followed by washing with water and ethanol. The obtained solid was dissolved in toluene, and the mixture was filtered through a filter aid in which Celite, alumina, and Celite were stacked in this order and was recrystallized with a mixed solvent of toluene and hexane, whereby a target substance was obtained (a yellow solid, 2.22 g, in a yield of 71%).

By a train sublimation method, 2.16 g of the obtained yellow solid was purified by sublimation. The conditions of the purification by sublimation were such that the solid was heated under a pressure of 2.6 Pa at 385° C. while the argon gas flowed at a flow rate of 18 mL/min. After the purification by sublimation, 1.67 g of a target yellow solid was obtained in a yield of 77%. The synthesis scheme of Step 2 is shown in Formula (c-2) below.

Results of analysis by nuclear magnetic resonance ($^1$H-NMR) spectroscopy of the yellow solid obtained in Step 2 are shown below.

$^1$H-NMR. δ (CD$_2$Cl$_2$): 7.31-7.39 (m, 2H), 7.43-7.59 (m, 6H), 7.64-7.69 (m, 6H), 7.78-7.88 (m, 6H), 8.09 (d, 1H), 8.15 (d, 1H), 8.26 (d, 1H), 8.30 (d, 1H), 8.34 (d, 1H), 8.51-8.55 (m, 3H), 9.15 (d, 1H), 9.35 (s, 1H).

Reference Synthesis Example 4

A synthesis method of 9-[3-(9'-phenyl-2,3'-bi-9H-carbazol-9-yl)phenyl]naphtho[1',2':4,5]furo[2,3-b]pyrazine (abbreviation: 9mPCCzPNfpr-02), which is the organic compound represented by Structural Formula (103) in

[Chemical Formula 19]

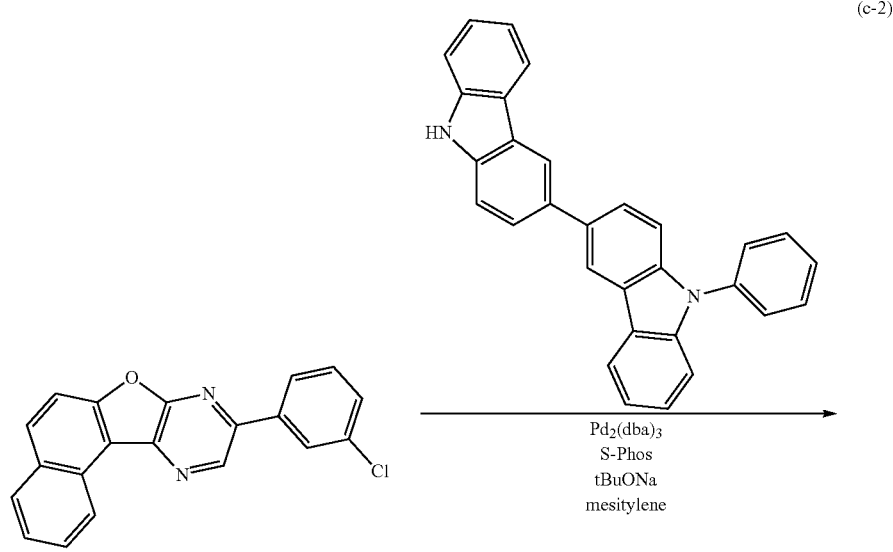

(c-2)

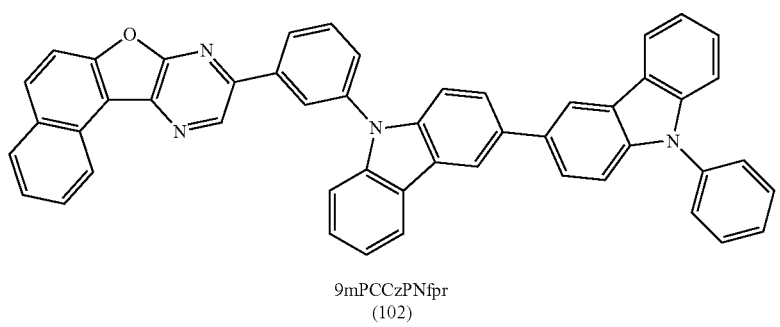

9mPCCzPNfpr
(102)

Embodiment 1, is described. The structure of 9mPCCzPNfpr-02 is shown below.

[Chemical Formula 20]

(103)

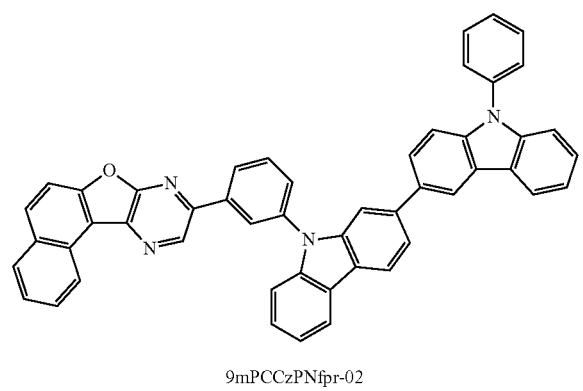

9mPCCzPNfpr-02

Into a three-neck flask were put 1.19 g of 9-chloronaphtho[1',2':4,5]furo[2,3-b]pyrazine whose synthesis method is described in Step 2 in Reference Synthesis Example 1, 3.51 g of 3-(9'-phenyl-2,3'-bi-9H-carbazol-9-yl)phenylboronic acid pinacol ester, 6.0 mL of a 2M aqueous solution of potassium carbonate, 60 mL of toluene, and 6 mL of ethanol, and the air in the flask was replaced with nitrogen. The mixture in the flask was degassed by being stirred under reduced pressure, 0.33 g of bis(triphenylphosphine)palladium(II) dichloride (abbreviation: Pd(PPh$_3$)$_2$Cl$_2$) was added thereto, and then stirring was performed at 90° C. for 16 hours for reaction.

After a predetermined time elapsed, the obtained suspension was subjected to suction filtration, followed by washing with water and ethanol. The obtained solid was dissolved in toluene, and the mixture was filtered through a filter aid in which Celite, alumina, and Celite were stacked in this order and was recrystallized with a mixed solvent of toluene and hexane, whereby a target substance was obtained (a yellow solid, 3.01 g, in a yield of 90%).

By a train sublimation method, 3.00 g of the obtained yellow solid was purified by sublimation. The conditions of the purification by sublimation were such that the solid was heated under a pressure of 2.7 Pa at 380° C. while the argon gas flowed at a flow rate of 16 mL/min. After the purification by sublimation, 2.47 g of a target yellow solid was obtained in a yield of 82%. The synthesis scheme is shown in Formula (d-1) below.

[Chemical Formula 21]

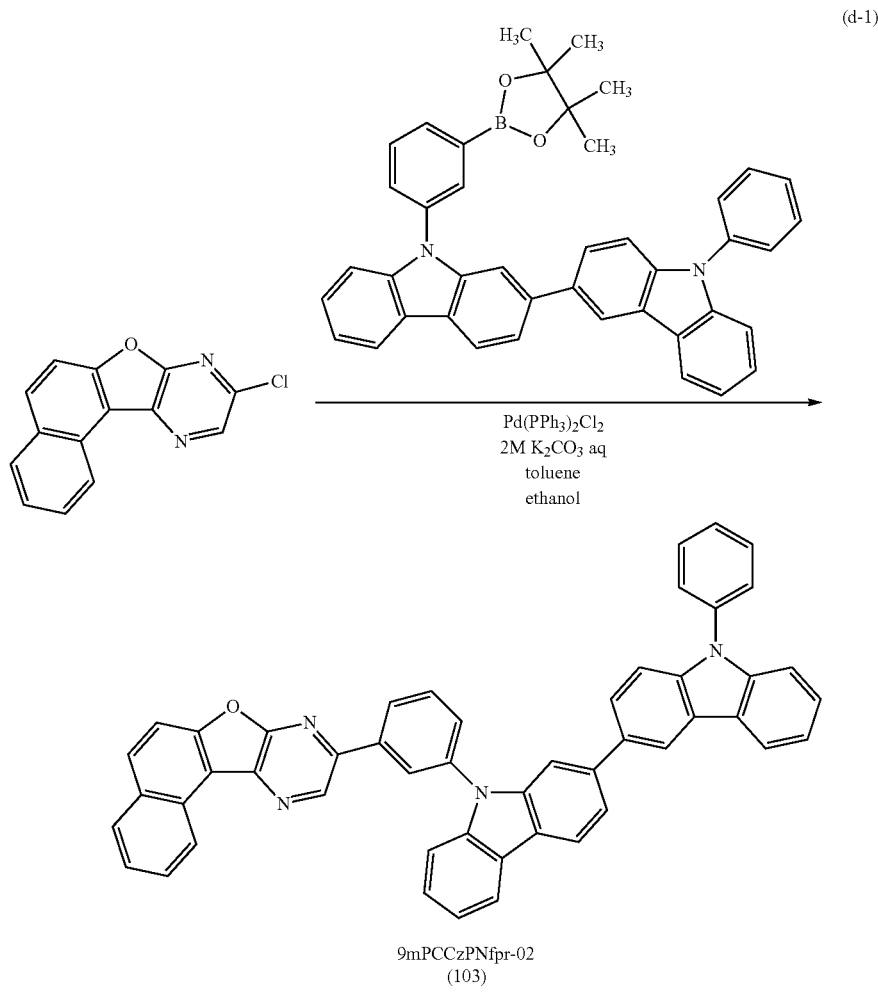

(d-1)

9mPCCzPNfpr-02
(103)

Results of analysis by nuclear magnetic resonance (¹H-NMR) spectroscopy of the yellow solid obtained above are shown below.

¹H-NMR. δ (CD$_2$Cl$_2$): 7.22-7.25 (m, 1H), 7.34-7.42 (m, 3H), 7.46-7.49 (m, 3H), 7.55-7.66 (m, 6H), 7.72-7.88 (m, 7H), 8.07 (d, 1H), 8.13 (d, 1H), 8.19-8.22 (m, 2H), 8.28 (d, 1H), 8.33 (d, 1H), 8.46 (s, 1H), 8.54 (s, 1H), 9.14 (d, 1H), 9.34 (s, 1H).

Reference Synthesis Example 5

A synthesis method of 10-[(3'-dibenzothiophen-4-yl)biphenyl-3-yl]naphtho[1',2':4,5]furo[2,3-b]pyrazine (abbreviation: 10mDBtBPNfpr), which is the organic compound represented by Structural Formula (104) in Embodiment 1, is described. The structure of 10mDBtBPNfpr is shown below.

[Chemical Formula 22]

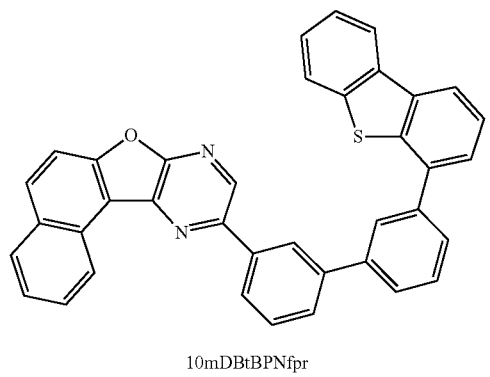

10mDBtBPNfpr (104)

Step 1; Synthesis of 5-chloro-3-(2-methoxynaphthalen-1-yl)pyrazin-2-amine

First, into a three-neck flask equipped with a reflux pipe were put 5.01 g of 3-bromo-5-chloropyrazin-2-amine, 6.04 g of 2-methoxynaphthalene-1-boronic acid, 5.32 g of potassium fluoride, and 86 mL of dehydrated tetrahydrofuran, and the air in the flask was replaced with nitrogen. The mixture in the flask was degassed by being stirred under reduced pressure, 0.44 g of tris(dibenzylideneacetone)dipalladium (0) (abbreviation: Pd$_2$(dba)$_3$) and 3.4 mL of tri-tert-butylphosphine (abbreviation: P(tBu)$_3$) were added thereto, and then stirring was performed at 80° C. for 22 hours for reaction.

After a predetermined time elapsed, the obtained mixture was subjected to suction filtration and the filtrate was concentrated. Then, purification by silica gel column chromatography using a developing solvent of toluene: ethyl acetate=10:1 was performed, whereby a target pyrazine derivative was obtained (yellowish white powder, 5.69 g, in a yield of 83%). The synthesis scheme of Step 1 is shown in Formula (e-1) below.

[Chemical Formula 23]

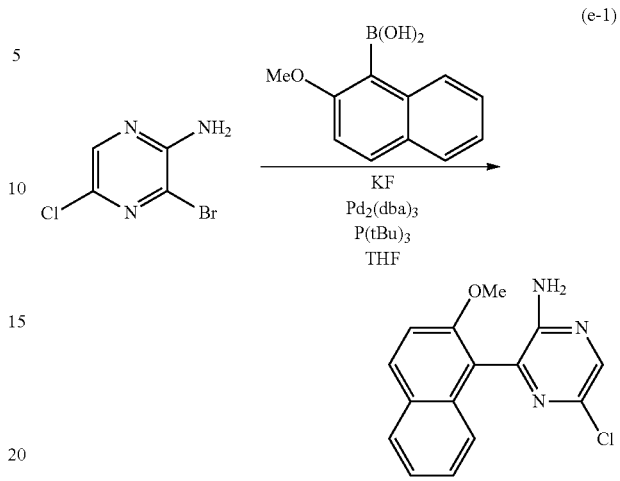

(e-1)

Step 2; Synthesis of 10-chloro-naphtho[1',2':4,5]furo[2,3-b]pyrazine

Next, into a three-neck flask were put 5.69 g of 5-chloro-3-(2-methoxynaphthalen-1-yl)pyrazin-2-amine obtained in Step 1, 150 mL of dehydrated tetrahydrofuran, and 150 mL of a glacial acetic acid, and the air in the flask was replaced with nitrogen. After the flask was cooled down to -10° C., 7.1 mL of tert-butyl nitrite was dripped, and stirring was performed at -10° C. for 1 hour and at 0° C. for 3.5 hours. After a predetermined time elapsed, 1 L of water was added to the obtained suspension and suction filtration was performed, whereby a target pyrazine derivative was obtained (yellowish white powder, 4.06 g, in a yield of 81%). The synthesis scheme of Step 2 is shown in Formula (e-2) below.

[Chemical Formula 24]

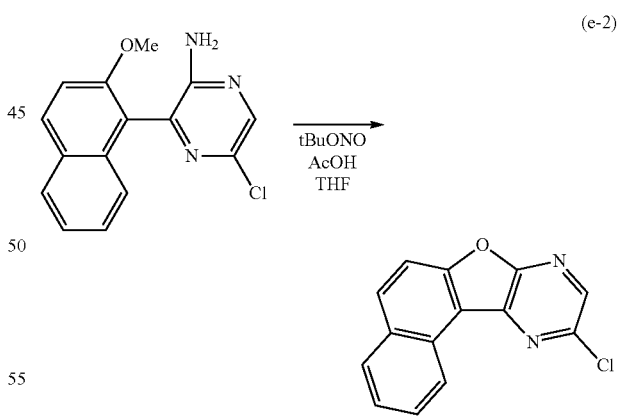

(e-2)

Step 3; Synthesis of 10mDBtBPNfpr

Into a three-neck flask were put 1.18 g of 10-chloronaphtho[1',2':4,5]furo[2,3-b]pyrazine obtained in Step 2, 2.75 g of 3'-(4-dibenzothiophene)-1,1'-biphenyl-3-boronic acid, 7.5 mL of a 2M aqueous solution of potassium carbonate, 60 mL of toluene, and 6 mL of ethanol, and the air in the flask was replaced with nitrogen. The mixture in the flask was degassed by being stirred under reduced pressure, 0.66 g of bis(triphenylphosphine)palladium(II) dichloride (abbreviation: Pd(PPh$_3$)$_2$Cl$_2$) was added thereto, and then stirring was performed at 90° C. for 22.5 hours for reaction.

After a predetermined time elapsed, the obtained suspension was subjected to suction filtration, followed by washing with water and ethanol. The obtained solid was dissolved in toluene, and the mixture was filtered through a filter aid in which Celite, alumina, and Celite were stacked in this order and was recrystallized with a mixed solvent of toluene and hexane, whereby a target substance was obtained (a white solid, 2.27 g, in a yield of 87%).

By a train sublimation method, 2.24 g of the obtained white solid was purified by sublimation. The conditions of the purification by sublimation were such that the solid was heated under a pressure of 2.3 Pa at 310° C. while the argon gas flowed at a flow rate of 16 mL/min. After the purification by sublimation, 1.69 g of a target white solid was obtained in a yield of 75%. The synthesis scheme of Step 3 is shown in Formula (e-3) below.

[Chemical Formula 25]

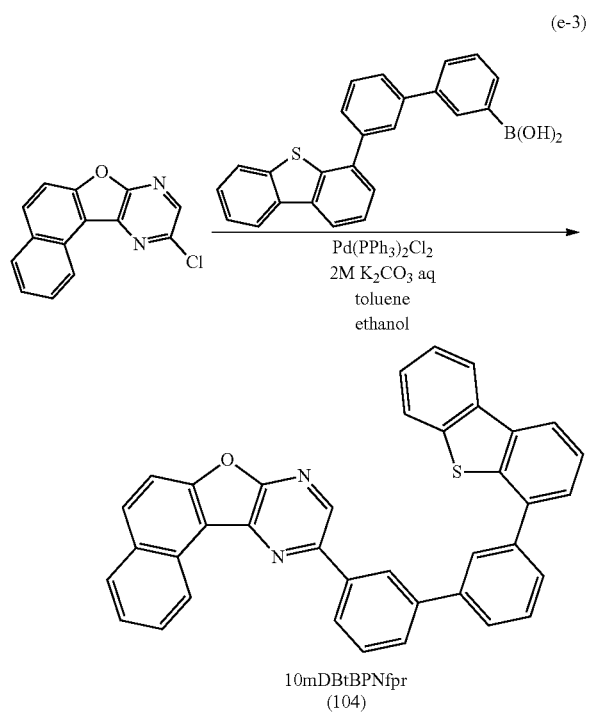

(e-3)

10mDBtBPNfpr
(104)

Results of analysis by nuclear magnetic resonance spectroscopy ($^1$H-NMR) of the white solid obtained in Step 3 are shown below.

$^1$H-NMR. δ (CDCl$_3$): 7.43 (t, 1H), 7.48 (t, 1H), 7.59-7.62 (m, 3H), 7.68-7.86 (m, 8H), 8.05 (d, 1H), 8.12 (d, 1H), 8.18 (s, 1H), 8.20-8.24 (m, 3H), 8.55 (s, 1H), 8.92 (s, 1H), 9.31 (d, 1H).

Reference Synthesis Example 6

A synthesis method of 10-(9'-phenyl-3,3'-bi-9H-carbazol-9-yl)naphtho[1',2':4,5]furo[2,3-b]pyrazine (abbreviation: 10PCCzNfpr), which is the organic compound represented by Structural Formula (105) in Embodiment 1, is described. The structure of 10PCCzNfpr is shown below.

[Chemical Formula 26]

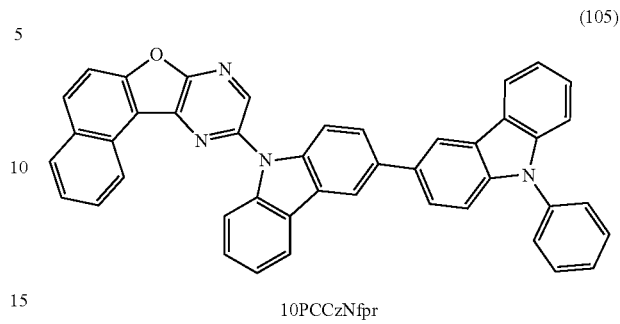

(105)

10PCCzNfpr

Into a three-neck flask were put 1.80 g of 10-chloronaphtho[1',2':4,5]furo[2,3-b]pyrazine whose synthesis method is described in Step 2 in Reference Synthesis Example 5, 3.10 g of 9'-phenyl-3,3'-bi-9H-carbazole, and 71 mL of mesitylene, and the air in the flask was replaced with nitrogen. The mixture in the flask was degassed by being stirred under reduced pressure, 2.21 g of sodium tert-butoxide, 0.041 g of tris(dibenzylideneacetone)dipalladium(0) (abbreviation: Pd$_2$(dba)$_3$), and 0.061 g of 2-dicyclohexylphosphino-2',6'-dimethoxybiphenyl (abbreviation: S-Phos) were added thereto, and then stirring was performed at 120° C. for 2 hours for reaction.

After a predetermined time elapsed, the obtained suspension was subjected to suction filtration, followed by washing with water and ethanol. The obtained solid was dissolved in toluene, and the mixture was filtered through a filter aid in which Celite, alumina, and Celite were stacked in this order and was recrystallized with a mixed solvent of toluene and hexane, whereby a target substance was obtained (an orange solid, 3.47 g, in a yield of 78%).

By a train sublimation method, 3.42 g of the obtained orange solid was purified by sublimation. The conditions of the purification by sublimation were such that the solid was heated under a pressure of 2.4 Pa at 350° C. while the argon gas flowed at a flow rate of 16 mL/min. After the purification by sublimation, 2.86 g of a target orange solid was obtained in a yield of 84%. The synthesis scheme is shown in (f-1) below.

[Chemical Formula 27]

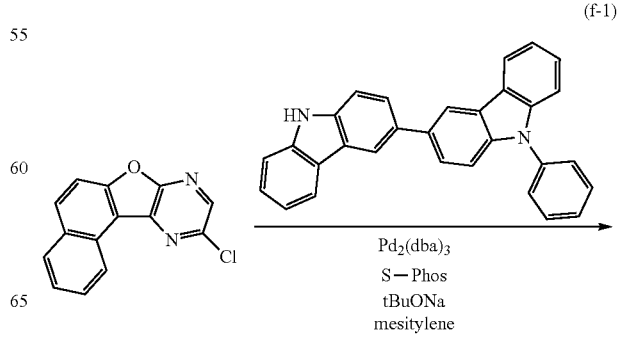

(f-1)

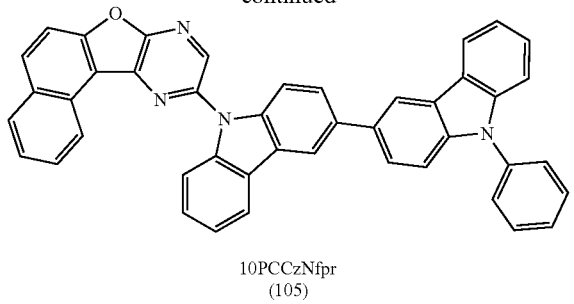

10PCCzNfpr
(105)

Results of analysis by nuclear magnetic resonance ($^1$H-NMR) spectroscopy of the orange solid obtained by the above synthesis method are shown below.

$^1$H-NMR. δ (CDCl$_3$): 7.32-7.35 (m, 1H), 7.43-7.57 (m, 6H), 7.63-7.68 (m, 5H), 7.79-7.84 (m, 2H), 7.89-7.91 (m, 2H), 8.01 (d, 1H), 8.07-8.09 (m, 2H), 8.18 (d, 1H), 8.27 (d, 1H), 8.30 (d, 1H), 8.51 (s, 2H), 8.85 (s, 1H), 9.16 (d, 1H).

Reference Synthesis Example 7

A synthesis method of 12-[(3'-dibenzothiophen-4-yl)biphenyl-3-yl]phenanthro[9',10':4,5]furo[2,3-b]pyrazine (abbreviation: 12mDBtBPPnfpr), which is the organic compound represented by Structural Formula (106) in Embodiment 1, is described. The structure of 12mDBtBPPnfpr is shown below.

[Chemical Formula 28]

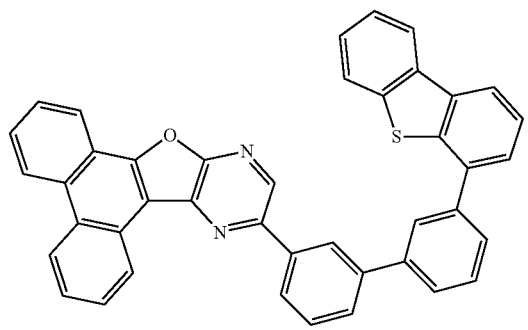

(106)

12mDBtBPPnfpr

Step 1; Synthesis of 9-methoxyphenanthrene

First, into a three-neck flask equipped with a reflux pipe were put 4.02 g of 9-bromo-phenanthrene, 7.80 g of cesium carbonate, 16 mL of toluene, and 16 mL of methanol, and the air in the flask was replaced with nitrogen. The mixture in the flask was degassed by being stirred under reduced pressure, 0.11 g of palladium(II) acetate (abbreviation: Pd(OAc)$_2$) and 0.41 g of 2-di-tert-butylphosphino-2',4',6'-triisopropylbiphenyl (abbreviation: tBuXPhos) were added thereto, and then stirring was performed at 80° C. for 17 hours for reaction.

After a predetermined time elapsed, the obtained mixture was subjected to suction filtration and the filtrate was concentrated. Then, purification by silica gel column chromatography using a developing solvent of toluene:hexane=1:3 was performed, whereby a target substance was obtained (white powder, 2.41 g, in a yield of 74%). The synthesis scheme of Step 1 is shown in Formula (g-1) below.

[Chemical Formula 29]

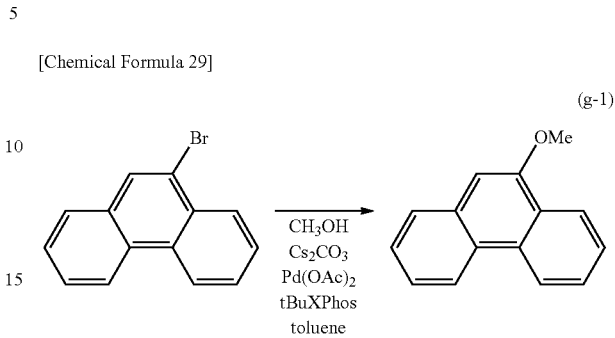

(g-1)

Step 2; Synthesis of 9-bromo-10-methoxyphenanthrene

Next, into a conical flask were put 2.75 g of 9-methoxyphenanthrene obtained in Step 1, 0.18 mL of diisopropylamine, 150 mL of dehydrated dichloromethane, and 2.52 g of N-bromosuccinimide (abbreviation: NBS), and stirring was performed at room temperature for 18 hours. After a predetermined time elapsed, the mixture was washed with water and an aqueous solution of sodium thiosulfate, and then concentrated. After that, purification by silica gel column chromatography using a developing solvent of hexane:ethyl acetate=5:1 was performed, whereby a target substance was obtained (yellowish white powder, 2.46 g, in a yield of 65%). The synthesis scheme of Step 2 is shown in Formula (g-2) below.

[Chemical Formula 30]

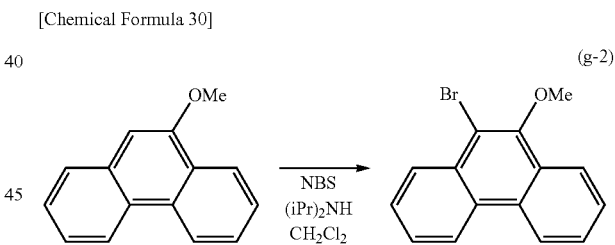

(g-2)

Step 3; Synthesis of 10-methoxyphenanthrene-9-boronic acid

Next, into a three-neck flask were put 8.49 g of 9-bromo-10-methoxyphenanthrene obtained in Step 2 and 250 mL of dehydrated THF, and the air in the flask was replaced with nitrogen. After the flask was cooled down to −78° C., 22 mL of a 1.6M hexane solution of n-butyllithium was added, and stirring was performed at −78° C. for 3 hours. Then, 5.7 mL of tetramethylethylenediamine and 4.3 mL of trimethyl borate were added, and stirring was performed at room temperature for 18 hours for reaction.

After a predetermined time elapsed, 50 mL of 1M hydrochloric acid was added, and stirring was performed at room temperature for 1 hour. Then, extraction with toluene was performed, whereby a target substance was obtained (pale orange powder, 2.87 g, in a yield of 39%). The synthesis scheme of Step 3 is shown in Formula (g-3) below.

[Chemical Formula 31]

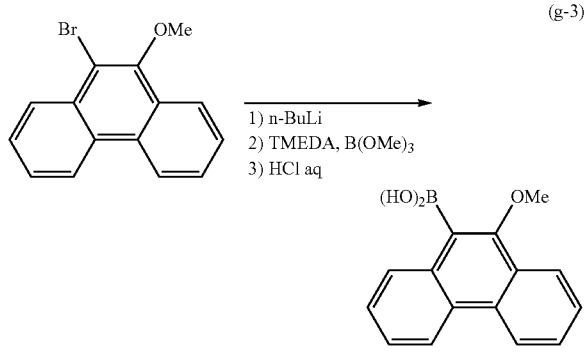

(g-3)

Step 4; Synthesis of 5-chloro-3-(10-methoxy-phenanthren-9-yl)pyrazin-2-amine

Next, into a three-neck flask equipped with a reflux pipe were put 3.69 g of 10-methoxyphenanthrene-9-boronic acid obtained in Step 3, 3.02 g of 3-bromo-5-chloropyrazin-2-amine, 70 mL of toluene, and 35 mL of a 2M sodium carbonate aqueous solution, and the air in the flask was replaced with nitrogen. The mixture in the flask was degassed by being stirred under reduced pressure, 0.16 g of tetrakis(triphenylphosphine)palladium(0) (abbreviation: Pd(PPh$_3$)$_4$) was added thereto, and then stirring was performed at 110° C. for 7.5 hours for reaction.

After a predetermined time elapsed, extraction with toluene was performed. Then, purification by flash column chromatography using a developing solvent of dichloromethane: ethyl acetate=50:1 was performed, whereby a target pyrazine derivative was obtained (yellowish white powder, 3.00 g, in a yield of 62%). The synthesis scheme of Step 4 is shown in Formula (g-4) below.

[Chemical Formula 32]

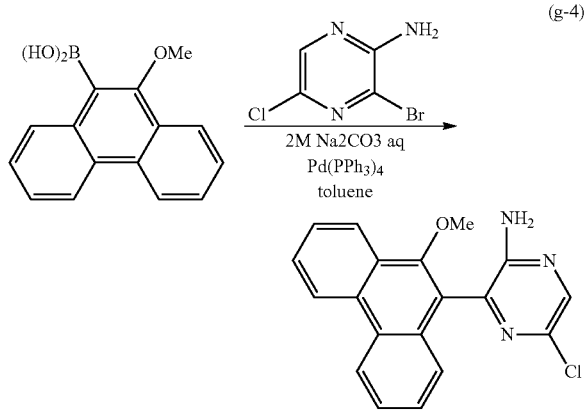

(g-4)

Step 5; Synthesis of 12-chlorophenanthro[9',10':4,5]furo[2,3-b]pyrazine

Next, into a three-neck flask were put 2.92 g of 5-chloro-3-(10-methoxyphenanthren-9-yl)pyrazin-2-amine obtained in Step 4, 60 mL of dehydrated tetrahydrofuran, and 60 mL of a glacial acetic acid, and the air in the flask was replaced with nitrogen. After the flask was cooled down to −10° C., 3.1 mL of tert-butyl nitrite was dripped, and stirring was performed at −10° C. for 1 hour and at 0° C. for 22 hours.

After a predetermined time elapsed, 200 mL of water was added to the obtained suspension and suction filtration was performed, whereby a target pyrazine derivative was obtained (yellowish white powder, 2.06 g, in a yield of 80%). The synthesis scheme of Step 5 is shown in (g-5) below.

[Chemical Formula 33]

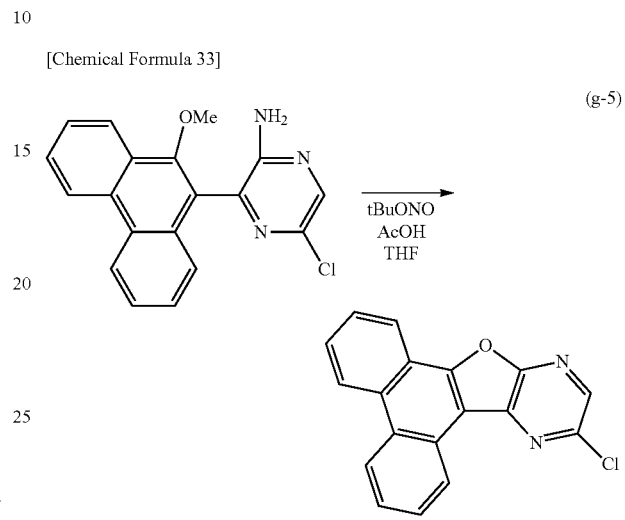

(g-5)

Step 6; Synthesis of 12-(3-chlorophenyl)phenanthro[9',10':4,5]furo[2,3-b]pyrazine Next, into a three-neck flask were put 1.02 g of 12-chlorophenanthro[9',10':4,5]furo[2,3-b]pyrazine obtained in Step 5, 0.56 g of 3-chlorophenylboronic acid, 5 mL of a 2M aqueous solution of potassium carbonate, 33 mL of toluene, and 3.3 mL of ethanol, and the air in the flask was replaced with nitrogen. The mixture in the flask was degassed by being stirred under reduced pressure, 0.074 g of palladium (II) acetate (abbreviation: Pd(OAc)$_2$) and 0.44 g of tris(2,6-dimethoxyphenyl)phosphine (abbreviation: P(2,6-MeOPh)$_3$) were added thereto, and then stirring was performed at 90° C. for 5.5 hours for reaction.

After a predetermined time elapsed, the obtained mixture was subjected to suction filtration and the filtrate was concentrated. Then, purification by silica gel column chromatography using toluene as a developing solvent was performed, whereby a target pyrazine derivative was obtained (white powder, 0.87 g, in a yield of 70%). The synthesis scheme of Step 6 is shown in Formula (g-6) below.

[Chemical Formula 34]

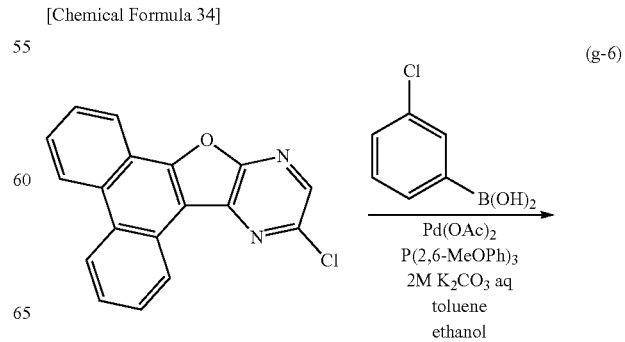

(g-6)

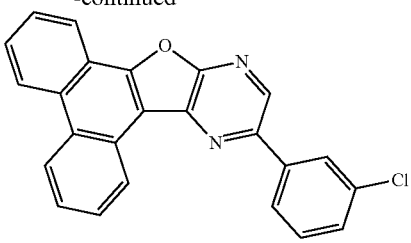

Step 7; Synthesis of 12mDBtBPPnfpr

Next, into a three-neck flask were put 0.85 g of 12-(3-chlorophenyl)phenanthro[9',10':4,5]furo[2,3-b]pyrazine obtained in Step 6, 0.73 g of 3-(4-dibenzothiophene)phenylboronic acid, 1.41 g of tripotassium phosphate, 0.49 g of tert-butyl alcohol, and 18 mL of diethylene glycol dimethyl ether (abbreviation: diglyme), and the air in the flask was replaced with nitrogen. The mixture in the flask was degassed by being stirred under reduced pressure, 9.8 mg of palladium(II) acetate (abbreviation: Pd(OAc)$_2$) and 32 mg of di(1-adamantyl)-n-butylphosphine (abbreviation: CataCXium A) were added thereto, and then stirring was performed at 140° C. for 11.5 hours for reaction.

After a predetermined time elapsed, the obtained suspension was subjected to suction filtration, followed by washing with water and ethanol. The obtained solid was dissolved in toluene, and the mixture was filtered through a filter aid in which Celite, alumina, and Celite were stacked in this order and was recrystallized with toluene, whereby a target substance was obtained (a white solid, 0.74 g, in a yield of 55%).

By a train sublimation method, 0.73 g of the obtained white solid was purified by sublimation. The conditions of the purification by sublimation were such that the solid was heated under a pressure of 2.6 Pa at 330° C. while the argon gas flowed at a flow rate of 11 mL/min. After the purification by sublimation, 0.49 g of a target white solid was obtained in a yield of 67%. The synthesis scheme of Step 7 is shown in Formula (g-7) below.

[Chemical Formula 35]

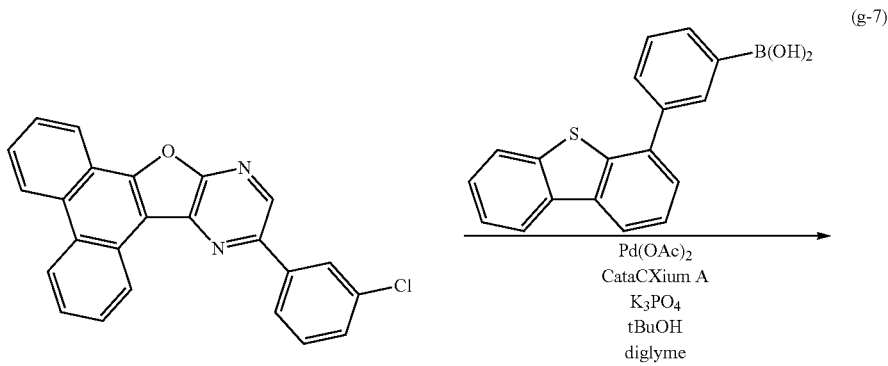

(g-7)

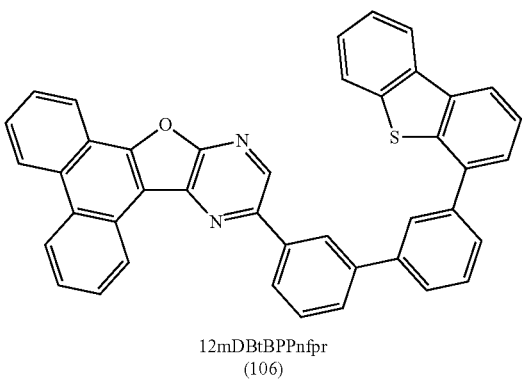

12mDBtBPPnfpr
(106)

Results of analysis by nuclear magnetic resonance spectroscopy ($^{1}$H-NMR) of the white solid obtained in Step 7 are shown below.

$^{1}$H-NMR. δ (CD$_{2}$Cl$_{2}$): 7.45 (t, 1H), 7.50 (t, 1H), 7.62-7.66 (m, 2H), 7.70-7.89 (m, 10H), 8.21-8.28 (m, 4H), 8.58-8.61 (m, 2H), 8.80 (d, 1H), 8.84 (d, 1H), 8.94 (s, 1H), 9.37 (d, 1H).

Reference Synthesis Example 8

A synthesis method of 9-[4-(9'-phenyl-3,3'-bi-9H-carbazol-9-yl)phenyl]naphtho[1',2':4,5]furo[2,3-b]pyrazine (abbreviation: 9pPCCzPNfpr), which is the organic compound represented by Structural Formula (107) in Embodiment 1, is described. The structure of 9pPCCzPNfpr is shown below.

[Chemical Formula 36]

(107)

9pPCCzNfpr

Step 1; Synthesis of 9-(4-chlorophenyl)naphtho[1', 2':4,5]furo[2,3-b]pyrazine

Into a three-neck flask were put 4.10 g of 9-chloronaphtho[1',2':4,5]furo[2,3-b]pyrazine whose synthesis method is described in Step 2 in Reference Synthesis Example 1, 2.80 g of 4-chlorophenylboronic acid, 27 mL of a 2M aqueous solution of potassium carbonate, 160 mL of toluene, and 16 mL of ethanol, and the air in the flask was replaced with nitrogen. The mixture in the flask was degassed by being stirred under reduced pressure, 0.36 g of palladium(II) acetate (abbreviation: Pd(OAc)$_{2}$) and 2.08 g of tris(2,6-dimethoxyphenyl)phosphine (abbreviation: P(2,6-MeOPh)$_{3}$) were added thereto, and then stirring was performed at 90° C. for 7 hours for reaction.

After a predetermined time elapsed, the obtained mixture was subjected to suction filtration, followed by washing with ethanol. Then, purification by silica gel column chromatography using toluene as a developing solvent was performed, whereby a target pyrazine derivative was obtained (yellowish white powder, 2.81 g, in a yield of 52%). The synthesis scheme of Step 1 is shown in Formula (h-1) below.

[Chemical Formula 37]

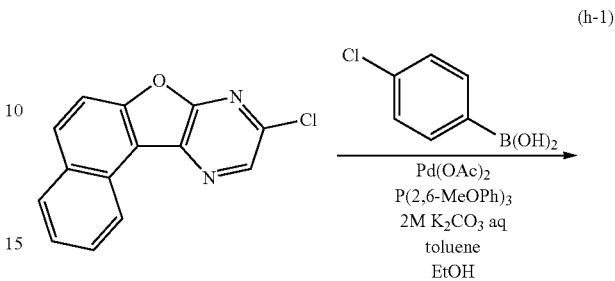

(h-1)

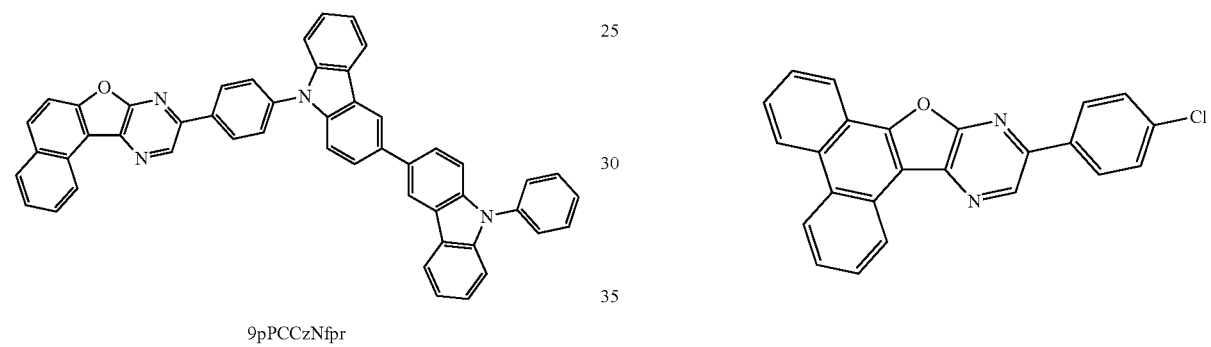

Step 2; Synthesis of 9pPCCzPNfpr

Next, into a three-neck flask were put 1.39 g of 9-(4-chlorophenyl)naphtho[1',2':4,5]furo[2,3-b]pyrazine obtained in Step 1, 1.72 g of 9'-phenyl-3,3'-bi-9H-carbazole, and 21 mL of mesitylene, and the air in the flask was replaced with nitrogen. The mixture in the flask was degassed by being stirred under reduced pressure, 0.81 g of sodium tert-butoxide, 0.024 g of tris(dibenzylideneacetone)dipalladium(0) (abbreviation: Pd$_{2}$(dba)$_{3}$), and 0.034 g of 2-dicyclohexylphosphino-2',6'-dimethoxybiphenyl (abbreviation: S-Phos) were added thereto, and then stirring was performed at 150° C. for 6 hours for reaction.

After a predetermined time elapsed, the reaction solution was subjected to extraction with toluene. The solid obtained by concentrating the solution of the extract was purified by silica gel column chromatography using toluene as a developing solvent, and then recrystallized with toluene three times, whereby a target substance was obtained (a yellow solid, 1.84 g, in a yield of 62%).

By a train sublimation method, 1.81 g of the obtained yellow solid was purified by sublimation. The conditions of the purification by sublimation were such that the solid was heated under a pressure of 2.7 Pa at 380° C. while the argon gas flowed at a flow rate of 18 mL/min. After the purification by sublimation, 1.35 g of a target yellow solid was obtained in a yield of 75%. The synthesis scheme of Step 2 is shown in Formula (h-2) below.

[Chemical Formula 38]

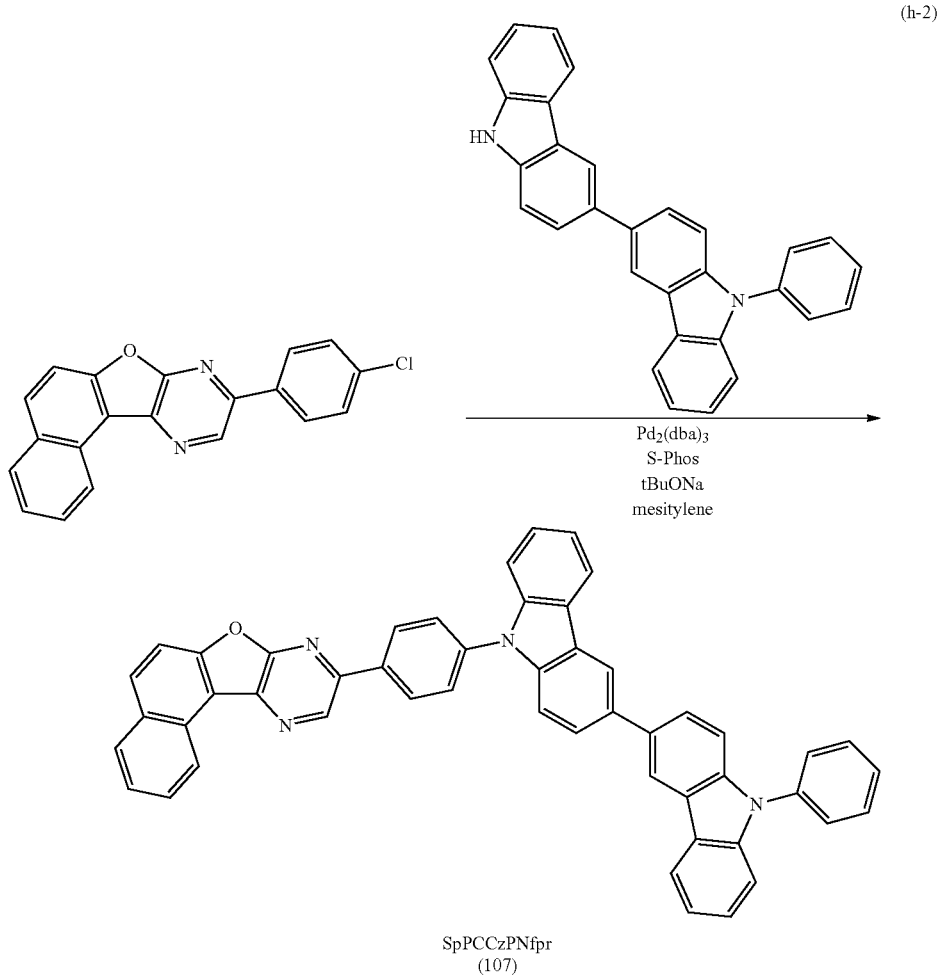

Results of analysis by nuclear magnetic resonance ($^1$H-NMR) spectroscopy of the yellow solid obtained in Step 2 are shown below.

$^1$H-NMR. δ (CD$_2$Cl$_2$): 7.32-7.39 (m, 2H), 7.44-7.56 (m, 5H), 7.61 (d, 1H), 7.64-7.69 (m, 6H), 7.83-7.91 (m, 6H), 8.11 (d, 1H), 8.17 (d, 1H), 8.28 (d, 2H), 8.49-8.53 (m, 4H), 9.18 (d, 1H), 9.40 (s, 1H).

Reference Synthesis Example 9

A synthesis method of 9-[4-(9'-phenyl-2,3'-bi-9H-carbazol-9-yl)phenyl]naphtho[1',2':4,5]furo[2,3-b]pyrazine (abbreviation: 9pPCCzPNfpr-02), which is the organic compound represented by Structural Formula (108) in Embodiment 1, is described. The structure of 9pPCCzPNfpr-02 is shown below.

Into a three-neck flask were put 1.76 g of 9-(4-chlorophenyl)naphtho[1',2':4,5]furo[2,3-b]pyrazine whose synthesis method is described in Step 1 in Reference Synthesis Example 8, 2.22 g of 9'-phenyl-2,3'-bi-9H-carbazole, and 27 mL of mesitylene, and the air in the flask was replaced with nitrogen. The mixture in the flask was degassed by being stirred under reduced pressure, 1.09 g of sodium tert-butoxide, 0.031 g of tris(dibenzylideneacetone)dipalladium (0) (abbreviation: $Pd_2(dba)_3$), and 0.045 g of 2-dicyclohexylphosphino-2',6'-dimethoxybiphenyl (abbreviation: S-Phos) were added thereto, and then stirring was performed at 150° C. for 6 hours for reaction.

After a predetermined time elapsed, the obtained suspension was subjected to suction filtration and the residue was washed with water and ethanol. The obtained solid was purified by silica gel column chromatography using toluene as a developing solvent, and then recrystallized with a mixed solvent of toluene and hexane, whereby a target substance was obtained (a yellow solid, 1.95 g, in a yield of 52%).

By a train sublimation method, 1.94 g of the obtained yellow solid was purified by sublimation. The conditions of the purification by sublimation were such that the solid was heated under a pressure of 2.7 Pa at 380° C. while the argon gas flowed at a flow rate of 18 mL/min. After the purification by sublimation, 1.62 g of a target yellow solid was obtained in a yield of 84%. The synthesis scheme is shown in Formula (i-1) below.

[Chemical Formula 40]

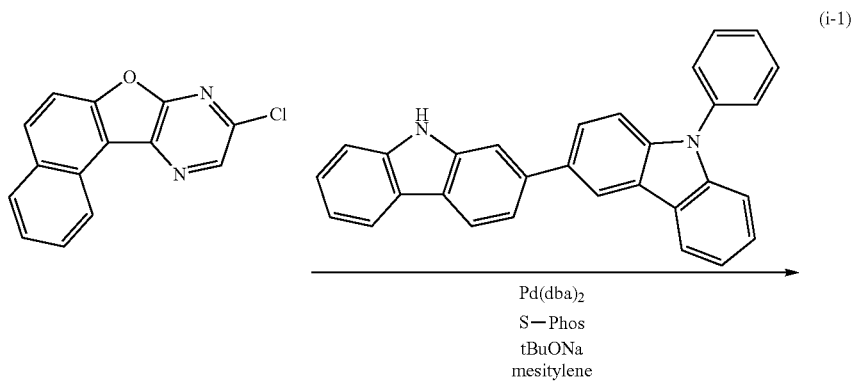

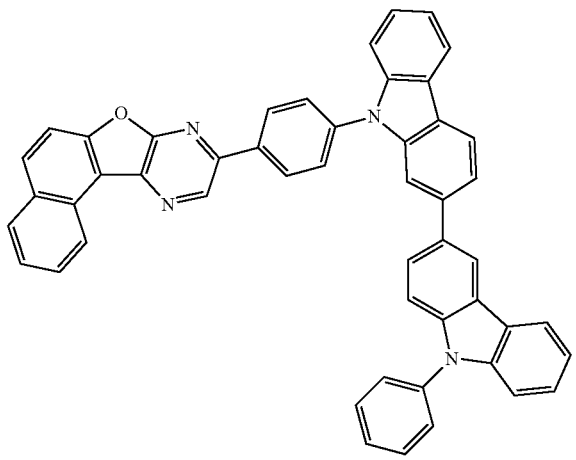

Results of analysis by nuclear magnetic resonance ($^1$H-NMR) spectroscopy of the yellow solid obtained above are shown below.

$^1$H-NMR. δ (CD$_2$Cl$_2$): 7.28-7.31 (m, 1H), 7.36 (t, 1H), 7.40-7.44 (m, 2H), 7.46-7.51 (m, 3H), 7.57-7.69 (m, 6H), 7.74 (d, 1H), 8.78 (d, 1H), 7.84 (t, 1H), 7.81-7.88 (m, 4H), 8.10 (d, 1H), 8.16 (d, 1H), 8.22 (d, 2H), 8.28 (d, 1H), 8.46 (s, 1H), 8.50 (d, 2H), 9.17 (d, 1H), 9.38 (s, 1H).

Reference Synthesis Example 10

A synthesis method of 9-[3'-(6-phenylbenzo[b]naphtho[1,2-d]furan-8-yl)biphenyl-3-yl]naphtho[1',2':4,5]furo[2,3-b]pyrazine (abbreviation: 9mBnfBPNfpr), which is the organic compound represented by Structural Formula (109) in Embodiment 1, is described. The structure of 9mBnfBPNfpr is shown below.

[Chemical Formula 41]

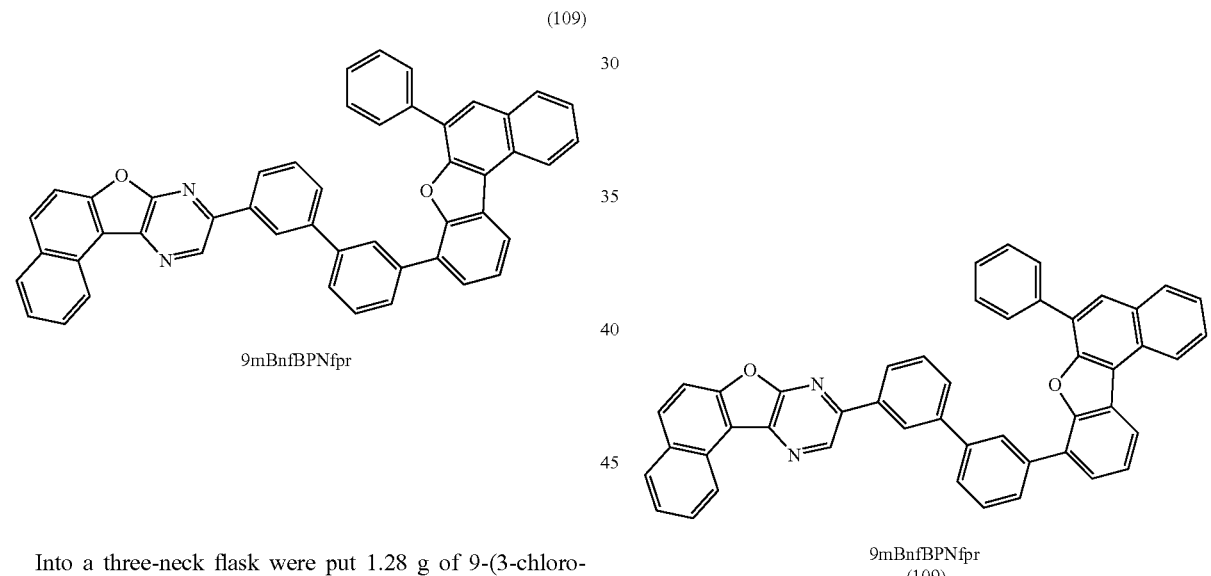

Into a three-neck flask were put 1.28 g of 9-(3-chlorophenyl)naphtho[1',2':4,5]furo[2,3-b]pyrazine whose synthesis method is described in Step 1 in Reference Synthesis Example 3, 2.26 g of 3-(6-phenylbenzo[b]naphtho[1,2-d]furan-8-yl)phenylboronic acid pinacol ester, 2.53 g of tripotassium phosphate, 0.89 g of tert-butyl alcohol, and 32 mL of diethylene glycol dimethyl ether (abbreviation: diglyme), and the air in the flask was replaced with nitrogen. The mixture in the flask was degassed by being stirred under reduced pressure, 8.8 mg of palladium(II) acetate (abbreviation: Pd(OAc)$_2$) and 28 mg of di(1-adamantyl)-n-butylphosphine (abbreviation: CataCXium A) were added thereto, and then stirring was performed at 140° C. for 8.5 hours for reaction.

After a predetermined time elapsed, the obtained suspension was subjected to suction filtration, followed by washing with water and ethanol. The obtained solid was purified by silica gel column chromatography using toluene as a developing solvent, and then recrystallized with toluene, whereby a target substance was obtained (a yellow solid, 0.66 g, in a yield of 25%).

The synthesis scheme is shown in Formula (j-1) below.

[Chemical Formula 42]

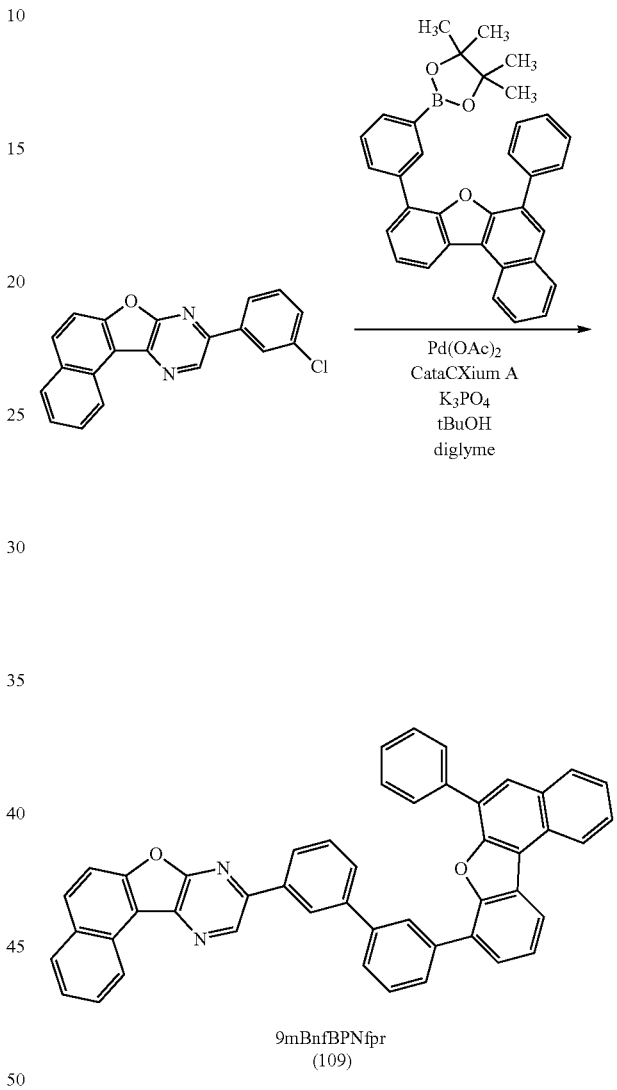

Results of analysis by nuclear magnetic resonance ($^1$H-NMR) spectroscopy of the yellow solid obtained above are shown below.

$^1$H-NMR. δ (CD$_2$Cl$_2$): 7.24-7.28 (m, 3H), 7.61-7.72 (m, 5H), 7.78-7.87 (m, 6H), 7.98-8.00 (m, 3H), 8.08 (d, 1H), 8.11-8.15 (m, 3H), 8.25 (d, 1H), 8.48 (s, 1H), 8.51-8.53 (m, 2H), 8.75 (d, 1H), 9.15 (d, 1H), 9.32 (s, 1H).

Reference Synthesis Example 11

A synthesis method of 9-[3'-(6-phenyldibenzothiophen-4-yl)biphenyl-3-yl]naphtho[1',2':4,5]furo[2,3-b]pyrazine (abbreviation: 9mDBtBPNfpr-02), which is the organic compound represented by Structural Formula (110) in Embodiment 1, is described. The structure of 9mDBtBPNfpr-02 is shown below.

[Chemical Formula 43]

(110)

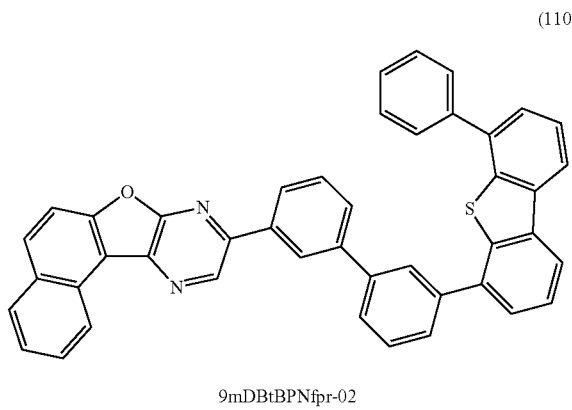

9mDBtBPNfpr-02

Into a three-neck flask were put 1.19 g of 9-(3-chlorophenyl)naphtho[1',2':4,5]furo[2,3-b]pyrazine whose synthesis method is described in Step 1 in Reference Synthesis Example 3, 1.97 g of 3-(6-phenyldibenzothiophen-4-yl)phenylboronic acid pinacol ester, 2.29 g of tripotassium phosphate, 0.82 g of tert-butyl alcohol, and 29 mL of diethylene glycol dimethyl ether (abbreviation: diglyme), and the air in the flask was replaced with nitrogen. The mixture in the flask was degassed by being stirred under reduced pressure, 16 mg of palladium(II) acetate (abbreviation: Pd(OAc)₂) and 52 mg of di(1-adamantyl)-n-butylphosphine (abbreviation: CataCXium A) were added thereto, and then stirring was performed at 140° C. for 15 hours for reaction.

After a predetermined time elapsed, the obtained suspension was subjected to suction filtration, followed by washing with water and ethanol. The obtained solid was purified by silica gel column chromatography using toluene as a developing solvent, and then recrystallized with toluene, whereby a target substance was obtained (a yellowish white solid, 1.17 g, in a yield of 52%). The synthesis scheme is shown in Formula (k-1) below.

[Chemical Formula 44]

(k-1)

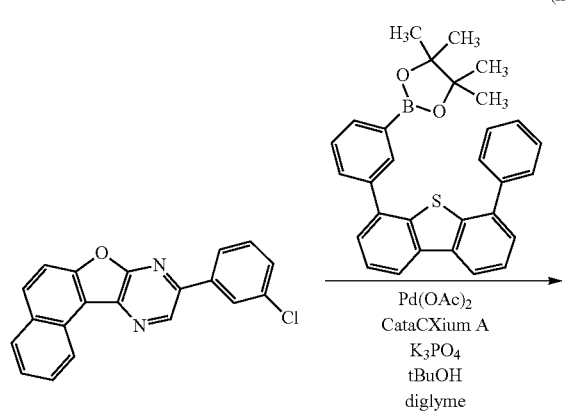

-continued

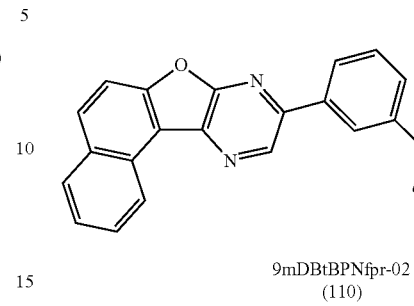

9mDBtBPNfpr-02
(110)

Results of analysis by nuclear magnetic resonance ($^1$H-NMR) spectroscopy of the yellowish white solid obtained above are shown below.

$^1$H-NMR. δ (CD₂Cl₂): 7.39 (t, 1H), 7.47-7.51 (m, 3H), 7.58-7.67 (m, 6H), 7.73 (d, 2H), 7.78-7.85 (m, 5H), 8.02 (s, 1H), 8.06 (d, 1H), 8.10 (d, 1H), 8.18 (d, 1H), 8.23 (t, 2H), 8.49 (s, 1H), 9.17 (d, 1H), 9.30 (s, 1H).

Reference Synthesis Example 12

A synthesis method of 9-{3-[6-(9,9-dimethylfluoren-2-yl)dibenzothiophen-4-yl]phenyl}naphtho[1',2':4,5]furo[2,3-b] pyr azine (abbreviation: 9mFDBtPNfpr), which is the organic compound represented by Structural Formula (111) in Embodiment 1, is described. The structure of 9mFDBtPNfpr is shown below.

[Chemical Formula 45]

(111)

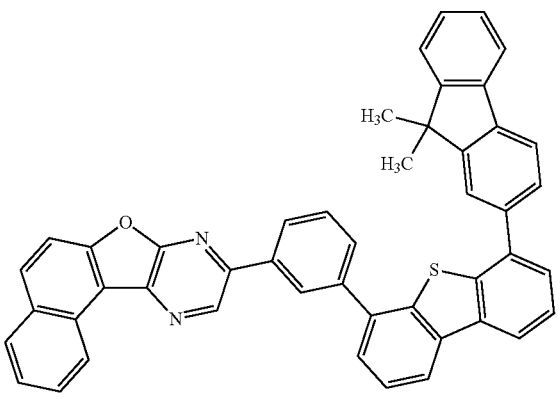

9mFDBtPNfpr

Into a three-neck flask were put 1.01 g of 9-(3-chlorophenyl)naphtho[1',2':4,5]furo[2,3-b]pyrazine whose synthesis method is described in Step 1 in Reference Synthesis Example 3, 1.46 g of 3-[6-(9,9-dimethylfluoren-2-yl)dibenzothiophen-4-yl]phenylboronic acid, 1.89 g of tripotassium phosphate, 0.67 g of tert-butyl alcohol, and 24 mL of diethylene glycol dimethyl ether (abbreviation: diglyme), and the air in the flask was replaced with nitrogen. The mixture in the flask was degassed by being stirred under reduced pressure, 27 mg of palladium(II) acetate (abbreviation: Pd(OAc)₂) and 88 mg of di(1-adamantyl)-n-butylphosphine (abbreviation: CataCXium A) were added thereto, and then stirring was performed at 140° C. for 30 hours for reaction.

After a predetermined time elapsed, the obtained suspension was subjected to suction filtration, followed by washing with water and ethanol. The obtained solid was purified by silica gel column chromatography using toluene as a developing solvent, and then recrystallized with a mixed solvent of toluene and hexane, whereby a target substance was obtained (a yellowish white solid, 0.75 g, in a yield of 37%). The synthesis scheme is shown in (1-1) below.

[Chemical Formula 46]

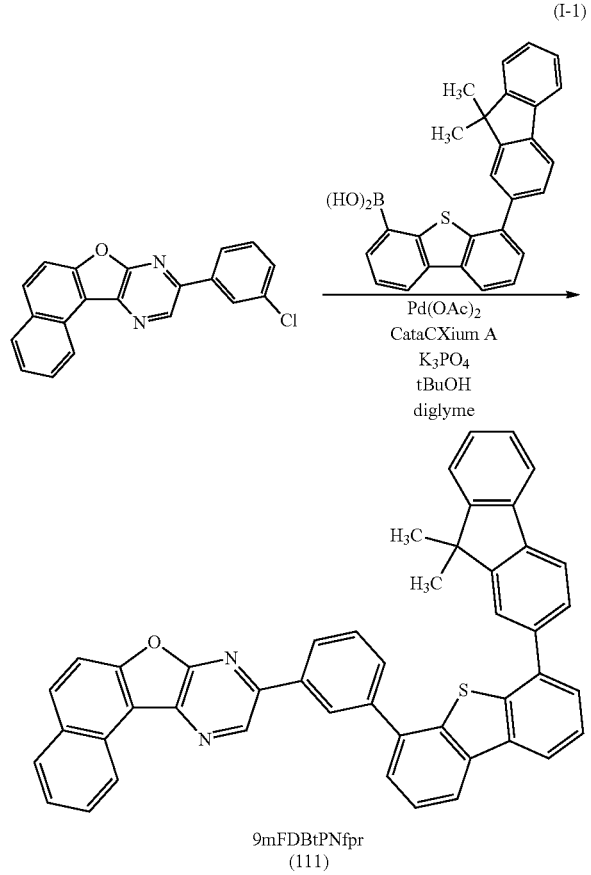

9mFDBtPNfpr
(111)

Results of analysis by nuclear magnetic resonance ($^1$H-NMR) spectroscopy of the yellowish white solid obtained above are shown below.

$^1$H-NMR. δ (CD$_2$Cl$_2$): 1.47 (s, 6H), 7.27-7.32 (m, 2H), 7.38 (d, 1H), 7.61-7.76 (m, 8H), 7.79-7.85 (m, 4H), 7.89 (d, 1H), 8.08 (d, 1H), 8.13 (d, 1H), 8.24-8.31 (m, 3H), 8.59 (s, 1H), 9.14 (d, 1H), 9.31 (s, 1H).

Reference Synthesis Example 13

A synthesis method of 11-(3-naphtho[1',2':4,5]furo[2,3-b]pyrazin-9-yl-phenyl)-12-phenylindolo[2,3-a]carbazole (abbreviation: 9mIcz(II)PNfpr), which is the organic compound represented by Structural Formula (112) in Embodiment 1, is described. The structure of 9mIcz(II)PNfpr is shown below.

[Chemical Formula 47]

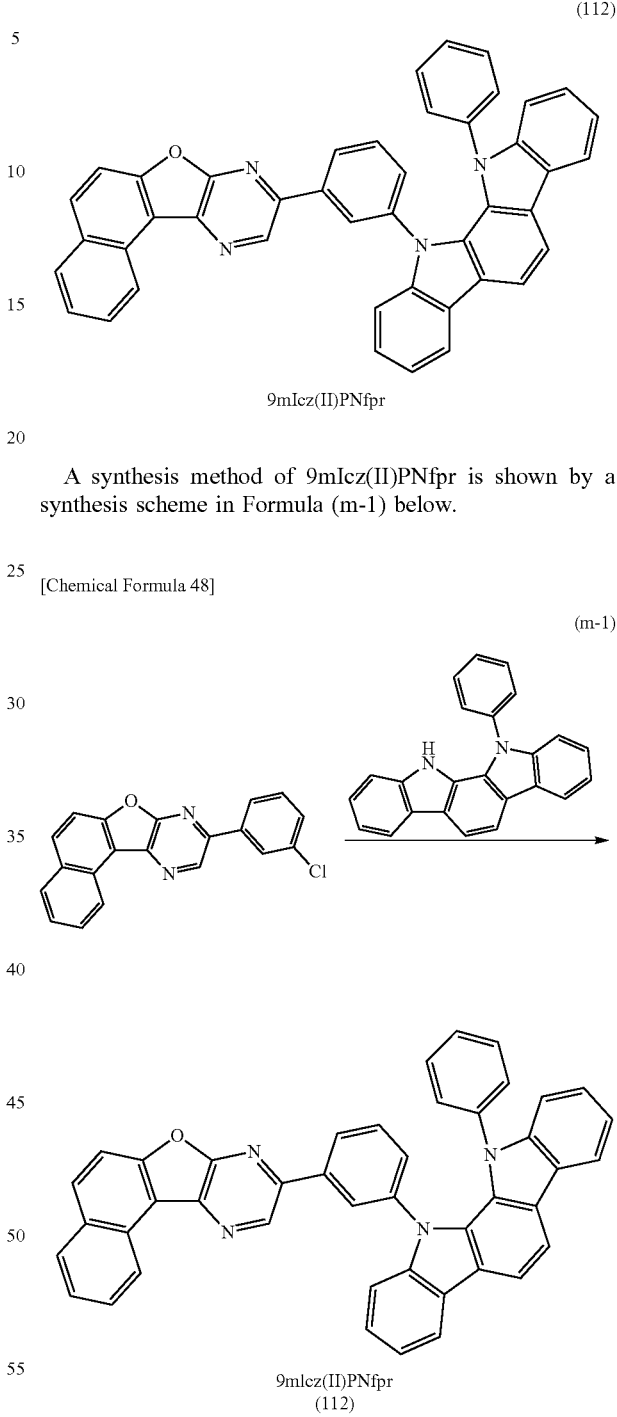

9mIcz(II)PNfpr

A synthesis method of 9mIcz(II)PNfpr is shown by a synthesis scheme in Formula (m-1) below.

[Chemical Formula 48]

Reference Synthesis Example 14

A synthesis method of 3-naphtho[1',2':4,5]furo[2,3-b]pyrazin-9-yl-N,N-diphenylbenzenamine (abbreviation: 9mTPANfpr), which is the organic compound represented by Structural Formula (113) in Embodiment 1, is described. The structure of 9mTPANfpr is shown below.

[Chemical Formula 49]

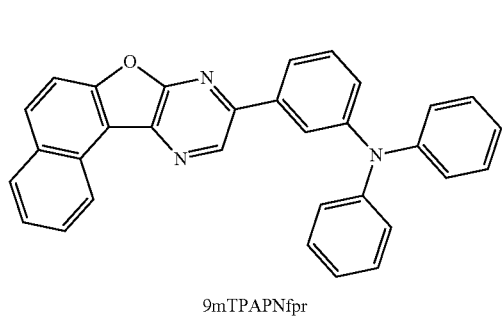

9mTPAPNfpr (113)

A synthesis method of 9mTPANfpr is shown by a synthesis scheme in Formula (n-1) below.

[Chemical Formula 50]

(n-1)

[Chemical Formula 51]

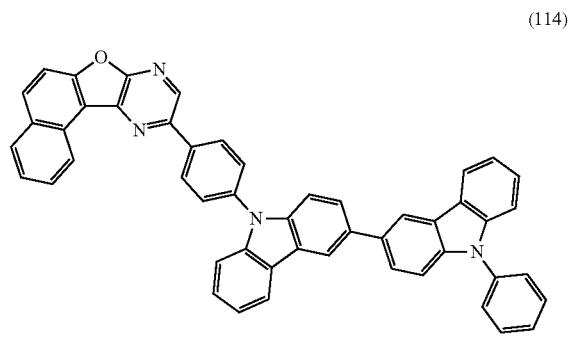

10mPCCzPNfpr (114)

A synthesis method of 10mPCCzPNfpr is shown by synthesis schemes in Formula (o-1) to Formula (o-4) below.

[Chemical Formula 52]

(o-1)

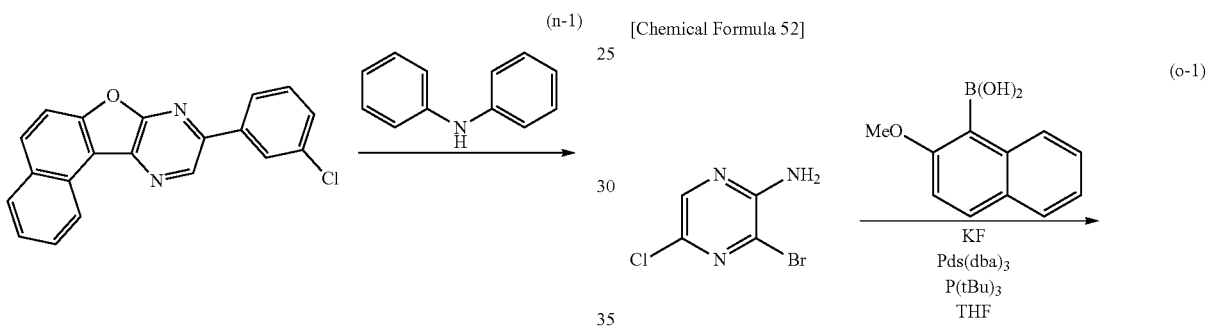

9mTPAPNfpr
(113)

Reference Synthesis Example 15

A synthesis method of 10-[4-(9'-phenyl-3,3'-bi-9H-carbazol-9-yl)phenyl]naphtho[1',2':4,5]furo[2,3-b]pyrazine (abbreviation: 10mPCCzPNfpr), which is the organic compound represented by Structural Formula (114) in Embodiment 1, is described. The structure of 10mPCCzPNfpr is shown below.

[Chemical Formula 53]

(o-2)

-continued

[Chemical Formula 54]

(o-3)

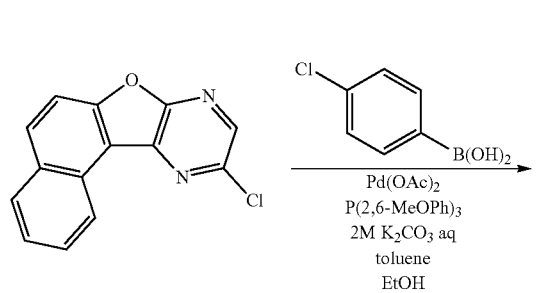

[Chemical Formula 55]

(o-4)

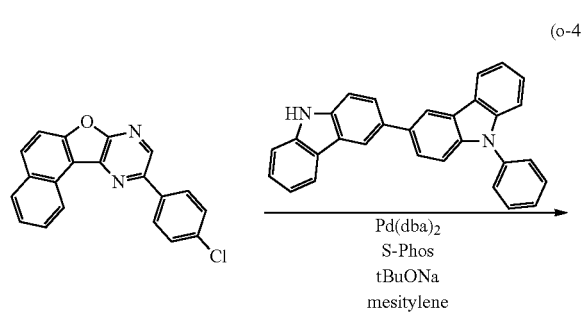

10mPCCzPNfpr
(114)

Reference Synthesis Example 16

A synthesis method of 11-[(3'-(dibenzothiophen-4-yl)biphenyl-3-yl]phenanthro[9',10':4,5]furo[2,3-b]pyrazine (abbreviation: 11mDBtBPPnfpr), which is the organic compound represented by Structural Formula (115) in Embodiment 1, is described. The structure of 11mDBtBPPnfpr is shown below.

[Chemical Formula 56]

(115)

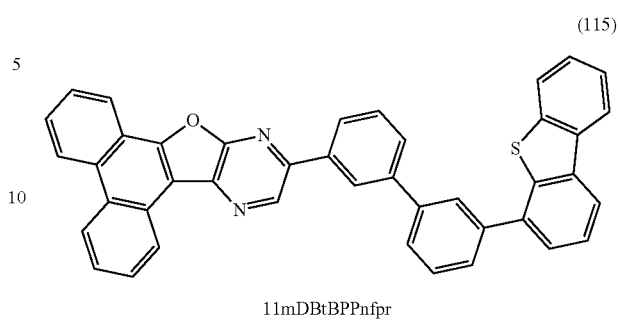

11mDBtBPPnfpr

A synthesis method of 11mDBtBPPnfpr is shown by synthesis schemes in Formula (p-1) to Formula (p-7) below.

[Chemical Formula 57]

(p-1)

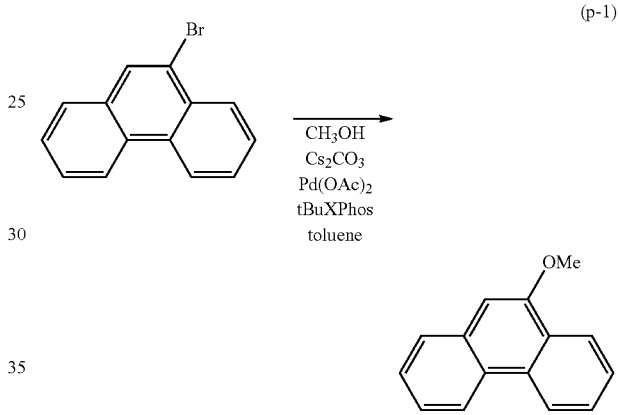

[Chemical Formula 58]

(p-2)

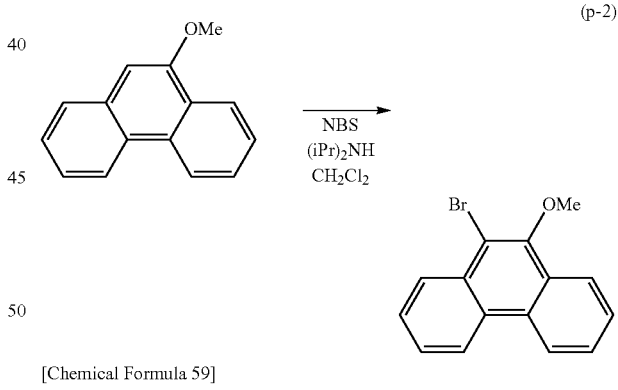

[Chemical Formula 59]

(p-3)

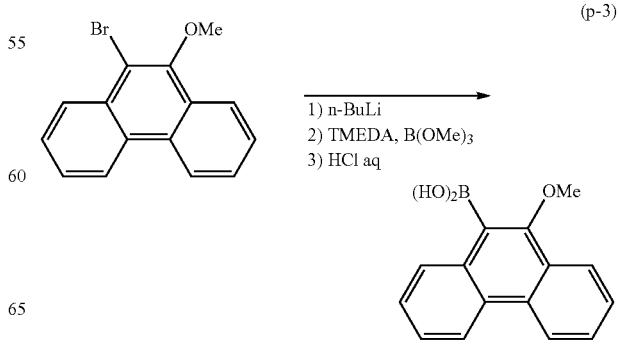

[Chemical Formula 60]

(p-4)

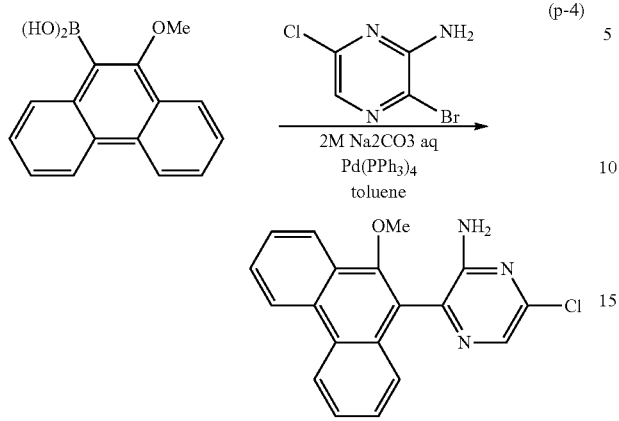

[Chemical Formula 61]

(p-5)

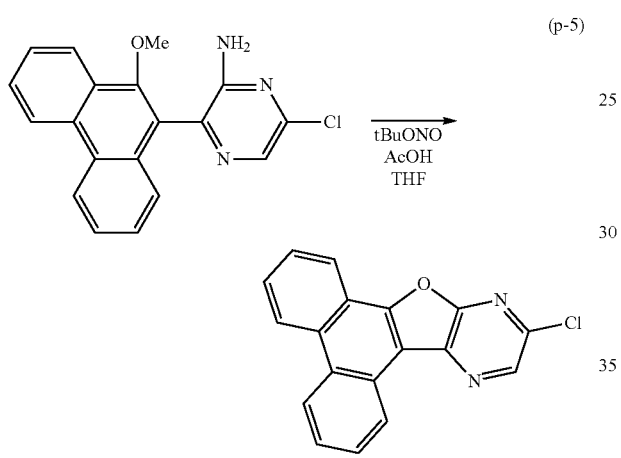

[Chemical Formula 62]

(p-6)

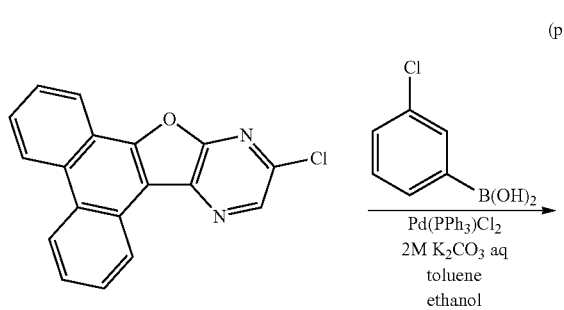

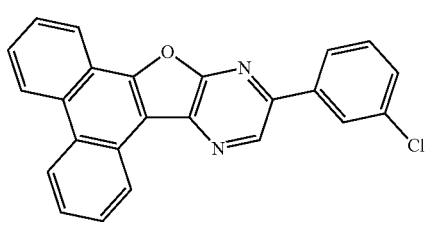

[Chemical Formula 63]

(p-7)

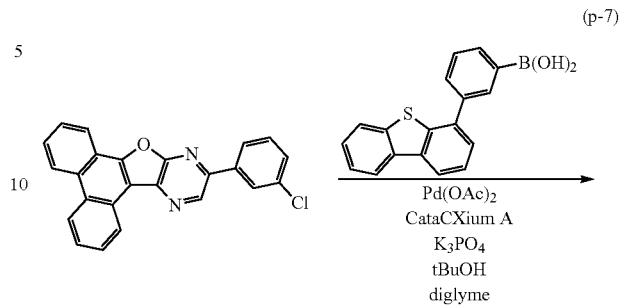

11mDBtBPPnfpr
(115)

Reference Example 17

A synthesis method of 10-[3-(9'-phenyl-3,3'-bi-9H-carbazol-9-yl)phenyl]naphtho[1',2':4,5]furo[2,3-b]pyrazine (abbreviation: 10pPCCzPNfpr), which is the organic compound represented by Structural Formula (116) in Embodiment 1, is described. The structure of 10pPCCzPNfpr is shown below.

[Chemical Formula 64]

(116)

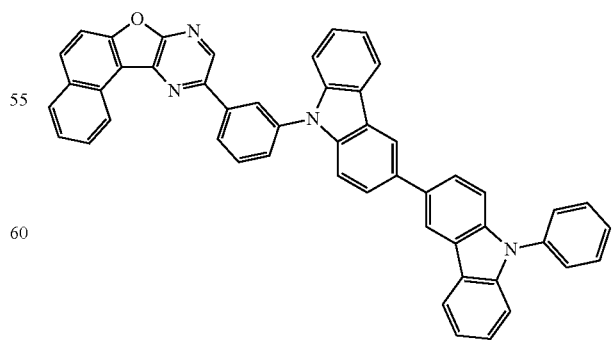

10pPCCzPNfpr

A synthesis method of 10pPCCzPNfpr is shown by synthesis schemes in Formula (q-1) to Formula (q-4) below.

[Chemical Formula 65]

(q-1)

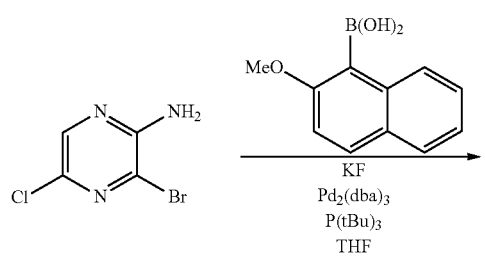

[Chemical Formula 66]

(q-2)

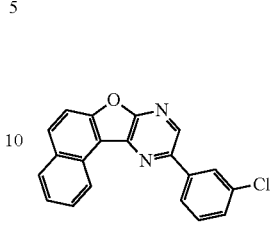

[Chemical Formula 67]

(q-3)

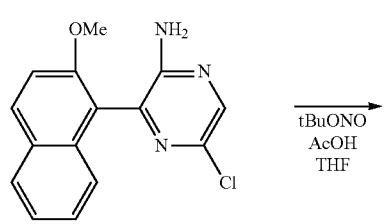

[Chemical Formula 68]

(q-4)

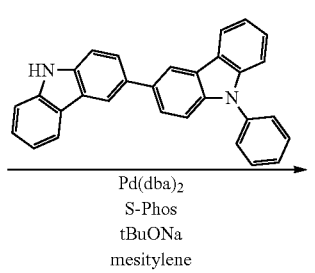

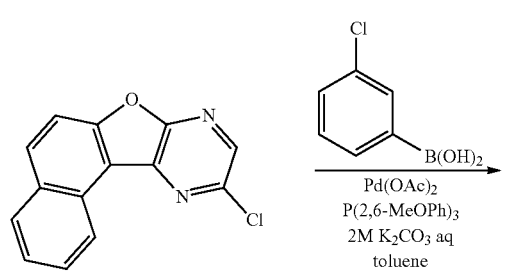

10pPCCzPNfpr
(116)

Reference Synthesis Example 18

A synthesis method of 9-[3-(7H-dibenzo[c,g]carbazol-7-yl)phenyl]naphtho[1',2':4,5]furo[2,3-b]pyrazine (abbreviation: 9mcgDBCzPNfpr), which is the organic compound represented by Structural Formula (117) in Embodiment 1, is described. The structure of 9mcgDBCzPNfpr is shown below.

[Chemical Formula 69]

(117)

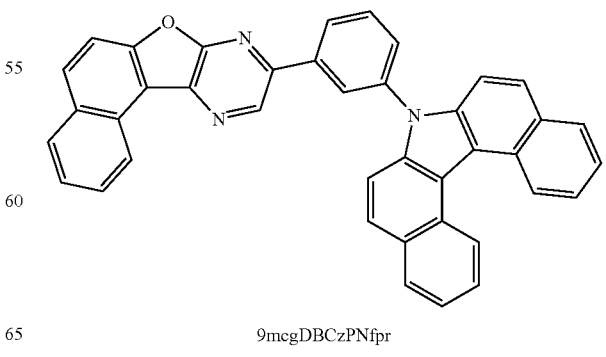

9mcgDBCzPNfpr

A synthesis method of 9mcgDBCzPNfpr is shown by synthesis schemes in Formula (r-1) to Formula (r-4) below.

[Chemical Formula 70]

(r-1)

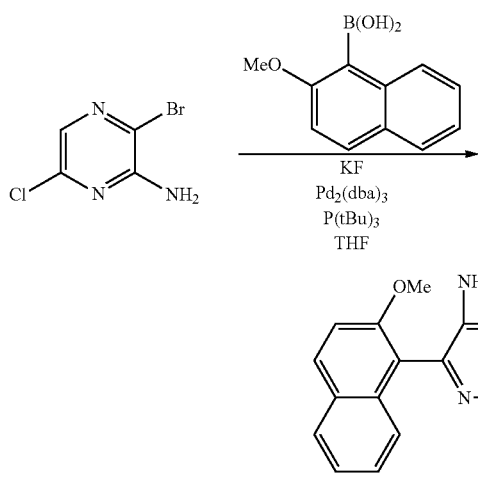

[Chemical Formula 71]

(r-2)

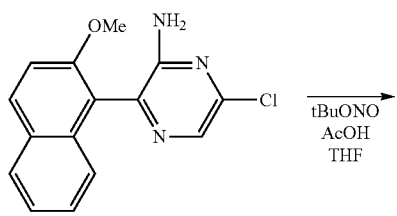

[Chemical Formula 72]

(r-3)

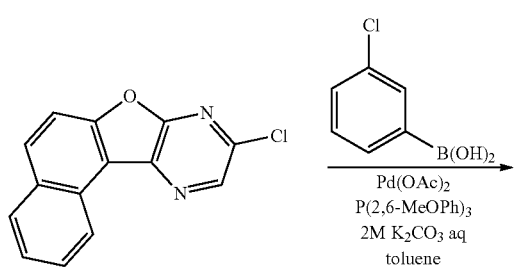

[Chemical Formula 73]

(r-4)

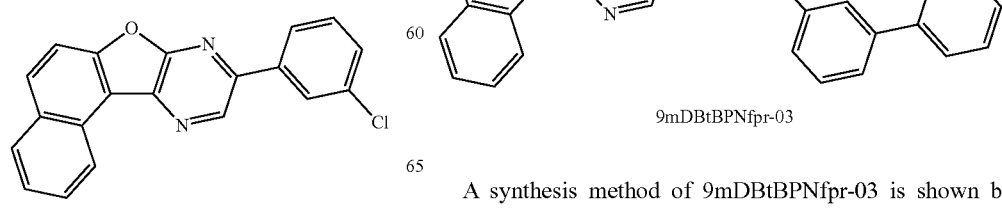

9mcgDBCzPNfpr
(117)

Reference Synthesis Example 19

A synthesis method of 9-{3'-[6-(biphenyl-3-yl)dibenzo-thiophen-4-yl]biphenyl-3-yl}naphtho[1',2':4,5]furo[2,3-b]pyrazin e (abbreviation: 9mDBtBPNfpr-03), which is the organic compound represented by Structural Formula (118) in Embodiment 1, is described. The structure of 9mDBtBPNfpr-03 is shown below.

[Chemical Formula 74]

(118)

9mDBtBPNfpr-03

A synthesis method of 9mDBtBPNfpr-03 is shown by synthesis schemes in Formula (s-1) to Formula (s-4) below.

[Chemical Formula 75]

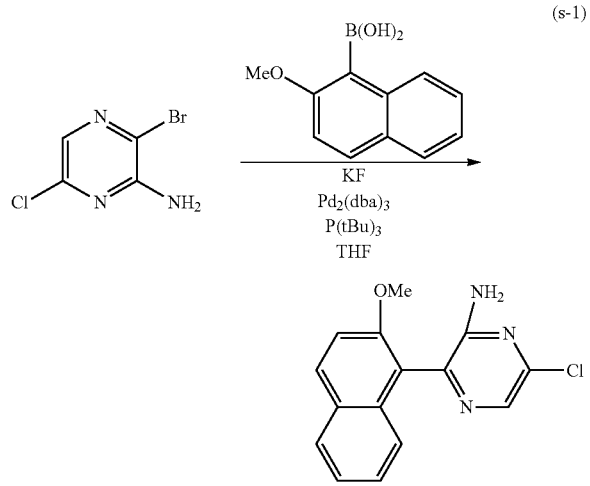

(s-1)

[Chemical Formula 76]

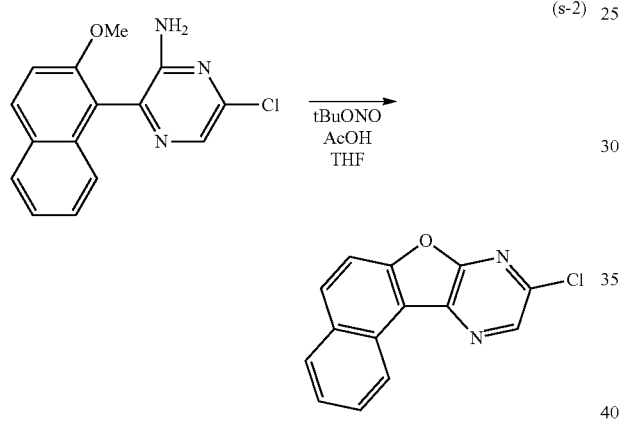

(s-2)

[Chemical Formula 77]

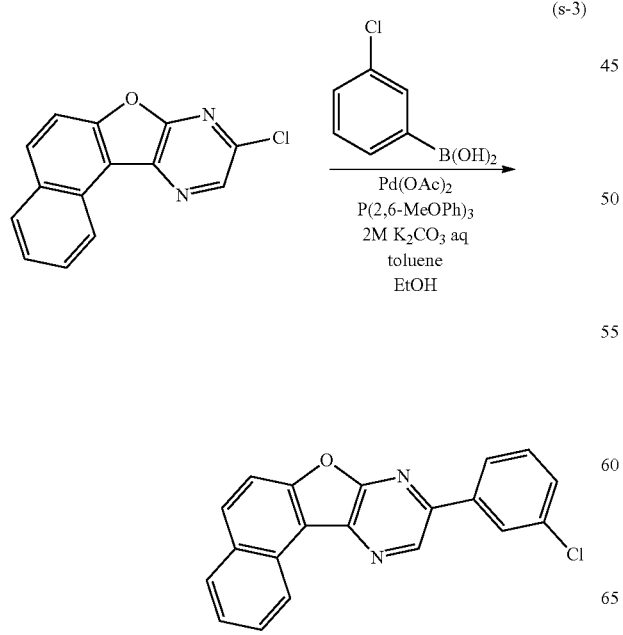

(s-3)

[Chemical Formula 78]

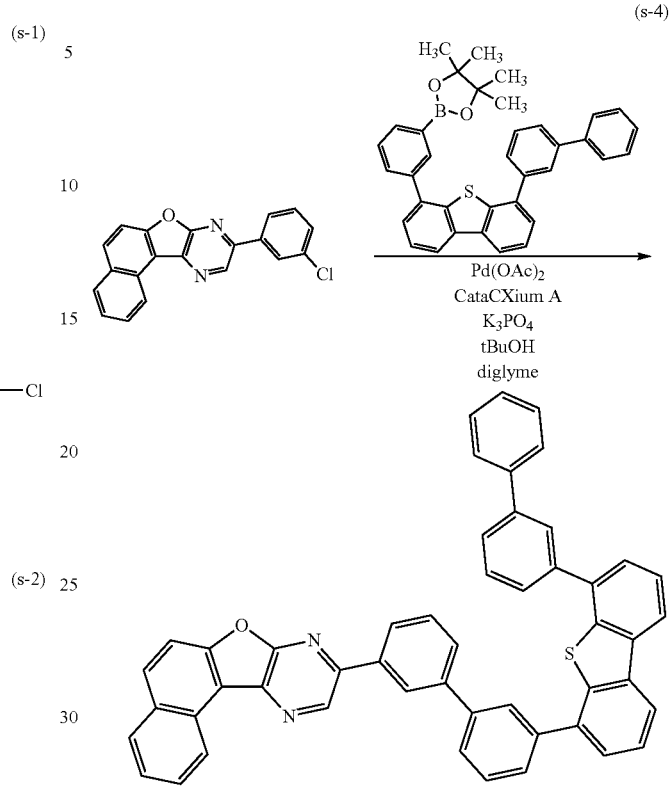

(s-4)

9mDBtBPNfpr-03
(118)

Reference Synthesis Example 20

A synthesis method of 9-{3'-[6-(biphenyl-4-yl)dibenzothiophen-4-yl]biphenyl-3-yl}naphtho[1',2':4,5]furo[2,3-b]pyrazine (abbreviation: 9mDBtBPNfpr-04), which is the organic compound represented by Structural Formula (119) in Embodiment 1, is described. The structure of 9mDBtBPNfpr-04 is shown below.

[Chemical Formula 79]

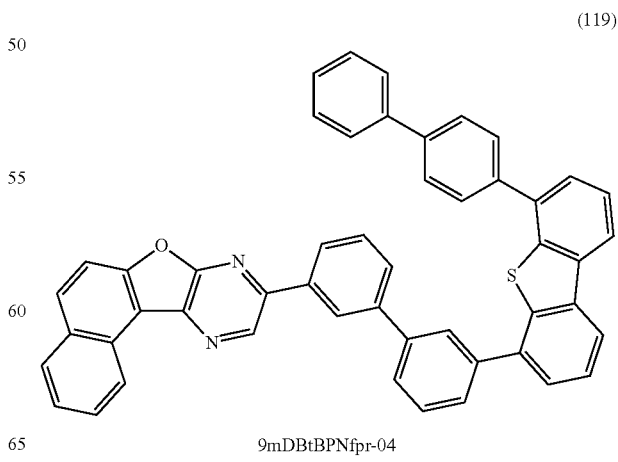

(119)

9mDBtBPNfpr-04

A synthesis method of 9mDBtBPNfpr-04 is shown by synthesis schemes in Formula (t-1) to Formula (t-4) below.

[Chemical Formula 80]

(t-1)

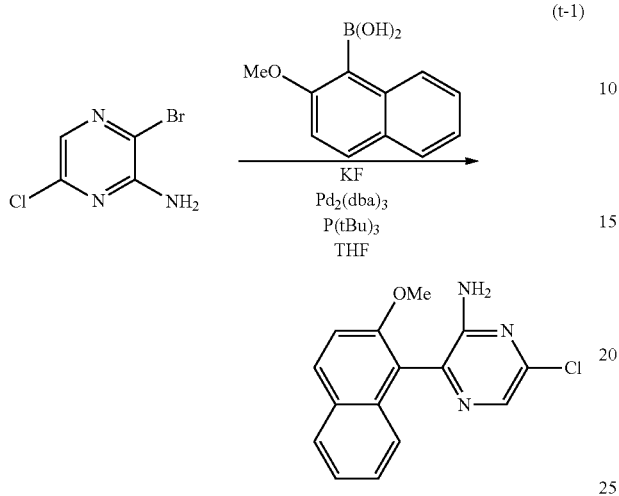

[Chemical Formula 81]

(t-2)

[Chemical Formula 82]

(t-3)

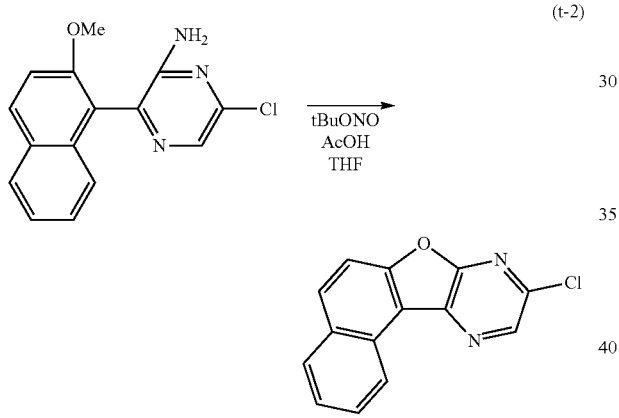

[Chemical Formula 83]

(t-4)

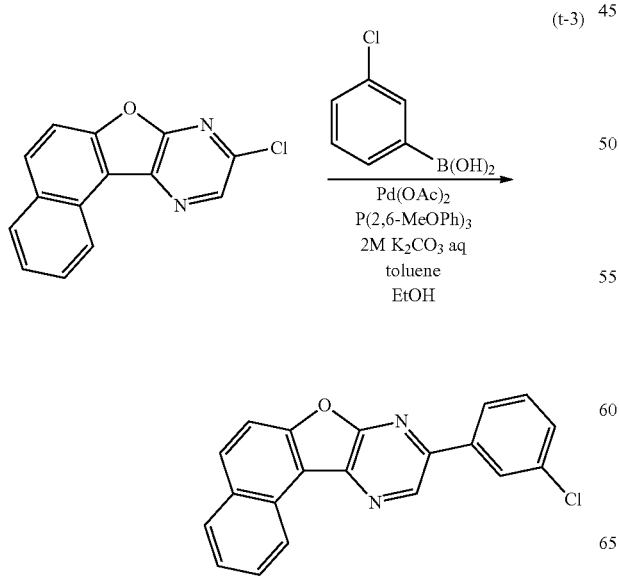

9mDBtBPNfpr-04
(119)

Reference Synthesis Example 21

A synthesis method of 11-[3'-(6-phenyldibenzothiophen-4-yl)biphenyl-3-yl]phenanthro[9',10':4,5]furo[2,3-b]pyrazine (abbreviation: 11mDBtBPPnfpr-02), which is the organic compound represented by Structural Formula (120) in Embodiment 1, is described. The structure of 11mDBtBPPnfpr-02 is shown below.

[Chemical Formula 84]

(120)

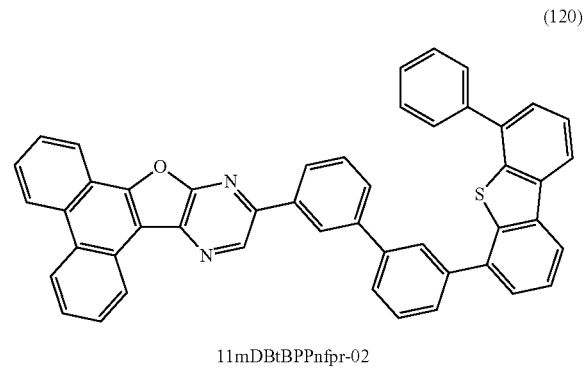

11mDBtBPPnfpr-02

A synthesis method of 11mDBtBPPnfpr-02 is shown by synthesis schemes in Formula (u-1) to Formula (u-7) below.
[Chemical Formula 85]
(u-1)
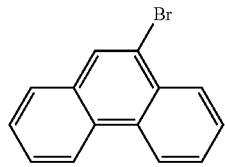
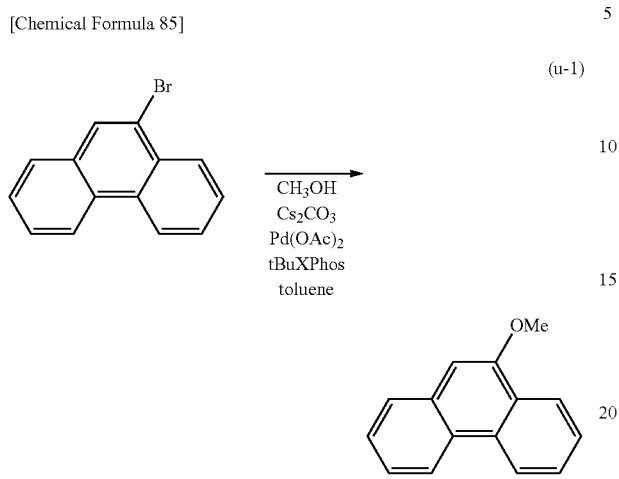
[Chemical Formula 86]
(u-2)
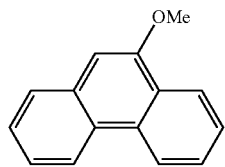
[Chemical Formula 87]
(u-3)
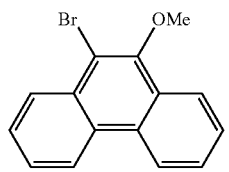
[Chemical Formula 88]
(u-4)
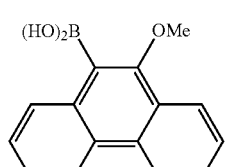
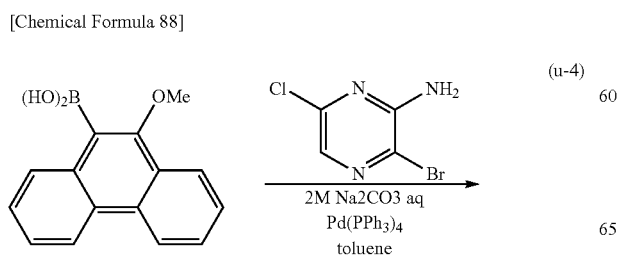
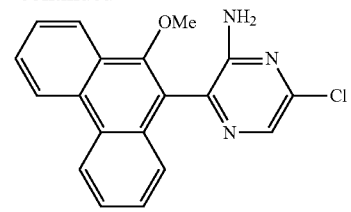
[Chemical Formula 89]
(u-5)
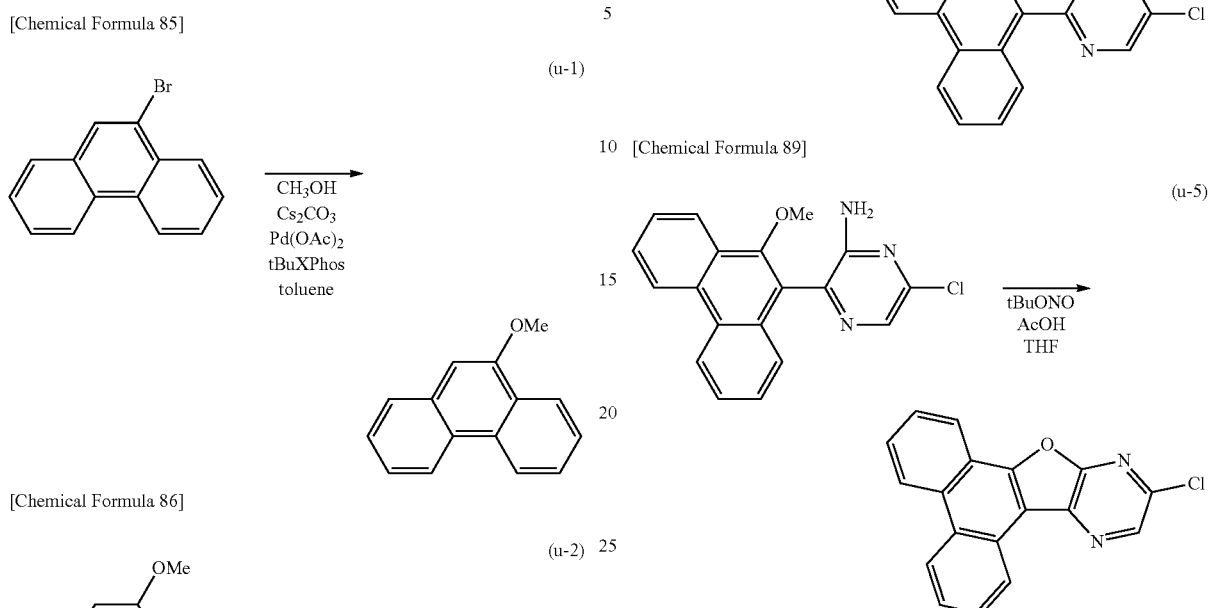
[Chemical Formula 90]
(u-6)
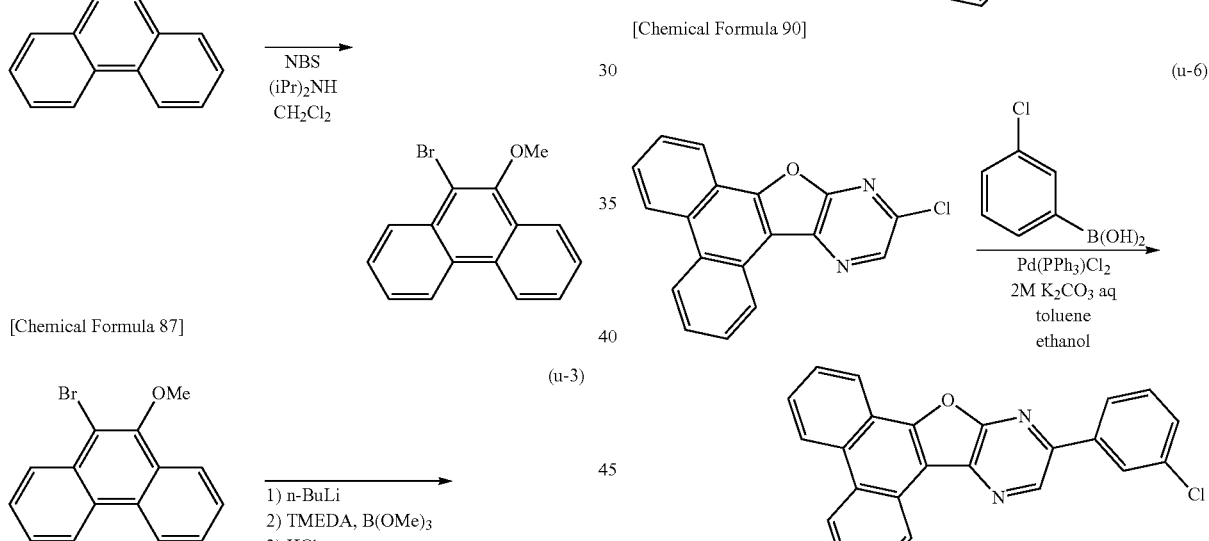
[Chemical Formula 91]
(u-7)
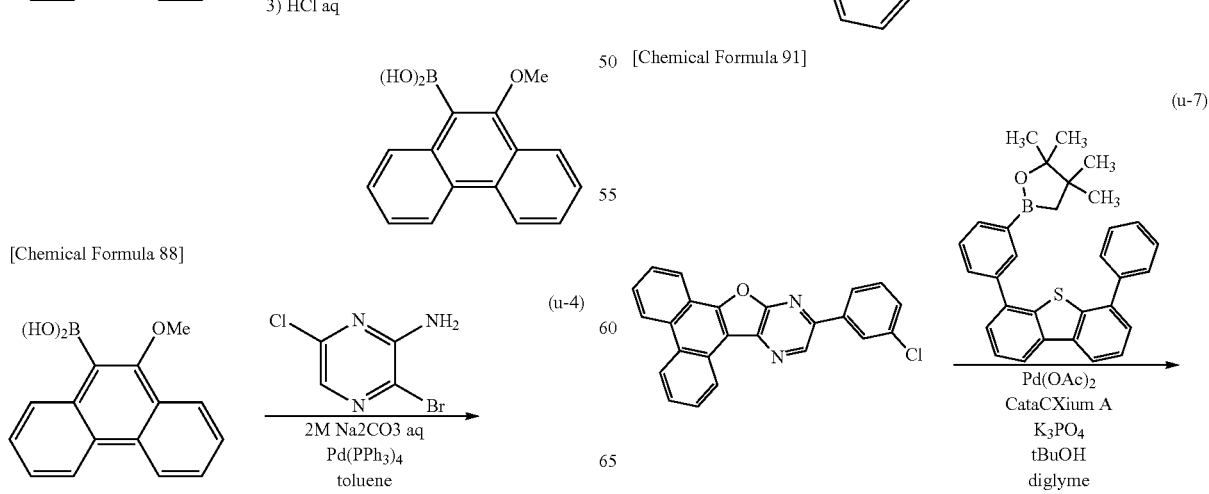

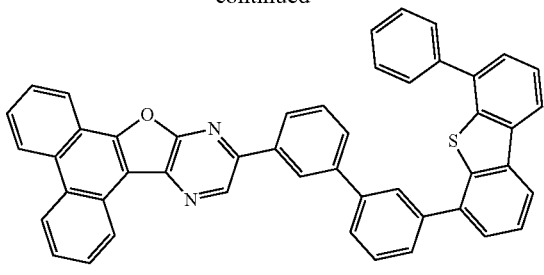

11mDBtBPPnfpr-02
(120)

REFERENCE NUMERAL

101: first electrode, 102: second electrode, 103: EL layer, 103a, 103b: EL layer, 104: charge generation layer, 111, 111a, 111b: hole-injection layer, 112, 112a, 112b: hole-transport layer, 113, 113a, 113b: light-emitting layer, 114, 114a, 114b: electron-transport layer, 115, 115a, 115b: electron-injection layer, 200R, 200G, 200B: optical path length, 201: first substrate, 202: transistor (FET), 203R, 203G, 203B, 203W: light-emitting device, 204: EL layer, 205: second substrate, 206R, 206G, 206B: color filter, 206R', 206G', 206B': color filter, 207: first electrode, 208: second electrode, 209: black layer (black matrix), 210R, 210G: conductive layer, 301: first substrate, 302: pixel portion, 303: driver circuit portion (source line driver circuit), 304a, 304b: driver circuit portion (gate line driver circuit), 305: sealant, 306: second substrate, 307: lead wiring, 308: FPC, 309: FET, 310: FET, 311: FET, 312: FET, 313: first electrode, 314: insulator, 315: EL layer, 316: second electrode, 317: light-emitting device, 318: space, 900: substrate, 901: first electrode, 902: EL layer, 903: second electrode, 911: hole-injection layer, 912: hole-transport layer, 913: light-emitting layer, 914: electron-transport layer, 915: electron-injection layer, 4000: lighting device, 4001: substrate, 4002: light-emitting device, 4003: substrate, 4004: first electrode, 4005: EL layer, 4006: second electrode, 4007: electrode, 4008: electrode, 4009: auxiliary wiring, 4010: insulating layer, 4011: sealing substrate, 4012: sealant, 4013: desiccant, 4015: diffusion plate, 4200: lighting device, 4201: substrate, 4202: light-emitting device, 4204: first electrode, 4205: EL layer, 4206: second electrode, 4207: electrode, 4208: electrode, 4209: auxiliary wiring, 4210: insulating layer, 4211: sealing substrate, 4212: sealant, 4213: barrier film, 4214: planarization film, 4215: diffusion plate, 5101: light, 5102: wheel, 5103: door, 5104: display portion, 5105: handle, 5106: shifter, 5107: seat, 5108: inner rearview mirror, 5109: windshield, 7000: housing, 7001: display portion, 7002: second display portion, 7003: speaker, 7004: LED lamp, 7005: control key, 7006: connection terminal, 7007: sensor, 7008: microphone, 7009: switch, 7010: infrared port, 7011: recording medium reading portion, 7012: support, 7013: earphone, 7014: antenna, 7015: shutter button, 7016: image receiving portion, 7018: stand, 7020: camera, 7021: external connection portion, 7022, 7023: operation button, 7024: connection terminal, 7025: band,, 7026: microphone, 7027: icon indicating time, 7028: another icon, 7029: sensor, 7030: speaker, 7052, 7053, 7054: information, 9310: portable information terminal, 9311: display portion, 9312: display region, 9313: hinge, 9315: housing This application is based on Japanese Patent Application Serial No. 2018-147134 filed with Japan Patent Office on Aug. 3, 2018, the entire contents of which are hereby incorporated herein by reference.

The invention claimed is:

1. A light-emitting device comprising an electroluminescent layer between an anode and a cathode,
wherein the electroluminescent layer comprises:
a first layer;
a second layer between the first layer and the cathode and in contact with the first layer;
a third layer between the second layer and the cathode and in contact with the second layer; and
a fourth layer between the cathode and the third layer and in contact with the third layer and the cathode,
wherein the second layer has a largest thickness in the electroluminescent layer,
wherein the second layer comprises a light-emitting substance, a first organic compound and a second organic compound,
wherein the first layer comprises the first organic compound,
wherein the third layer comprises a third organic compound,
wherein the fourth layer comprises a compound comprising an alkali metal,
wherein the third organic compound is different from the first organic compound and the second organic compound,
wherein the second organic compound has a structure in which an aromatic ring is fused to a furan ring of a furodiazine skeleton, and
wherein the second layer is a light-emitting layer.

2. The light-emitting device according to claim 1, wherein the compound comprising an alkali metal is an organic compound.

3. The light-emitting device according to claim 1, wherein the fourth layer further comprises the first organic compound.

4. The light-emitting device according to claim 1, wherein the aromatic ring in the structure included in the second organic compound is a naphthalene ring.

5. The light-emitting device according to claim 4, wherein the furodiazine skeleton in the second organic compound is a furopirazine skeleton or a furopyrimidine skeleton.

6. The light-emitting device according to claim 1, wherein the first organic compound is represented by any one of Formulae (G1), (G2) and (G3),

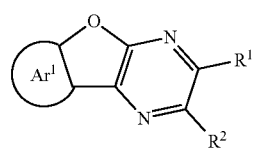

(G1)

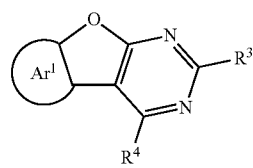

(G2)

-continued

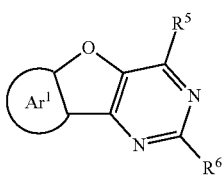
(G3)

wherein Ar¹ represents a substituted or unsubstituted aromatic ring, wherein each of $R^1$ to $R^6$ independently represents hydrogen or a group having 1 to 100 carbon atoms in total, and wherein each of at least one of $R^1$ and $R^2$, at least one of $R^3$ and $R^4$, and at least one of $R^5$ and $R^6$ has a hole-transport skeleton.

7. The light-emitting device according to claim 1, wherein the first organic compound is represented by any one Formulae (G1), (G2) and (G3),

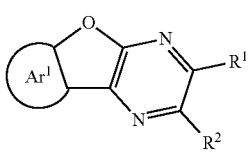
(G1)

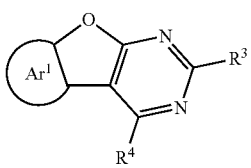
(G2)

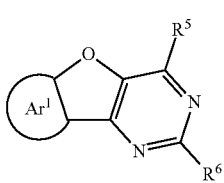
(G3)

wherein Ar¹ represents any one of substituted or unsubstituted benzene, substituted or unsubstituted naphthalene, substituted or unsubstituted phenanthrene, and substituted or unsubstituted chrysene, wherein each of $R^1$ to $R^6$ independently represents hydrogen or a group having 1 to 100 carbon atoms in total, and each of at least one of $R^1$ and $R^2$, at least one of $R^3$ and $R^4$, and at least one of $R^5$ and $R^6$ has a hole-transport skeleton.

8. The light-emitting device according to claim 6, wherein Ar¹ represents any one of Formulae (t2), (t3) and (t4),

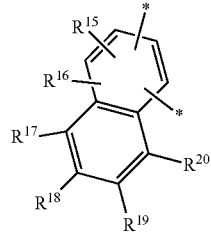
(t2)

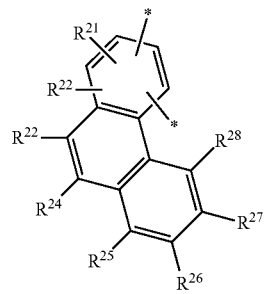
(t3)

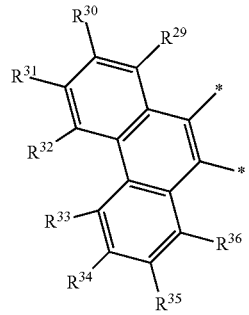
(t4)

wherein each of $R^{11}$ to $R^{36}$ independently represents any one of hydrogen, a substituted or unsubstituted alkyl group having 1 to 6 carbon atoms, a substituted or unsubstituted monocyclic saturated hydrocarbon group having 3 to 7 carbon atoms, a substituted or unsubstituted aromatic hydrocarbon group having 6 to 30 carbon atoms, and a substituted or unsubstituted heteroaromatic hydrocarbon group having 3 to 12 carbon atoms, and wherein * represents a portion bonded to the furan ring in Formulae (G1) to (G3).

9. The light-emitting device according to claim 6, wherein the group having 1 to 100 carbon atoms in each of $R^1$ to $R^6$ of Formulae (G1) to (G3), represents one of or a combination of an alkyl group having 1 to 6 carbon atoms, a substituted or unsubstituted monocyclic saturated hydrocarbon group having 5 to 7 carbon atoms, a substituted or unsubstituted polycyclic saturated hydrocarbon group having 7 to 10 carbon atoms, a substituted or unsubstituted aromatic hydrocarbon group having 6 to 13 carbon atoms, and a substituted or unsubstituted heteroaromatic hydrocarbon group having 3 to 12 carbon atoms.

10. The light-emitting device according to claim 6, wherein the group having 1 to 100 carbon atoms in each of $R^1$ to $R^6$ of Formulae (G1) to (G3), has any one of a pyrrole ring structure, a furan ring structure and a thiophene ring structure through one of a substituted or unsubstituted phenylene group and a substituted or unsubstituted biphenylene group.

11. The light-emitting device according to claim 6, wherein the group having 1 to 100 carbon atoms in each of $R^1$ to $R^6$ of Formulae (G1) to (G3), has a structure represented by any one of Formulae (Ht-1) to (Ht-26) through one of a substituted or unsubstituted phenylene group and a substituted or unsubstituted biphenylene group,
(Ht-1)
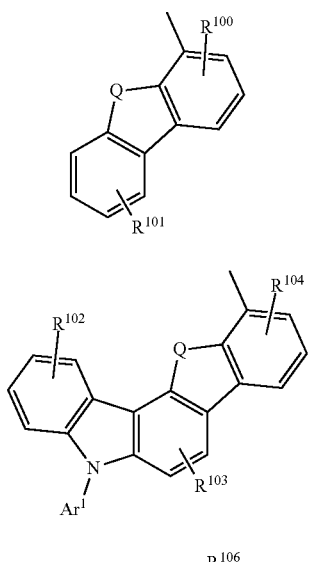
(Ht-2)
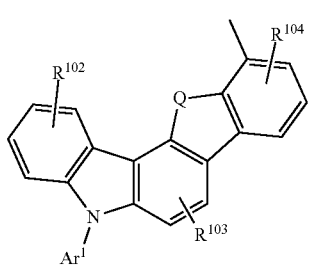
(Ht-3)
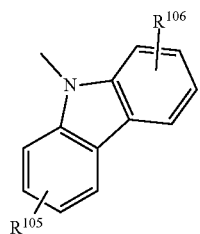
(Ht-4)
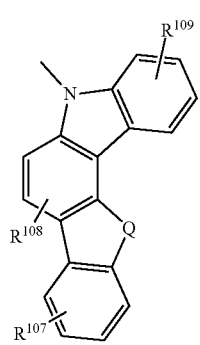
(Ht-5)
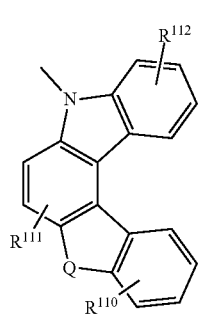
-continued
(Ht-6)
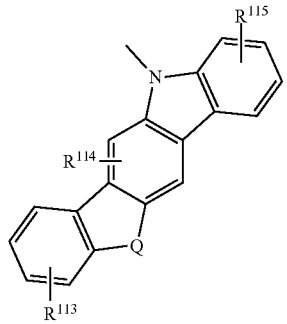
(Ht-7)
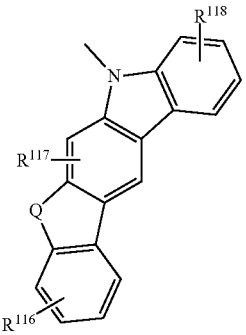
(Ht-8)
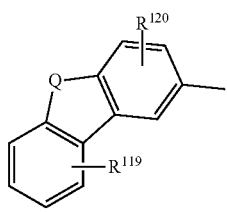
(Ht-9)
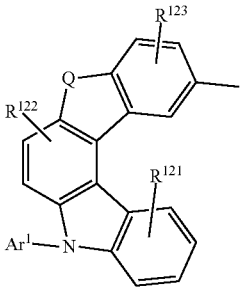
(Ht-10)
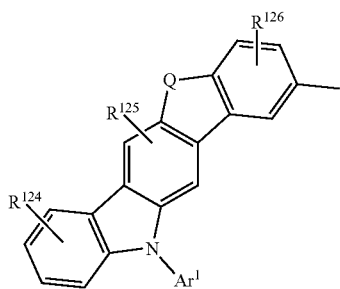

(Ht-11) 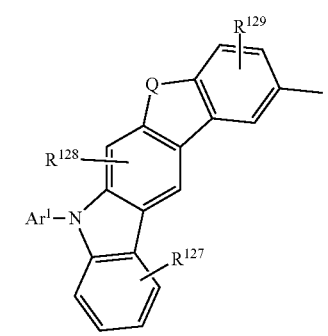
(Ht-12) 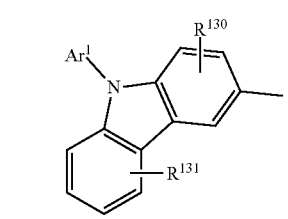
(Ht-13) 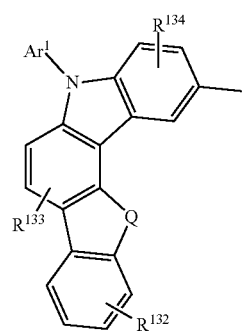
(Ht-14) 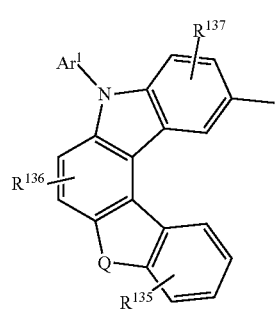
(Ht-15) 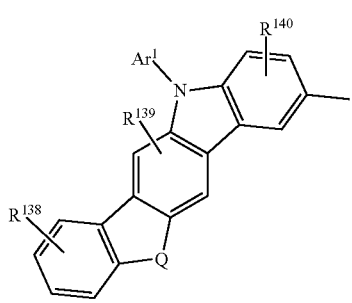
(Ht-16) 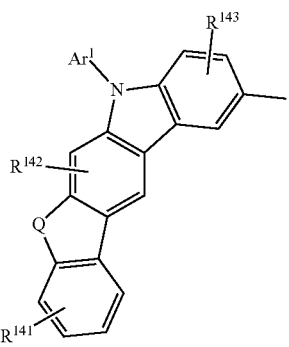
(Ht-17) 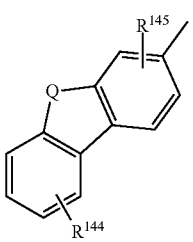
(Ht-18) 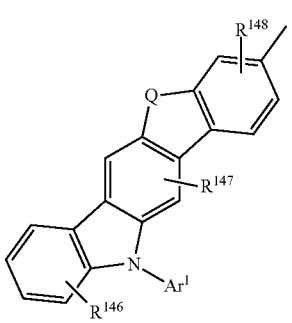
(Ht-19) 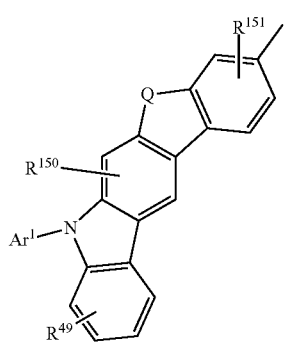
(Ht-20) 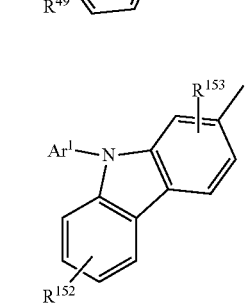

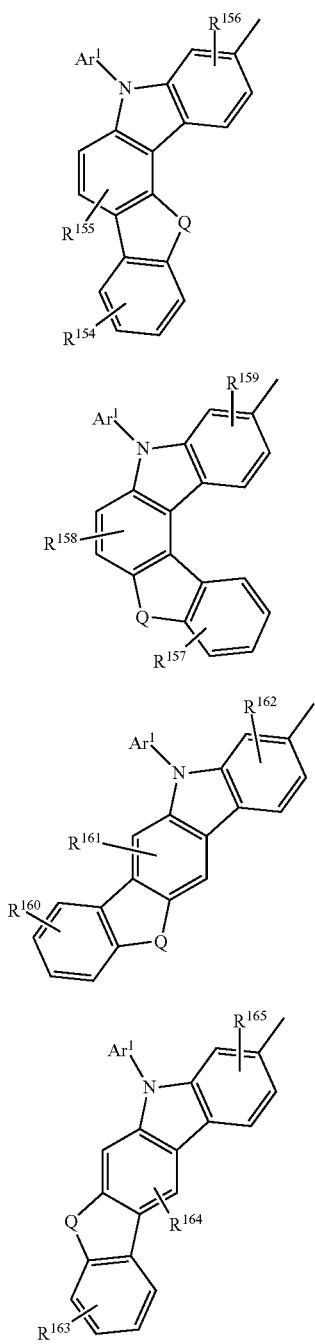

(Ht-21)

(Ht-22)

(Ht-23)

(Ht-24)

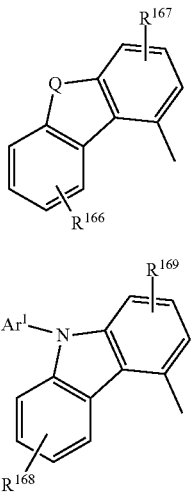

(Ht-25)

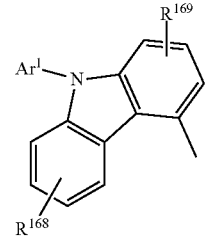

(Ht-26)

wherein Q represents oxygen or sulfur, wherein each of $R^{100}$ to $R^{169}$ represents 1 to 4 substituents and independently represents any one of hydrogen, an alkyl group having 1 to 6 carbon atoms, and a substituted or unsubstituted aromatic hydrocarbon group having 6 to 13 carbon atoms, and wherein $Ar^1$ represents a substituted or unsubstituted aromatic hydrocarbon group having 6 to 13 carbon atoms.

12. The light-emitting device according to claim 1, wherein the light-emitting substance is a phosphorescent material.

13. The light-emitting device according to claim 1, wherein the first organic compound is a carbazole derivative.

14. The light-emitting device according to claim 13, wherein the carbazole derivative is a bicarbazole derivative.

15. The light-emitting device according to claim 1, wherein the first layer is a hole-transport layer.

16. A light-emitting apparatus comprising:
the light-emitting device according to claim 1; and
a flexible printed circuit.

17. An electronic device comprising:
the light-emitting apparatus according to claim 16; and
at least one of a microphone, a camera, an operation button, an external connection portion and a speaker.

18. A lighting device comprising:
the light-emitting device according to claim 1; and
at least one of a housing and a cover.

* * * * *